United States Patent
Hawkins et al.

(10) Patent No.: US 10,087,175 B2
(45) Date of Patent: Oct. 2, 2018

(54) SIGMA-2 RECEPTOR LIGAND DRUG CONJUGATES AS ANTITUMOR COMPOUNDS, METHODS OF SYNTHESIS AND USES THEREOF

(71) Applicant: Washington University, St. Louis, MO (US)

(72) Inventors: William Hawkins, St. Louis, MO (US); Robert Mach, St. Louis, MO (US); Dirk Spitzer, St. Louis, MO (US); Suwanna Vangveravong, St. Louis, MO (US); Brian Van Tine, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/301,188

(22) PCT Filed: Apr. 1, 2015

(86) PCT No.: PCT/US2015/023954
§ 371 (c)(1),
(2) Date: Sep. 30, 2016

(87) PCT Pub. No.: WO2015/153814
PCT Pub. Date: Oct. 8, 2015

(65) Prior Publication Data
US 2017/0015660 A1    Jan. 19, 2017

Related U.S. Application Data

(60) Provisional application No. 61/973,366, filed on Apr. 1, 2014.

(51) Int. Cl.
| | | |
|---|---|---|
| C07D 451/14 | (2006.01) | |
| C07D 471/08 | (2006.01) | |
| A61K 31/517 | (2006.01) | |
| A61K 31/496 | (2006.01) | |
| A61K 45/06 | (2006.01) | |

(52) U.S. Cl.
CPC .......... *C07D 451/14* (2013.01); *A61K 31/496* (2013.01); *A61K 31/517* (2013.01); *A61K 45/06* (2013.01); *C07D 471/08* (2013.01)

(58) Field of Classification Search
None
See application file for complete search history.

(56) References Cited

U.S. PATENT DOCUMENTS

| | | |
|---|---|---|
| 8,143,222 B2 | 3/2012 | McDunn et al. |
| 2004/0248221 A1 | 12/2004 | Stockwell |
| 2007/0161644 A1 | 7/2007 | Stockwell |

FOREIGN PATENT DOCUMENTS

| | | |
|---|---|---|
| WO | 2006081331 A2 | 8/2006 |
| WO | 2006081337 A2 | 8/2006 |
| WO | 2006081337 A3 | 8/2006 |
| WO | 2006130426 A2 | 12/2006 |
| WO | 2006130426 A3 | 12/2006 |
| WO | 2007076087 A2 | 7/2007 |
| WO | 2007076087 A3 | 7/2007 |
| WO | 2008042926 A1 | 4/2008 |
| WO | 2015153814 A1 | 10/2015 |

OTHER PUBLICATIONS van Waarde et al. Biochimica et Biophysica Acta 1848 (2015), p. 2703-2714.*
Cancer Drug Design and Discovery, Neidle, Stephen,ed. (Elsevier/Academic Press), pp. 427-431 (2008).*
Abate, C. et al., "Elements in support of the 'non-identity' of the PGRMC1 protein with the σ2 receptor," Euro. J. Pharmacol., 2015, pp. 16-23, vol. 758, Elsevier B.V.
Ahmed, I. et al., "The heme-1 domain protein PGRMC1 promotes tumor growth," JPET, Feb. 17, 2010, pp. 1-29 and 5 drawings pgs., No. 164210, American Society for Pharmacology and Experimental Therapeutics.
Besmer, D. et al., "Pancreatic Ductal Adenocarcinoma Mice Lacking Mucin 1 Have a Profound Defect in Tumor Growth and Metastasis," Cancer Res., Jul. 1, 2011, pp. 4432-4442, vol. 71, No. 13.
Bowen, W. et al., "σ2 Receptors: Regulation of Cell Growth and Implications for Cancer Diagnosis and Therapeutics," Brown University, Department of Molecular Pharmacology, Physiology, & Biotechnology, 2007, pp. 215-235, Chapter 11.
Dehdashti, F. et al., "Assessment of Cellular Proliferation in Tumors by PET Using 18F-ISO-1," J. Nucl. Med., Mar. 2013, pp. 350-357, vol. 54, No. 3.
Dixon, S. et al., "Ferroptosis: An Iron-Dependent Form of Nonapoptotic Cell Death," Cell, May 25, 2012, pp. 1060-1072, vol. 149, Elsevier, Inc.
Dixon, S. et al., "Pharmacological inhibition of cystine-glutamate exchange induces endoplasmic reticulum stress and ferroptosis," eLife Research Article, 2014, pp. 1-25.
Garg, G. et al., "Conjugation to a SMAC mimetic potentiates sigma-2 ligand induced tumor cell death in ovarian cancer," Molecular Cancer, 2014, pp. 1-13, vol. 13, No. 50.
Hashim, Y. et al., "Targeted pancreatic cancer therapy with the small molecule drug conjugate SW IV-134," Molecular Oncology, 2014, pp. 956-967, vol. 8, Elsevier B.V.
Hashim, Y. et al., "The Targeted SMAC Mimetic SW IV-134 is a strong enhancer of standard chemotherapy in pancreatic cancer," Journal of Experimental & Clinical Cancer Res., 2017, pp. 1-10, vol. 36, No. 14.
Hornick, J. et al., "The novel sigma-2 receptor ligand SW43 stabilizes pancreas cancer progression in combination with gemcitabine," Molecular Cancer, 2010, pp. 1-11, vol. 9, No. 298.

(Continued)

*Primary Examiner* — Emily A Bernhardt

(57) ABSTRACT

Methods and compositions for treating cancers such as pancreatic cancer and synovial sarcoma are disclosed. Compounds comprising a sigma-2 receptor-binding moiety and a ferroptosis-inducing moiety are described. At least one described molecular species exhibits an $IC_{50}$ value below 5 µM against human pancreatic cancer cells in vitro. Administration of this species promoted shrinkage of pancreatic cancer tumors in a murine model system in vivo, and led to 100% survival of experimental animals over a time course in which control therapies provided only 30% or 40% survival. Methods of synthesis of molecular species are also disclosed.

28 Claims, 18 Drawing Sheets

(56) References Cited

OTHER PUBLICATIONS

Hornick, J. et al., "Lysosomal Membrane Permeabilization is an Early Event in Sigma-2 Receptor Ligand Mediated Cell Death in Pancreatic Cancer," Journal of Experimental & Clinical Cancer Res., 2012, pp. 1-11, vol. 31, No. 41.
Hornick, J. et al., "Therapeutic targeting of pancreatic cancer utilizing sigma-2 ligands," NIH Public Access Author Manuscript, Apr. 10, 2014, pp. 1-8, Published in final edited form as: Surgery, Sep. 2012, pp. S152-S156, vol. 152, No. 301.
Kashiwagi, H. et al., "Selective sigma-2 ligands preferentially bind to pancreatic adenocarcinomas: applications in diagnostic imaging and therapy," Molecular Cancer, 2007, pp. 1-12, vol. 6, No. 48.
Kashiwagi, H. et al., "Sigma-2 receptor ligands potentiate conventional chemotherapies and improve survival in models of pancreatic adenocarcinoma," Journal of Translational Medicine, 2009, pp. 1-8, vol. 7, No. 24.
Kawai, A. et al., "Establishment and characterization of a biphasic synovial sarcoma cell line, SYO-1," Cancer Letters, 2004, pp. 105-113, vol. 204, Elsevier, Inc.
Mach, R. et al., "The σ2 Receptor: A Novel Protein for the Imaging and Treatment of Cancer," J. Med. Chem., 2013, pp. 7137-7160, vol. 56, American Chemical Society.
Ohman, K. et al., "Conjugation to the sigma-2 ligand SV119 overcomes uptake blockade and converts dm-Erastin into a potent pancreatic cancer therapeutic," Oncotarget, 2016, pp. 33529-33541, vol. 7, No. 23.
Spitzer, D. et al., "Use of Multifunctional Sigma-2 Receptor Ligand Conjugates to Trigger Cancer-Selective Cell Death Signaling," Cancer Res., Jan. 1, 2012, pp. 201-209, vol. 72, No. 1.
Su, Y. et al., "Mesothelin's minimal MUC16 binding moiety converts TR3 into a potent cancer therapeutic via hierarchical binding events at the plasma membrane," Oncotarget, 2016, pp. 31534-31549, vol. 7, No. 21.
Sun, T. et al., "Using SV119-Gold Nanocage Conjugates to Eradicate Cancer Stem Cells Through a Combination of Photothermal and Chemo Therapies," Adv. Healthcare Mater., 2014, pp. 1283-1291, vol. 3, Wiley-VCH Verlag GmbH & Co., KGaA, Weinheim.
Tinder, T. et al., "MUC1 Enhances Tumor Progression and Contributes Toward Immunosuppression in a Mouse Model of Spontaneous Pancreatic Adenocarcinoma," J. Immunol., 2008, pp. 3116-3125, vol. 181.
Xu, J. et al., "Identification of the PGRMC1 protein complex as the putative sigma-2 receptor binding site," NIH Public Access Author Manuscript, 2013, pp. 1-14, Published in final edited form as: Nat. Commun., vol. 2, No. 380.
Zeng, C. et al., "Subcellular Localization of Sigma-2 Receptors in Breast Cancer Cells Using Two-Photon and Confocal Microscopy," Cancer Res., Jul. 15, 2007, pp. 6708-6716, vol. 67, No. 14.
Zeng, C. et al., "Characterization and Evaluation of Two Novel Fluorescent Sigma-2 Receptor Ligands as Proliferation Probes," Molecular Imaging, 2011, pp. 1-14, Decker Publishing.
Zeng, C. et al., "Sigma-2 receptor ligand as a novel method for delivering a SMAC mimetic drug for treating ovarian cancer," British Journal of Cancer, 2013, pp. 2368-2377, vol. 109, Cancer Research U.K.
International Search Report and Written Opinion dated Aug. 3, 2015 from related Patent Application No. PCT/US2015/023954; 15 pgs.
Extended European Search Report dated Jul. 14, 2017 from related European Patent Application No. 15773524.2; 7 pgs.

* cited by examiner

Erastin　　　　　　　　　　Des-methyl erastin
　　　　　　　　　　　　　　　SW V-27 n = 1, SW V-49s
n = 5, SW V-50s

IC 50 of KCKO, 15 k cells/well, 96 wells plate 24 hrs treatment with SW-V-49s and controls Lethality of SWV-49s in SYO cells (too potent to accurately measure LC-50)

SIGMA-2 RECEPTOR LIGAND DRUG CONJUGATES AS ANTITUMOR COMPOUNDS, METHODS OF SYNTHESIS AND USES THEREOF

CROSS-REFERENCE TO RELATED APPLICATIONS

This application claims the benefit of PCT Application PCT/US2015/023954, filed Apr. 1, 2015, which claims the benefit of U.S. Provisional Application No. 61/973,366, filed Apr. 1, 2014, each of the contents of which is hereby incorporated by reference in its entirety.

STATEMENT REGARDING FEDERALLY SPONSORED RESEARCH OR DEVELOPMENT

The invention was made with government support under 5R01CA163764-03 awarded by the National Institutes of Health. The government has certain rights in the invention.

FIELD

The present disclosure relates to sigma-2 receptor binding compounds and compositions, and their application as pharmaceuticals for the treatment of disease. More particularly, embodiments are related to sigma-2 receptor ligand-drug conjugates, their synthesis and their use for treating hyperproliferative diseases such as cancer.

DESCRIPTION OF RELATED ART

Pancreatic cancer is the fourth leading cause of cancer death, and is expected to be the second leading cause in 2020. The five-year survival rate for pancreatic cancer is only 5.8% with current treatment options and there is a desperate need for new therapies Sigma-2 receptors (S2R) are over-expressed in pancreatic ductal adenocarcinomas (PDAC) cells and have a high affinity for S2R ligands. S2R ligands localize to PDAC cells and are rapidly internalized by the cancer cells, eventually leading to apoptosis and cell death. S2R ligands also potentiate conventional anticancer chemotherapies and improve survival in models of pancreatic adenocarcinoma.

S2R ligands linked to small molecule imaging tags have been used to demonstrate that S2R ligands preferentially bind to pancreatic adenocarcinomas, and can be used to visualize the S2R on cancer cells. Similarly, S2R ligands can be linked to proapoptotic peptides or peptidomimetics, which can be selectively delivered into cancer cells.

Erastin, of structure:

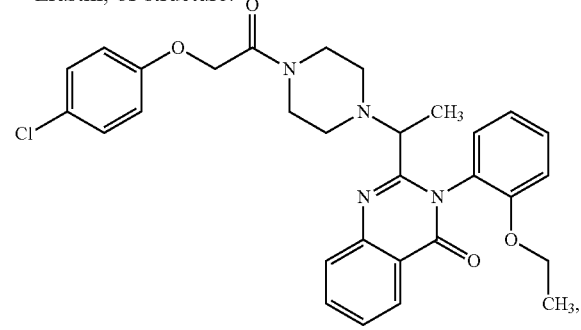 [SMILES: CCOc1ccccc1-n1c(C(C)N2CCN(C(=O)COc3ccc(Cl)cc3)CC2)nc2ccccc2c1=O]

is a drug with selectivity for killing cells with oncogenic K-ras mutations by mediating cell death by an iron-dependent, non-apoptotic process termed ferroptosis. However, this drug underperformed in initial clinical trials.

Erastin has been described in US Patent Application Publication 2007/0161644 of Stockwell, B. R., as having cell killing properties that are non-apoptotic. This reference also disclosed certain Erastin analogs, such as Erastin A of structure

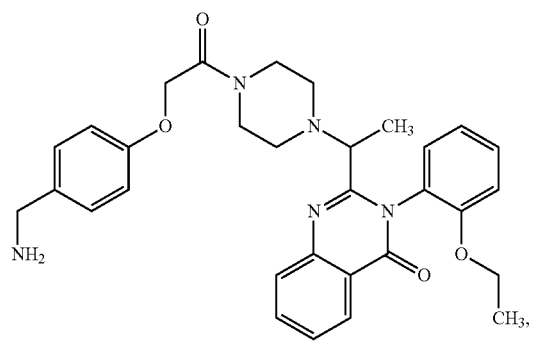 [SMILES: CCOc1ccccc1-n1c(C(C)N2CCN(C(=O)COc3ccc(CN)cc3)CC2)nc2ccccc2c1=O]

Erastin B of structure

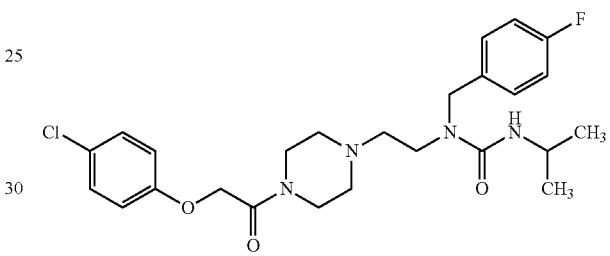

and des-methyl Erastin (designated "compound 21") of structure

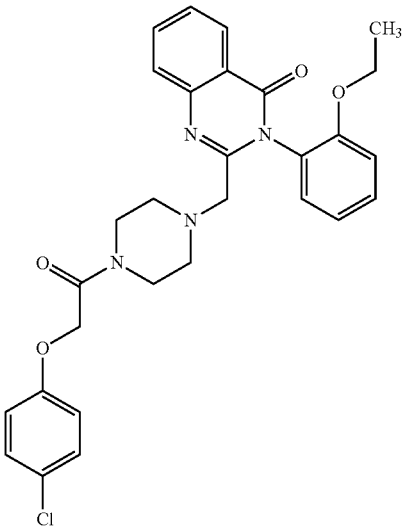 [SMILES: CCOc1ccccc1-n1c(CN2CCN(C(=O)COc3ccc(Cl)cc3)CC2)nc2ccccc2c1=O]

(also designated herein as SW V-27). The inventor in this application asserted that des-methyl Erastin has tumor cell-killing activity comparable to that of Erastin. Dixon, S. J., et al., Cell 149: 1060-1072, 2012 describes Erastin as mediating a nonapoptotic, iron-dependent oxidative cell death ("ferroptosis"). However, these references do not describe compounds comprising a bicyclic moiety, and the compounds described do not also mediate apoptotic cell death.

U.S. Pat. No. 8,143,222 to McDunn, J. E., et al. as well as Spitzer, D. et al., Cancer Res. 72: 201-209, 2012 and Hornick, J. R., et al. Molecular Cancer 9: 298, 2010 disclose compounds for beating cancer. Compounds disclosed in these references include molecules having a targeting moiety which binds sigma-2 receptor (Zeng, C., et al., Cancer Res. 67: 6708-6716, 2007) and an apoptosis-inducing moiety such as a proapoptotic peptide. Disclosed compounds include a sigma-2 receptor ligand such as an N-substituted 9-azabicyclo[3.3.1]nonan-3α-yl phenylcarbamate moiety of structure:

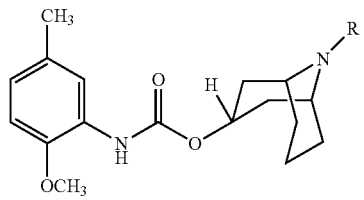

wherein R can be selected from the group consisting of a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, an ester and a hydrophilic polymer. In some configurations, compounds of this patent include alkylamine derivatives of a bicyclic phenylcarbamate moiety, such as

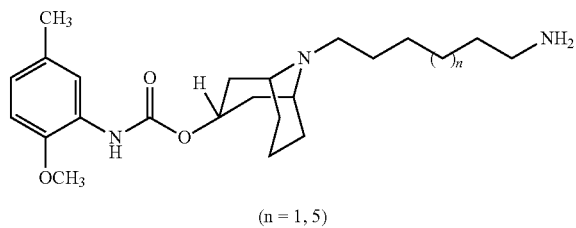

(n = 1, 5)

(Designated SV119 when n=1) and SW43 of structure

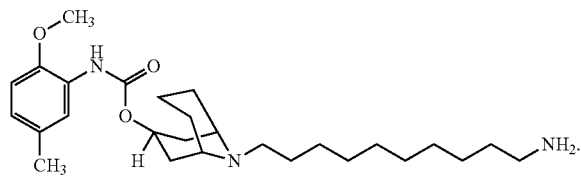 [SMILES: COc1ccc(C)cc1NC(=O)OC1CC2CCCC(C1)N2CCCCCCCCCCN]

Although some compounds disclosed in these references are described as having tumor cell killing activity, none of them are disclosed to mediate iron-dependent oxidative cell death (ferroptosis).

SUMMARY

Accordingly, the inventors herein disclose new compositions and compounds and methods of their synthesis, and methods for treating hyperproliferative disorders, including various cancers.

In various embodiments, the present teachings include compounds of structural Formula I

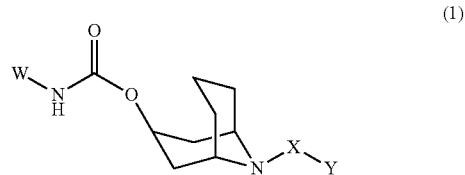

(1)

and salts thereof, wherein: W can be an aryl group such as a $C_5$-$C_{10}$ aryl or a $C_5$-$C_{10}$ heteroaryl, any of which can be substituted; X can be a linking moiety such as, but not limited to a linear alkyl chain; and Y can be a ferroptosis-inducing moiety such as erastin, an erastin analog such as erastin-A, erastin-B, desmethyl-erastin or an erastin mimetic.

In various embodiments, the present teachings include compositions comprising a compound of Formula I and a pharmaceutically acceptable carrier, adjuvant, or vehicle.

In various embodiments, the present teachings include methods of treating a hyperproliferative disorder in a subject in need thereof, comprising the step of administering to the subject a compound of Formula I.

In various embodiments, the present teachings include methods of treating a hyperproliferative disorder in a subject in need thereof, comprising the sequential or co-administration of a compound of Formula I or a pharmaceutically acceptable salt thereof, and another therapeutic agent.

In various embodiments, the present teachings include compounds of Formula I for use in human therapy.

In various embodiments, the present teachings include compounds of any of Formula I for use in treating a hyperproliferative disorder.

In various embodiments, the present teachings include use of a compound of Formula I for the manufacture of a medicament to treat a hyperproliferative disorder.

In various embodiments, the present teachings include compounds or a salt thereof, of structure

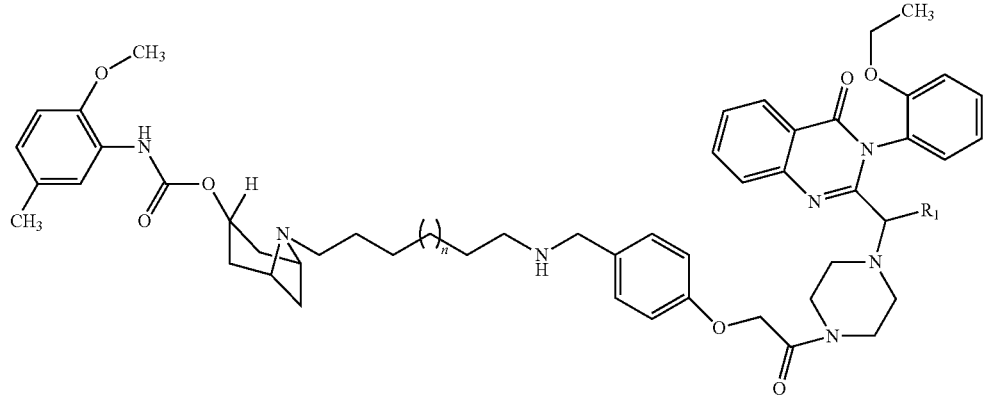

wherein n is an integer from 1 to 5 and $R_1$ can be H or methyl. In some configurations, compounds or salts of these embodiments include compounds and salts wherein n can be 1 and $R_1$ can be H. In some configurations, compounds or salts of these embodiments include compounds and salts wherein n can be 5 and $R_1$ can be H. In various configurations, a salt of a compound of these embodiments can be an oxalate salt.

In various embodiments, these compounds and salts thereof can be used in methods of treating cancers. In various configurations, these methods can comprise administering to a subject in need thereof a therapeutically effective amount any of these compounds or salts thereof. In various configurations, a cancer that can be treated with any of these compounds or salts thereof can be any cancer, such as, without limitation, a pancreatic cancer or a synovial sarcoma.

In various embodiments, these compounds and salts thereof can be synthesized by methods disclosed herein. In some configurations, these methods can comprise reacting a compound of structure wherein n can be an integer from 1 to 5 and $R_1$ can be methyl or H. In some configurations, n can be 1 and $R_1$ can be an H. In some configurations, n can be 5 and $R_1$ can be an H.

In some configurations, the present teachings include these compounds or salts thereof for use in the treatment of a cancer. In some aspects, the cancer can be, without limitation, a pancreatic cancer or a synovial sarcoma.

In some configurations, the present teachings include use of these compounds or salts thereof for the manufacture of a medicament for the treatment of cancer. In some aspects, the cancer can be, without limitation, a pancreatic cancer or a synovial sarcoma.

In various embodiments, the present teachings include methods of synthesizing a compound of Formula IV:

(IV)

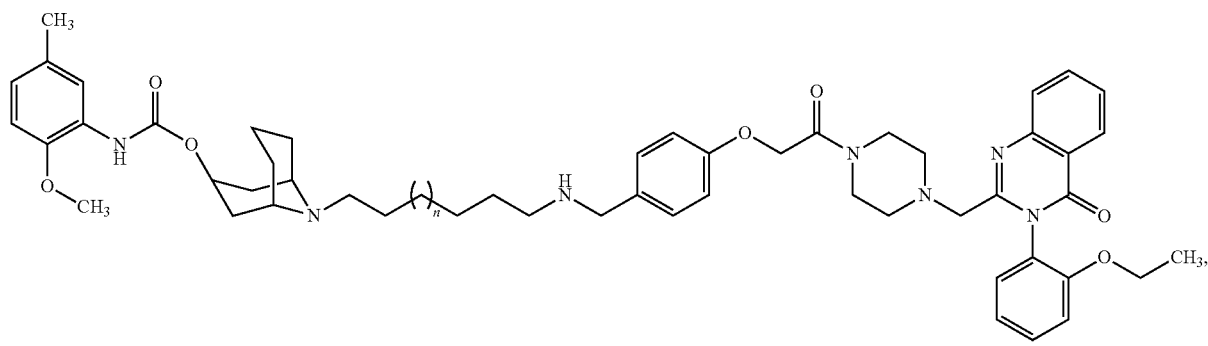

comprising the step of reacting a compound of structural Formula V:

(V)

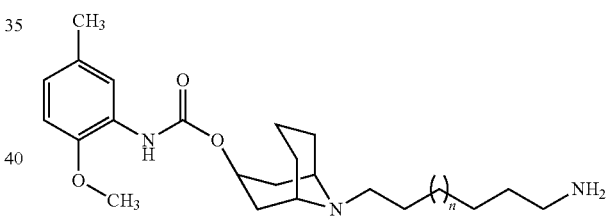

with a compound of structural Formula VI:

(VI)

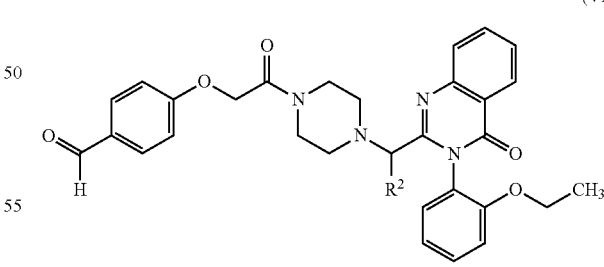

wherein n is an integer from 1 to 5; and $R^2$ can be H or methyl.

with a compound of structure

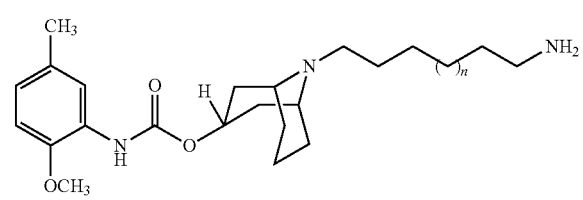

Figure 1:
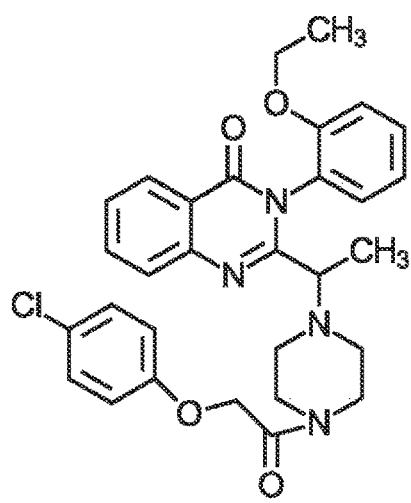
FIG. 1 illustrates Erastin and des-methyl Erastin (SW V-27).
Figure 1:
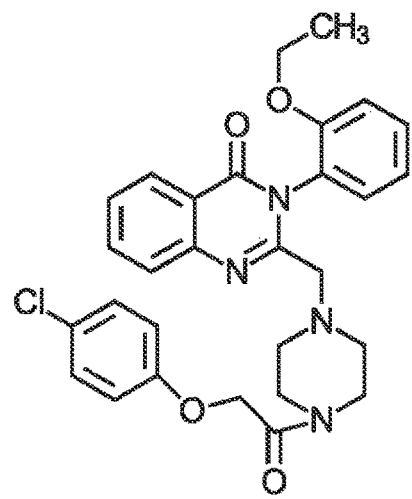
Figure 2A:
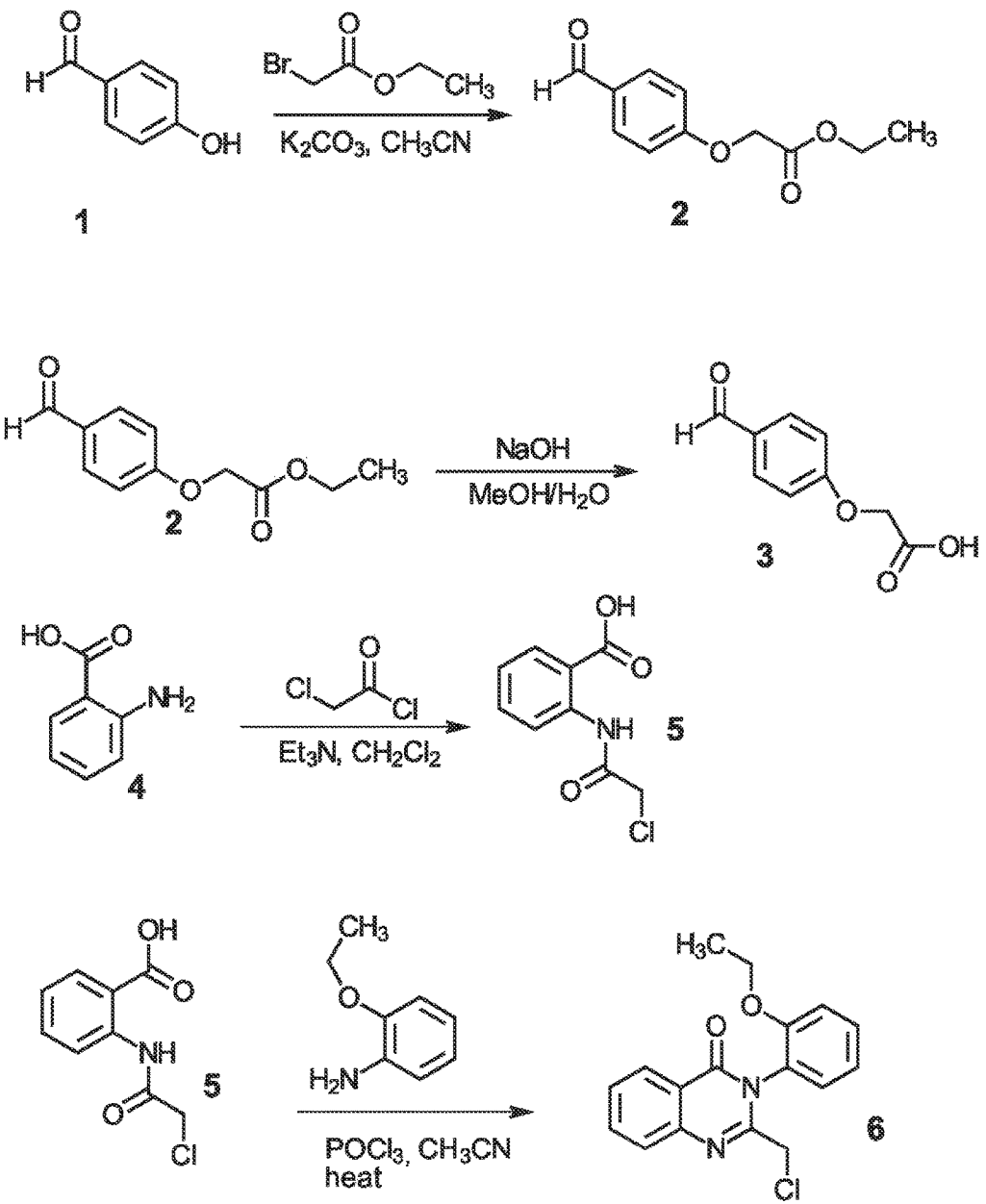
FIG. 2A-C illustrate synthesis of compounds SW V-49s and SW V-50s of the present teachings.
Figure 2B:
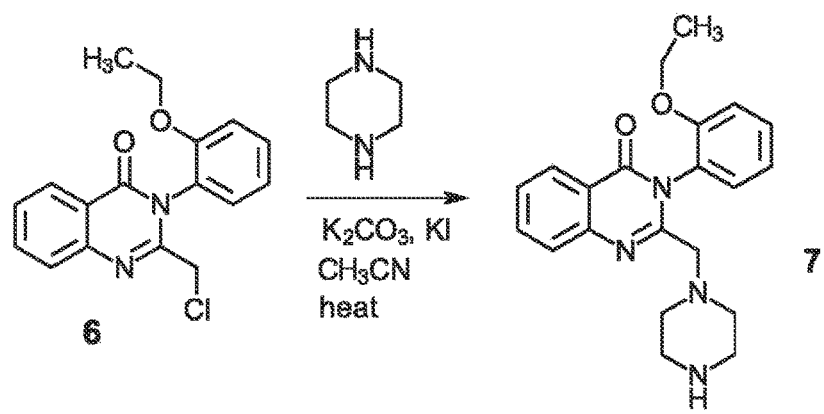
Figure 2B:
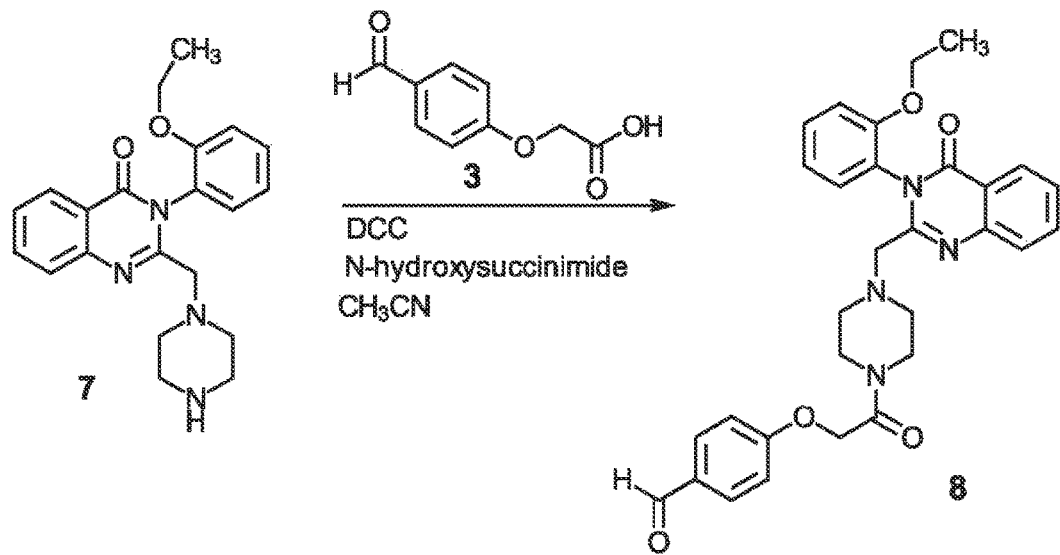
Figure 2C:
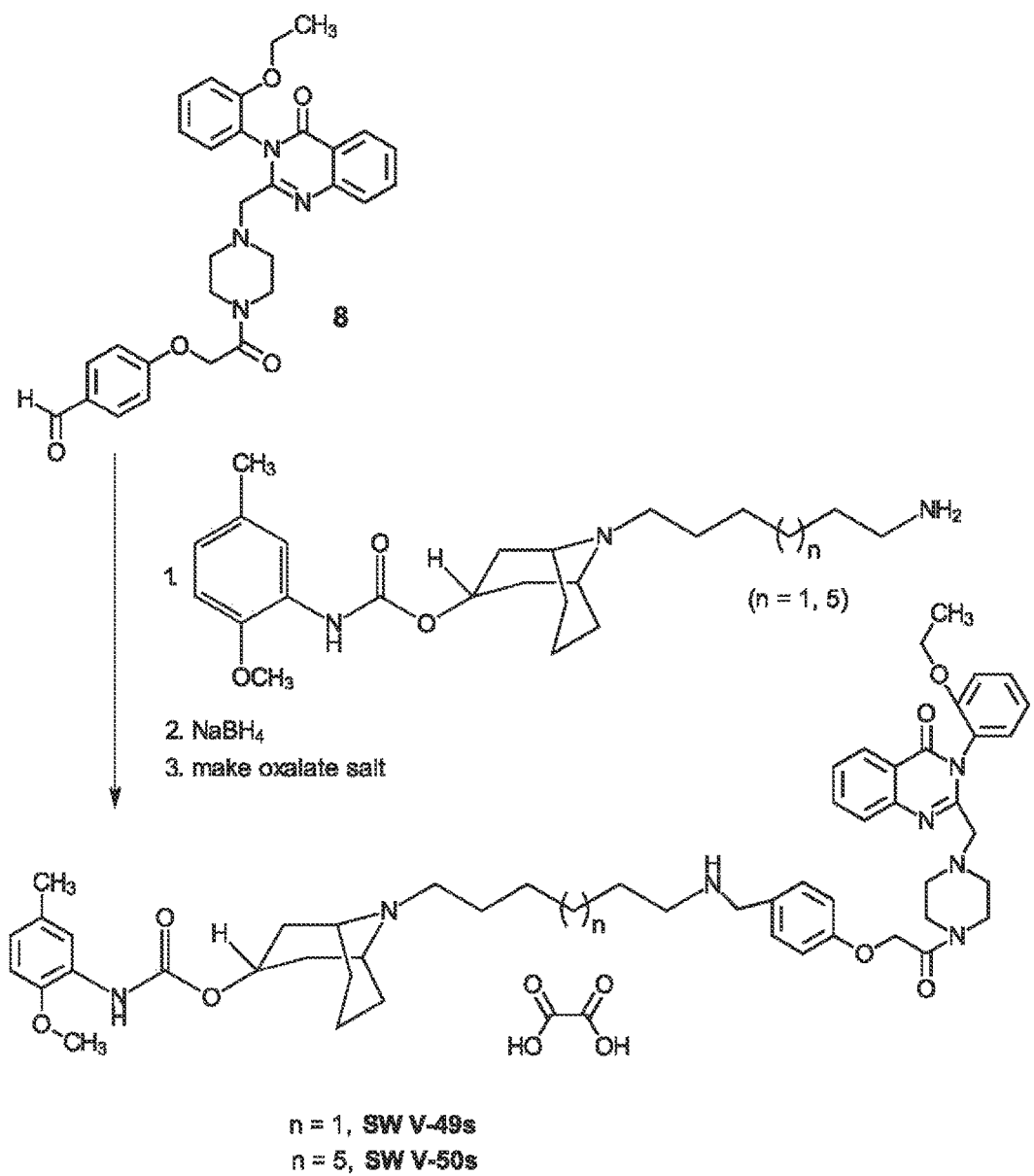
Figure 3:
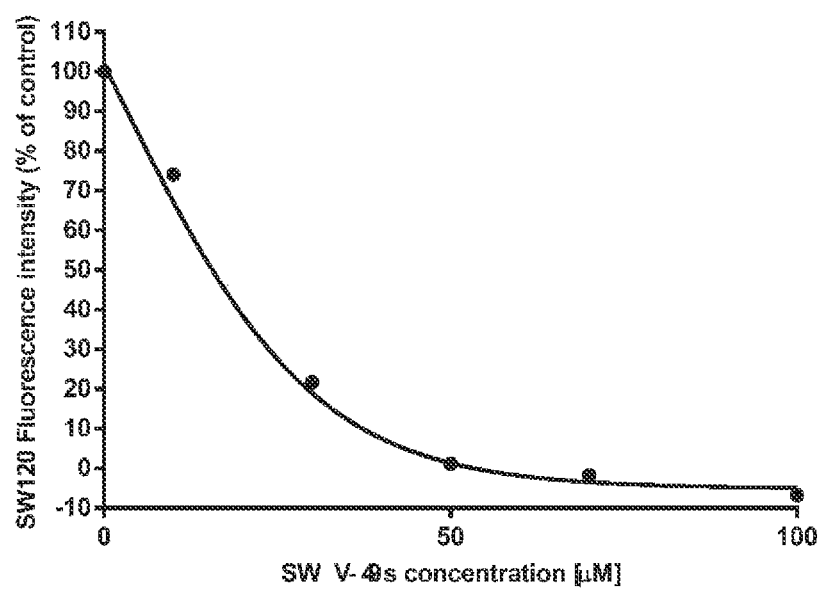

FIG. 3 illustrates competitive internalization inhibition of the fluorescent sigma-2 ligand SW 120 with SW V-49s by Pane-1 cells.

FIG. 4A-F illustrate viability assays of SW V-49s on various human (A-D) and murine (E) pancreatic cancer cell lines in vitro.

Figure 5A:
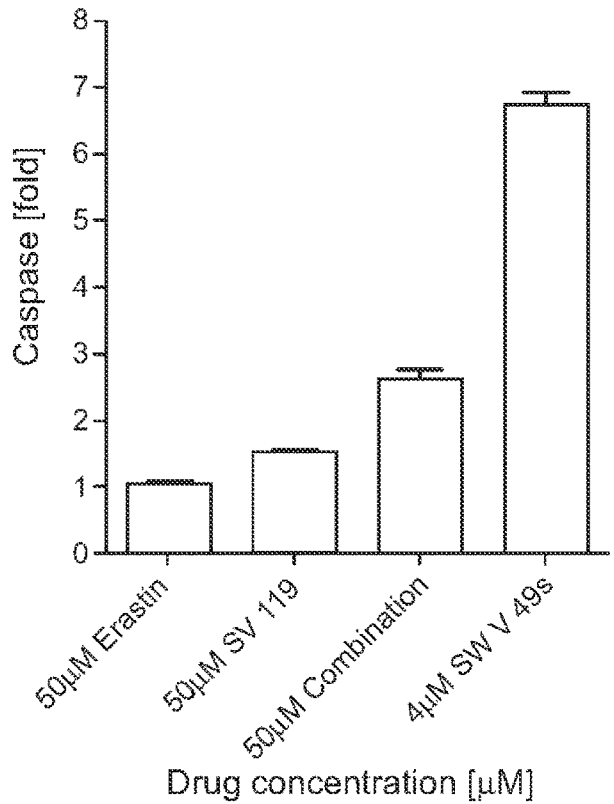
Figure 5B:
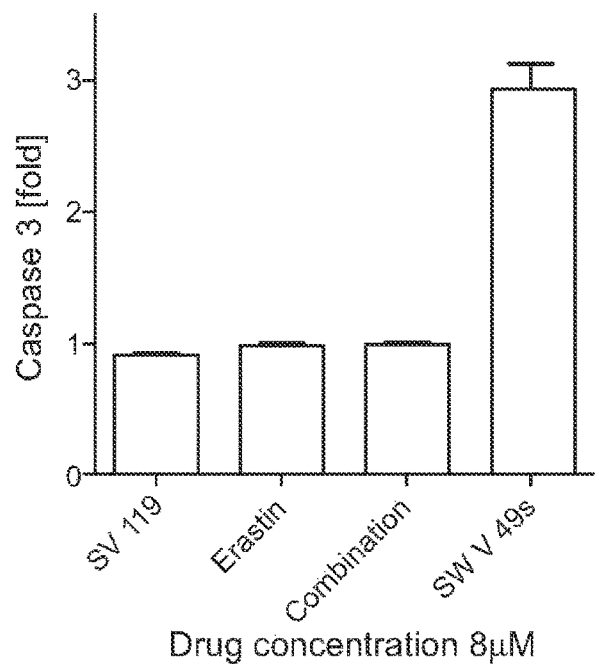

FIG. 5A-B illustrate increased apoptotic cell death induced by SW V-49s assayed after treatment for 24 hr. (A) or 7 hr. (B).

Figure 6:
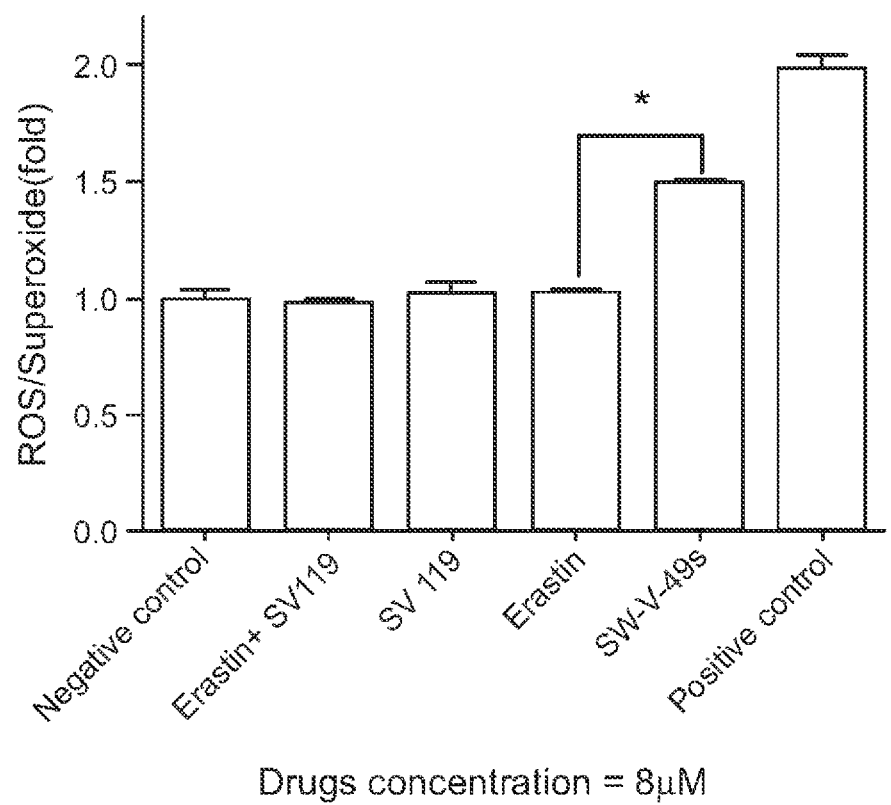

FIG. 6 illustrates ferroproptotic cell death induced by SW V-49s.

Figure 7:
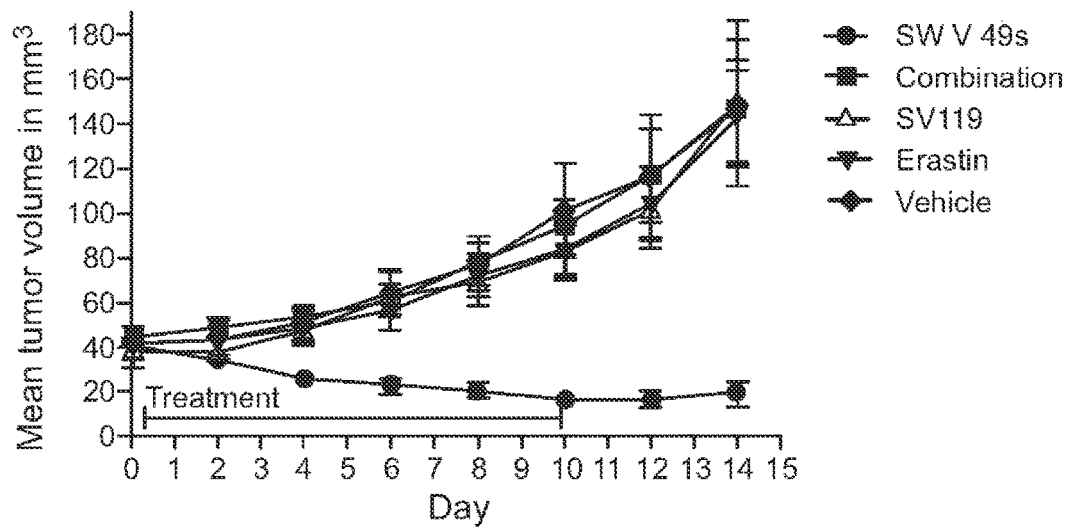

FIG. 7 illustrates decrease in tumor sizline in pancreatic cancer following SW V-49s administration in a murine model system.

Figure 8:
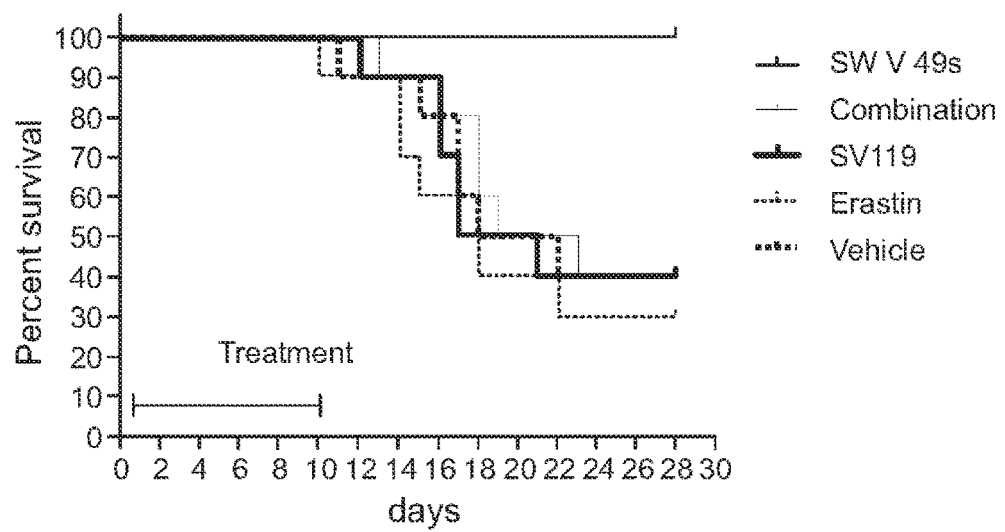

FIG. 8 illustrates 100% survival of pancreatic cancer following SW V-49s administration in a murine model system.

Figure 9:
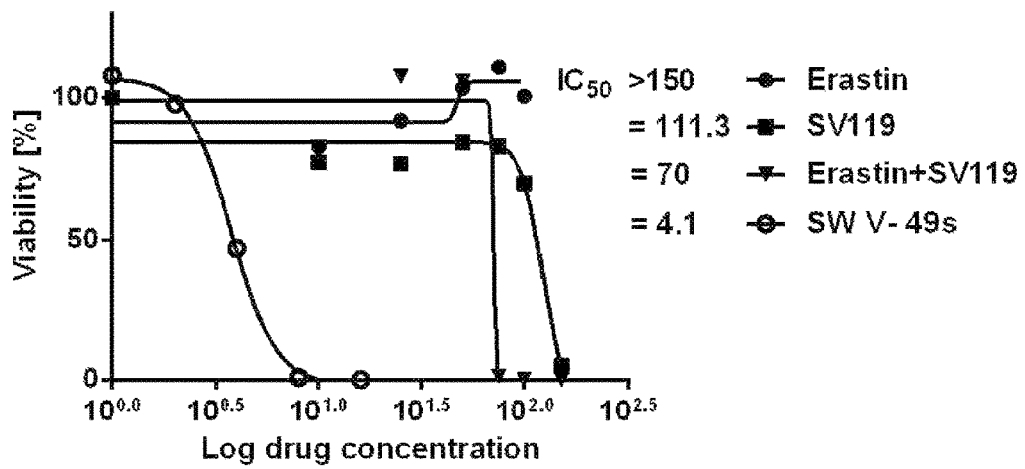

FIG. 9 illustrates the cell killing characteristics of SW V-49s and controls.

Figure 10:
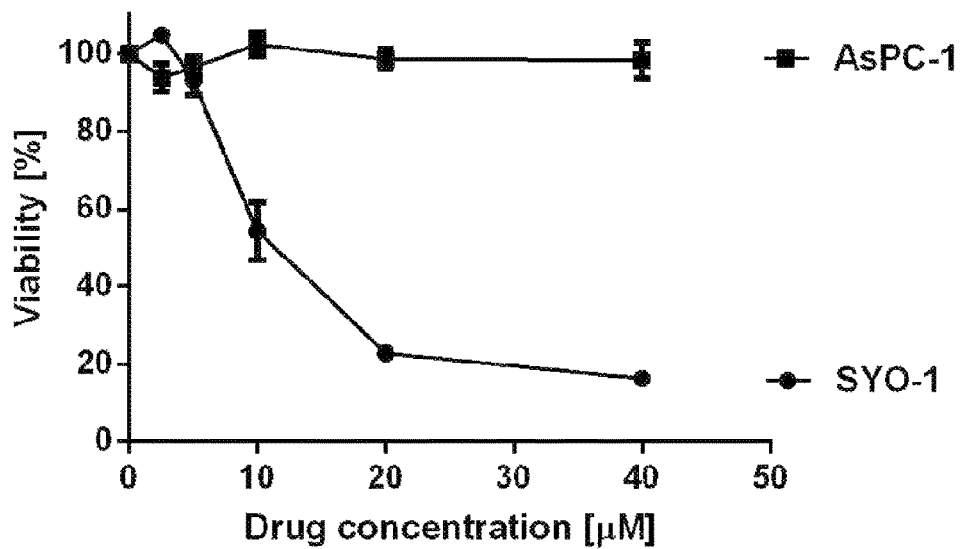

FIG. 10 illustrates a cell viability assay of cells treated with Erastin.

Figure 11A:
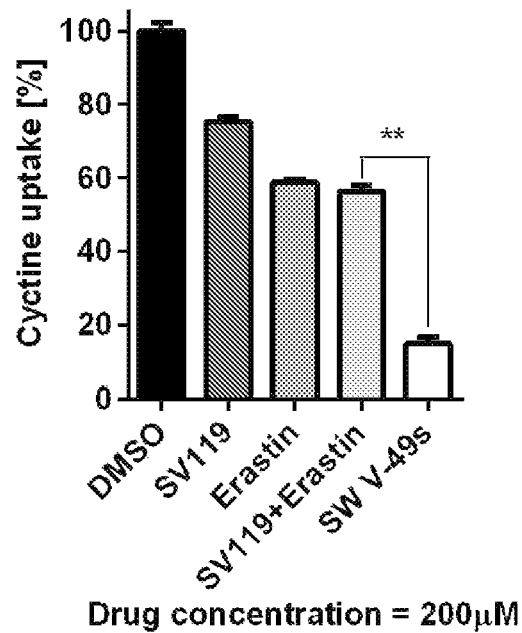
Figure 11B:
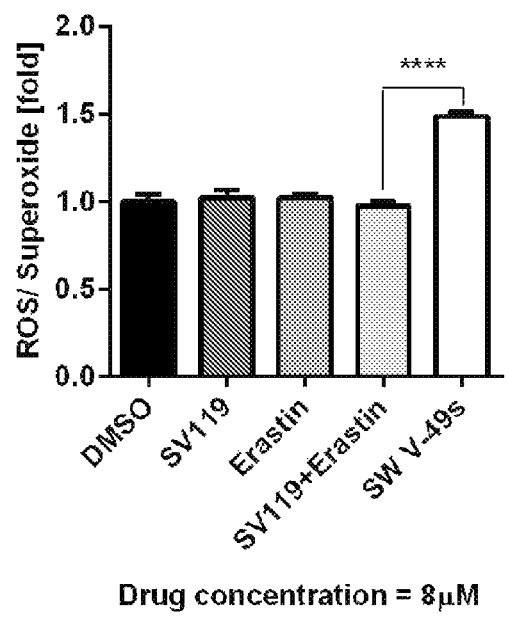

FIG. 11A-B illustrate that SW V-49s inhibits cystine uptake resulting in ROS generation.

Figure 12A:
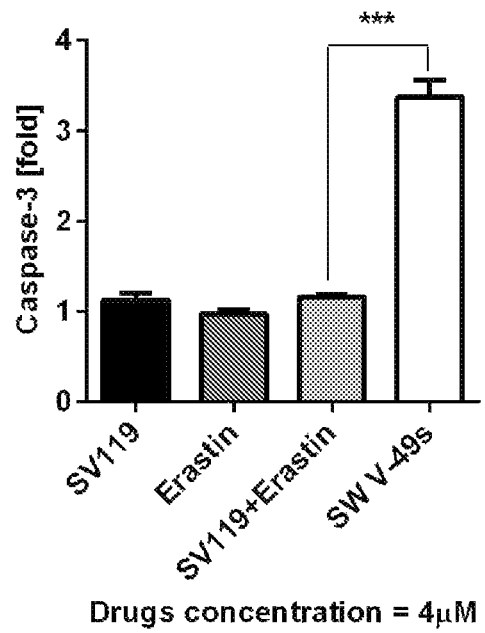
Figure 12B:
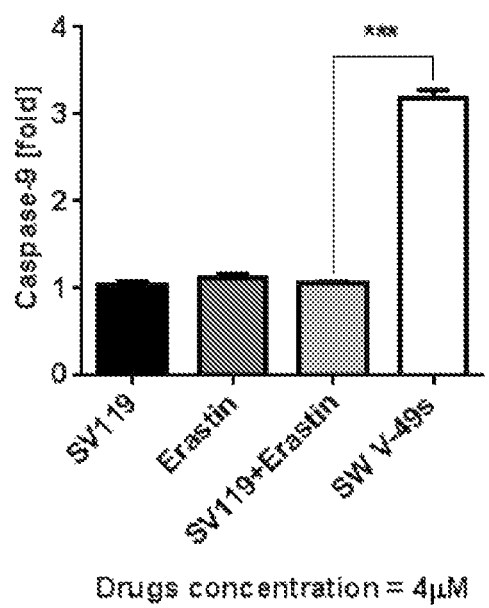
Figure 12C:
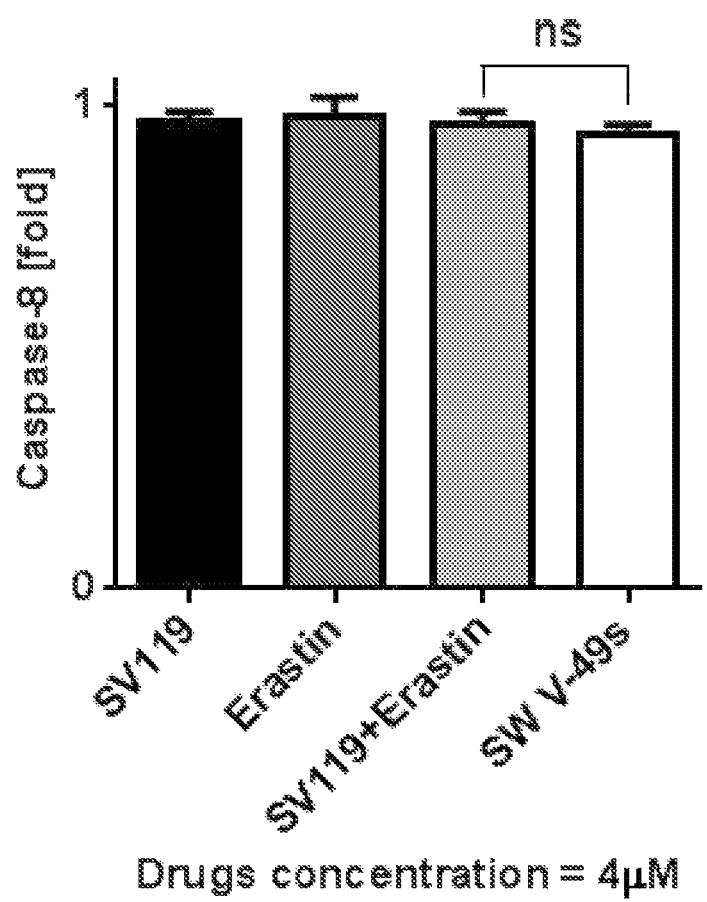

FIG. 12A-C illustrate that SW V-49s treatment induces intrinsic apoptotic pathway.

Figure 13:
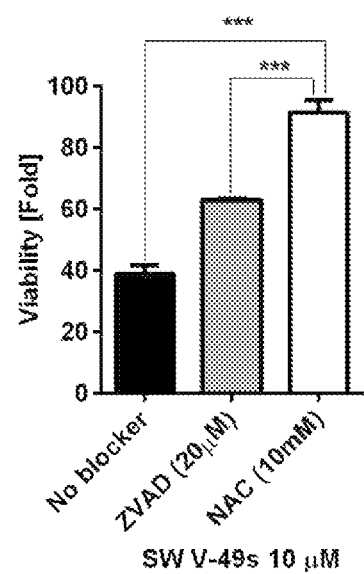

FIG. 13 illustrates that SW V-49s induces apoptotic and ROS dependent cell death.

FIG. 14A-E illustrate that SW V49s reduces tumor growth and enhances survival.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements.

Chemical species and moieties are named in accordance with *Naming and Indexing of Chemical Substances for Chemical Abstracts™ 2007 Edition*, American Chemical Society, 2008, except as specified below.

The term "lower," as used herein, alone or in a combination, where not otherwise specifically defined, means containing from 1 up to and including 6 carbon atoms.

The term "lower aryl," as used herein, alone or in combination, means phenyl or naphthyl, either of which can be optionally substituted as provided.

The term "lower heteroaryl," as used herein, alone or in combination, means either 1) monocyclic heteroaryl comprising five or six ring members, of which between one and four the members can be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls can be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four can be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls can be unsaturated.

The term "lower amino," as used herein, alone or in combination, refers to —NRR', wherein R and R' are independently selected from the group consisting of hydrogen, alkyl, and lower heteroalkyl, any of which can be optionally substituted. Additionally, the R and R' of a lower amino group can combine to form a five- or six-membered heterocycloalkyl, either of which can be optionally substituted.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate", "sulfonic acid," and "sulfonic," as used herein, alone or in combination, refer to the —SO$_3$H group and its anion as the sulfonic acid as used in salt formation.

The term "sulfanyl," as used herein, alone or in combination, refers to —S—.

The term "sulfinyl," as used herein, alone or in combination, refers to —S(O)—.

The term "N-sulfonamide" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocabamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyidimethylsilyl, triphenylsilyl and the like.

Any definition herein can be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the anteceding group can be substituted or unsubstituted. When substituted, the substituents of an "optionally substituted" group can include, without limitation, one or more substituents independently selected from the following groups or a particular designated set of groups, alone or in combination: alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, alkylcarbonyl, lower carboxyester, lower carboxamido, cyano, hydrogen, halogen, hydroxy, amino, alkylamino, arylamino, amido, nitro, thiol, alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety can be defined as needed; in these cases, the optional substitution will be as defined, often immediately following the phrase, "optionally substituted with."

The term R or the term R' appearing by itself and without a number designation, unless otherwise defined, refers to a moiety selected from the group consisting of hydrogen, alkyl, cycloalkyl, heteroalkyl, aryl, heteroaryl and heterocycloalkyl, any of which can be optionally substituted. Such R and R' groups should be understood to be optionally substituted as defined herein. Whether an R group has a number designation or not, every R group, including R. R' and Rn wherein n is an integer, every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups can be attached to a parent molecule or can occupy a position in a chain of elements from either end as written. Thus, by way of example only, an unsymmetrical group such as —C(O)N(R)— can be attached to the parent moiety at either the carbon or the nitrogen.

Asymmetric centers exist in the compounds disclosed herein. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein can exist as geometric isomers. Additionally, compounds can exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond can be single, double, or triple unless otherwise specified. A dashed line between two atoms in a drawing of a molecule indicates that an additional bond can be present or absent at that position.

The term "disease" as used herein is synonymous, and is used interchangeably with, the terms "disorder," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

In the present disclosure, the term "radiation" means ionizing radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces an increase in cell damage or death.

The term "radiation therapy" refers to the use of electromagnetic or particulate radiation in the treatment of neoplasia and includes the use of ionizing and non-ionizing radiation.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts can be of utility in the preparation and purification of the compound in question.

Basic addition salts can also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphtlialenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramelhylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Compounds

The present disclosure provides a compound of structural Formula I

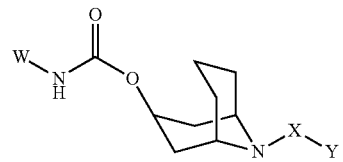

or a sail thereof, wherein: W is chosen from optionally substituted $C_5$-$C_{10}$ aryl and $C_5$-$C_{10}$ heteroaryl; X is a linking moiety; and Y is a ferroptosis-inducing moiety chosen from erastin, an erastin analog such as erastin-A, erastin-B. or desmethyl-erastin or a simplified synthetic erastin mimetic.

In some configurations, W can be a $C_5$-$C_{10}$ aryl.

In some configurations, W can be a substituted $C_5$-$C_{10}$ aryl.

In some configurations, W can be a sigma-2 receptor ligand.

In some configurations, the linking moiety can comprise a $C_1$-$C_{12}$ linear chain.

In some configurations, the linking moiety can further comprise 1 or more heteroatoms. In some configurations, each of the 1 or more heteroatoms can be independently selected from the group consisting of an oxygen, a sulfur, and a nitrogen.

In some configurations, the linking moiety can have a structure

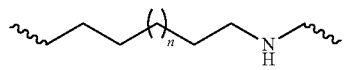

wherein ⌇ is a bond, and n is an integer from 1 to 10, i.e., 1, 2, 3, 4, 5, 6, 7, 8, 9 or 10, 9. In some configurations, n=1. In some configurations, n=5.

In some configurations, the ferroptosis-inducing moiety of a compound of the structural Formula I can be selected from the group consisting of erastin, erastin-A, erastin-B and desmethyl-erastin.

In some configurations, the ferroptosis-inducing moiety of a compound of the structural Formula I can be erastin.

In some embodiments, the present teachings include compounds of Formula II

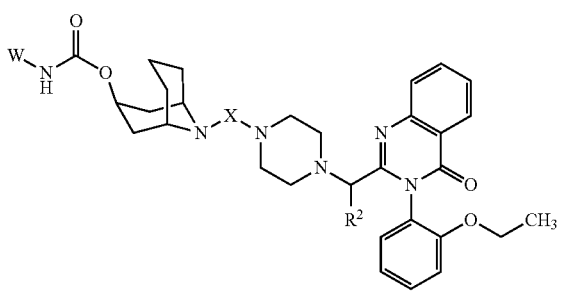

or a salt thereof, wherein: W is chosen from optionally substituted $C_5$-$C_{10}$ aryl and $C_5$-$C_{10}$ heteroaryl; X is a linking moiety; and $R^2$ is chosen from hydrogen and methyl.

In some embodiments, the present teachings include compounds of Formula III:

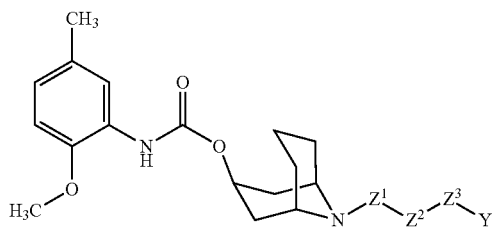

(III)

or a salt thereof, wherein: each of $Z^1$ and $Z^3$ is independently selected from the group consisting of a bond, $C_1$-$C_{10}$ alkyl, $C_1$-$C_{10}$ alkenyl, $C_1$-$C_{10}$ alkynyl, $C_5$-$C_{10}$ aryl, $C_5$-$C_{10}$ heteroaryl, arylalkyl, heteroarylalkyl, alkylaryl, alkylheteroaryl, heterocycloalkylalkyl, alkylheterocycloalkyl, cycloalkylalkyl, alkylcycloalkyl, —(CH$_2$)$_a$(OCH$_2$CH$_2$)$_b$(CH$_2$)$_c$—, —(CH$_2$)$_a$(CH$_2$CH$_2$O)$_b$(CH$_2$)$_c$—, —(CH$_2$)$_a$O(CH$_2$)$_c$—, —(CH$_2$)$_a$S(CH$_2$)$_c$—, —(CH$_2$)$_a$S(O)$_2$(CH$_2$)$_c$—, —(CH$_2$)$_a$S(O)(CH$_2$)$_c$—, —(CH$_2$)$_a$N(R$^1$)(CH$_2$)$_c$—, —(CH$_2$)$_a$ N(R$^1$)C(O)(CH$_2$)$_c$13 , —(CH$_2$)$_a$C(O)N(R$^1$)(CH$_2$)$_c$—, —(CH$_2$)$_a$N(R$^1$)C(O)N(R$^1$)(CH$_2$)$_c$—, —(CH$_2$)$_a$S(O)$_2$N(R$^1$)(CH$_2$)$_c$13 , —(CH$_2$)$_a$N(R)S(O)$_2$(CH$_2$)$_c$—, $Z^2$ is chosen from $C_1$-$C_{10}$ alkyl, $C_1$-$C_{10}$ alkenyl, $C_1$-$C_{10}$ alkynyl, $C_5$-$C_{10}$ aryl, $C_5$-$C_{10}$ heteroaryl, arylalkyl, heteroarylalkyl, alkylaryl, alkylheteroaryl, heterocycloalkylalkyl, alkylheterocycloalkyl, cycloalkylalkyl, alkylcycloalkyl, —(CH$_2$)$_a$(OCH$_2$CH$_2$)$_b$(CH$_2$)$_c$—, and —(CH$_2$)$_a$(CH$_2$CH$_2$O)$_b$(CH$_2$)$_c$—, —(CH$_2$)$_a$O(CH$_2$)$_c$—, —(CH$_2$)$_a$S(CH$_2$)$_c$—, —(CH$_2$)$_a$S(O)$_2$(CH$_2$)$_c$—, —(CH$_2$)$_a$S(O)(CH$_2$)$_c$—, —(CH$_2$)$_a$ N(R$^1$)(CH$_2$)$_c$—, —(CH$_2$)$_a$N(R$^1$)C(O)(CH$_2$)$_c$—, —(CH$_2$)$_a$C(O)N(R$^1$)(CH$_2$)$_c$—, —(CH$_2$)$_a$N(R$^1$)C(O)N(R$^1$)(CH$_2$)$_c$—, —(CH$_2$)$_a$S(O)$_2$N(R$^1$)(CH$_2$)$_c$—, —(CH$_2$)$_a$N(R)S(O)$_2$(CH$_2$)$_c$—; wherein each of $Z^1$, $Z^2$, and $Z^3$ can be optionally substituted with one or more groups chosen from halo, oxo, and $C_1$-$C_{10}$ alkyl; each $R^1$ is independently chosen from hydrogen, $C_1$-$C_{10}$ alkyl, and $C_1$-$C_{10}$ acyl; each a and c is an integer independently chosen from 0, 1, 2, 3, and 4; each b is an integer independently chosen from 1, 2, 3, 4, 5, and 6; and Y is a ferroptosis-inducing moiety chosen from erastin, an erastin analog such as erastin-A, erastin-B, or desmethyl-erastin or a simplified synthetic erastin mimetic.

In certain embodiments, a compound of the present teachings has structural Formula IV:

In some configurations, n can be 1; and $R^2$ can be hydrogen.

In some configurations, n can be 5; and $R^2$ can be hydrogen.

In some configurations, the salt can be an oxalate salt.

In some configurations, the compound can be chosen from compounds 1-24 as disclosed herein.

Pharmaceutical Compositions

While compounds of the present teachings can be administered as the raw chemical, it is also possible to present them as a pharmaceutical formulations. Accordingly, provided herein are pharmaceutical formulations which comprise one or more compounds of the present teachings, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in Remington's Pharmaceutical Sciences. The pharmaceutical compositions disclosed herein can be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route can depend upon for example the condition and disorder of the recipient. The formulations can conveniently be presented in unit dosage form and can be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active (IV)

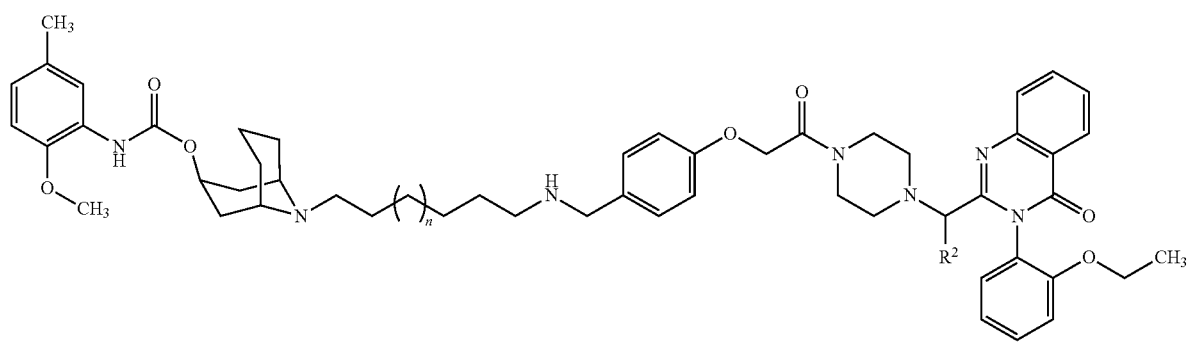

or a sail thereof, wherein: n is an integer chosen from 1, 2, 3, 4, and 5; and $R^2$ can be selected from hydrogen and methyl.

ingredient with liquid carriers or finely divided solid carriers or both and then, if necessary, shaping the product into the desired formulation.

Compounds described herein can be administered as follows:

Oral Administration

The compounds of the present teachings can be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present can be from about 0.05% to about 95% by weight, more typically from about 2% to about 50% by weight of the dosage form.

In addition, tablets or capsules can contain a disintegrant, comprising from about 0.5% to about 35% by weight, more typically from about 2% to about 25% of the dosage form. Examples of disintegrates include methyl cellulose, sodium or calcium carboxymethyl cellulose, croscarmellose sodium, polyvinylpyrrolidone, hydroxy propyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, can be present in amounts from about 0.1% to about 3% by weight, and include polysorbate 80, sodium dodecyl sulfate, talc and silicon dioxide.

Suitable lubricants, for use in a tablet or capsule, can be present in amounts from about 0.1% to about 5% by weight, and include calcium, zinc or magnesium stearate, sodium stearyl fumarate and the like.

Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surface active or dispersing agents. Molded tablets can be made by molding in a suitable machine a mixture of the powdered compound moistened with a liquid diluent. Dyes or pigments can be added to tablets for identification or to characterize different combinations of active compound doses.

Liquid formulations can include emulsions, solutions, syrups, elixirs and suspensions, which can be used in soft or hard capsules. Such formulations can include a pharmaceutically acceptable carrier, for example, water, ethanol, polyethylene glycol, cellulose, or an oil. The formulation can also include one or more emulsifying agents and/or suspending agents.

Compositions for oral administration can be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present teachings can be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle und needle-free injectors) and infusion methods. The formulations can be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats preservatives, and solutes which render the formulation isotonic with the blood of the intended recipient, and carbohydrates.

Parenteral formulations can also be prepared in a dehydrated form (e.g., by lyophilization) or as sterile non-aqueous solutions. These formulations can be used with a suitable vehicle, such as sterile water. Solubility-enhancing agents can also be used in preparation of parenteral solutions.

Compositions for parenteral administration can be formulated as immediate or modified release, including delayed or sustained release. Compounds can also be formulated as depot preparations. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Topical Administration

In some configurations, compounds of the present teachings can be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration can comprise from 0.001% to 10% w/w (by weight) of the formulation. In certain embodiments, the active ingredient can comprise as much as 10% w/w; less than 5% w/w; from 2% w/w to 5% w/w; or from 0.1% to 1% w/w of the formulation.

Compositions for topical administration can be formulated as immediate or modified release, including delayed or sustained release.

Rectal, Buccal, and Sublingual Administration

Suppositories for rectal administration of the compounds of the present teachings can be prepared by mixing the active agent with a suitable non-irritating excipient such as cocoa butter, synthetic mono-, di- or triglycerides, fatty acids, or polyethylene glycols which are solid at ordinary temperatures but liquid at the rectal temperature, and which will therefore melt in the rectum and release the drug.

For buccal or sublingual administration, the compositions can take the form of tablets, lozenges, pastilles, or gels formulated in conventional manner. Such compositions can comprise the active ingredient in a flavored basis such as sucrose and acacia or tragacanth.

Administration by Inhalation

For administration by inhalation, in some configurations, compounds of the present teachings can be delivered from an insufflator, nebulizer pressurized packs or other convenient means of delivering an aerosol spray or powder. Pressurized packs can comprise a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Alternatively, for administration by inhalation or insufflation, the compounds according to the disclosure can take the form of a dry powder composition, for example a powder mix of the compound and a suitable powder base such as lactose or starch. The powder composition can be presented in unit dosage form, in for example, capsules, cartridges, gelatin or blister packs from which the powder can be administered with the aid of an inhalator or insufflator.

Other earner materials and modes of administration known in the pharmaceutical art can also be used. Pharmaceutical compositions of the teachings can be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration can vary depending on the condition and its severity. The above considerations concerning effective formulations and administration procedures are well known in the art and are described in standard textbooks. Formulation of drugs is discussed in, for example, Hoover. John E., Remington's Pharmaceutical Sciences, Mack Publishing Co., Easton, Pa., 1975; Liberman, et al., Eds., Pharmaceutical Dosage Forms, Marcel Decker, New York. N.Y., 1980; and Kibbe, et al., Eds., Handbook of Pharmaceutical Excipients ($3^{rd}$ Ed.), American Pharmaceutical Association, Washington, 1999.

Methods of Treatment

The present disclosure provides compounds and pharmaceutical compositions feature a targeting moiety which binds the sigma-2 receptor and can thus be useful in the treatment or prevention of disorders associated with cells that express the sigma-2 receptor and include, but are not limited to cancer.

Cancer

In some embodiments, the compounds and pharmaceutical compositions of the present disclosure can be useful in the treatment or prevention of cancer.

In certain embodiments, the cancer can be chosen from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, synovial sarcoma. T-cell lymphoma, testicular cancer, thyroid cancer, throat cancer, urogenital cancer, urothelial carcinoma, uterine cancer, vaginal cancer, or Wilms' tumor.

In particular embodiments, the cancer can be pancreatic cancer. In particular embodiments, the cancer can be synovial sarcoma.

Combinations and Combination Therapy

The compounds of the present teachings can be used, alone or in combination with other pharmaceutically active compounds, to treat conditions such as those previously described hereinabove. The compound(s) of the present teachings and other pharmaceutically active compound(s) can be administered simultaneously (either in the same dosage form or in separate dosage forms) or sequentially. Accordingly, in one embodiment, the present teachings comprises methods for treating a condition by administering to the subject a therapeutically-effective amount of one or more compounds of the present teachings and one or more additional pharmaceutically active compounds.

In another embodiment, there is provided a pharmaceutical composition comprising one or more compounds of the present teachings, one or more additional pharmaceutically active compounds, and a pharmaceutically acceptable carrier.

In another embodiment, tire one or more additional pharmaceutically active compounds is selected from the group consisting of anti-cancer drugs, anti-proliferative drugs, and anti-inflammatory drugs.

Sigma-2 receptor binding compositions described herein are also optionally used in combination with other therapeutic reagents that arc selected for their therapeutic value for the condition to be treated. In general, the compounds described herein and. in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a sigma-2 receptor binding compound, as described herein, in combination with another therapeutic agent. By way of example only, the therapeutic effectiveness of a sigma-2 receptor binding compound is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it can be appropriate to administer an agent, to reduce the side effect; or the therapeutic effectiveness of a compound described herein can be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a sigma-2 receptor binding compound as described herein) can be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment a sigma-2 receptor binding compound inhibitor is optionally used in combination with procedures that provide additional benefit to the patient. A sigma-2 receptor binding compound inhibitor and any additional therapies are optionally administered before, during or after the occurrence of a disease or condition, and the timing of administering the composition containing a sigma-2 receptor binding compound varies in some embodiments. Thus, for example, a sigma-2 receptor binding compound is used as a prophylactic and is administered continuously to subjects with a propensity to develop conditions or diseases in order to prevent the occurrence of the disease or condition. A sigma-2 receptor binding compound and compositions are optionally administered to a subject during or as soon as possible after the onset of the symptoms. While embodiments of the present teachings have been shown and described herein, it will be obvious to those skilled in the art that such embodiments are provided by way of example only. Numerous variations, changes, and substitutions can occur to those skilled in the art without departing from the teachings. In some embodiments of the present teachings, various alternatives to the embodiments described herein can be employed in practicing the present teachings.

A sigma-2 receptor binding compound can be used in combination with anti-cancer drugs, including but not limited to the following classes: alkylating agents, angiopoietin 1 and/or 2 inhibilosr, anthracyclines, antimetabolite agents, aurora kinase inhibitors, B-raf inhibitors, BTK inhibitors, c-met inhibitors, CDK 4 and/or 6 inhibitors, CDK4 and/or CDK6 inhibitors, cFMS inhibitors, crosslinking agents, DMA replication inhibitors, endothelial growth factor (EGF) inhibitors, hepatocyte growth factor/scatter factor (HGF/SF) inhibitors, HER2 and HER3 inhibitors insulin-like growth factor 1 receptor (IGFR-1) inhibitors, intercalators, MEK ihibitors, microtubule disrupters, mTOR inhibitors, pan-ErbB tyrosine kinase inhibitors, PARP inhibitors, P13K inhibitors, PKB inhibitors, PKB inhibitors, polo-like kinase inhibitors, radiomimetic agents, radiosensitizers, recombinant human apo2 ligands, strand break agents, topolsomerase II inhibitors, tumor necrosis factor-related apoptosis-inducing ligand (TRAIL) agonisst, and vascular endothelial growth factor (VEGF) inhibitors.

The compounds disclosed herein, including compounds of Formula I, are also useful as chemo- and radio-sensitizers for cancer treatment. They are useful for the treatment of mammals who have previously undergone or are presently undergoing or will be undergoing treatment for cancer. Such other treatments include chemotherapy, radiation therapy, surgery or immunotherapy, such as cancer vaccines.

The instant compounds are particularly useful in combination with therapeutic, anti-cancer and/or radiotherapeutic agents. Thus, the present disclosuredisclosure provides a combination of the presently compounds of Formula I with therapeutic, anti-cancer and/or radiotherapeutic agents for simultaneous, separate or sequential administration. The compounds of this disclosure and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

The therapeutic agent, anti-cancer agent and/or radiation therapy can be administered according to therapeutic protocols well known in the art. It will be apparent to those skilled in the art that the administration of the therapeutic agent, anti-cancer agent and/or radiation therapy can be varied depending on the disease being treated and the known effects of the anti-cancer agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-neoplastic agent or radiation) on the patient, and in view of the observed responses of the disease to the administered therapeutic agents, and observed adverse affects.

Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Any suitable means for delivering radiation to a tissue can be employed in the present disclosure. Common means of delivering radiation to a tissue is by an ionizing radiation source external to the body being treated. Alternative methods for delivering radiation to a tissue include, for example, first delivering in vivo a radiolabeled antibody that immunoreacts with an antigen of the tumor, followed by delivering in vivo an effective amount of the radio labeled antibody to the tumor. In addition, radioisotopes can be used to deliver ionizing radiation to a tissue or cell. Additionally, the radiation can be delivered by means of a radiomimetic agent. As used herein a "radiomimetic agent" is a chemotherapeutic agent, for example melphalan, that causes the same type of cellular damage as radiation therapy, but without the application of radiation.

For use in cancer and neoplastic diseases a sigma-2 receptor binding compound can be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLKRAN) and cyclophosphamide (ENDOXAN); (2) anti-metabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

The additional therapeutic agent can be chosen from 5-fluorouracil, adriamycin, afatinib, alemtuzmab, altretamine, aminoglutethimide, aminolevulinic acid, amsacrine, anastrozole, aprepitant, asparaginase, axitinib, azacitidine, beg, bertozimib, bevacizumab, bexarotene, bicalutamide, bleomycin, bortezomib, bosutinib, buserelin, busulfan, campothecin, capecitabine, carboplatin, carbozantimib, carfilzomib, carmustine, ceritinib, cetuximab, chlorambucil, chloroquine, cisplatin, cladisat, aq. NaCl solution, cladribine, clodronate, clofarabine, cobimetinib, colchicine, crizotinib, cyclophosphamide, cyclophosphamine, cyproterone, cytarabine, dacarbazine, dactinomycin, dasatinib, daunorubicin, debrafinib, decarazine, decitabine, demethoxyviridin, desatinib, dexrazoxane, dichloroacetate, dienestrol, diethylstilbestrol, docetaxel, doxorubicin, enzalutamide, epirubicin, erlotinib, estradiol, estramustine, etoposide, everolimus, exemestane, filgrastim, fludarabine, fludrocortisone, fluorouracil, fluoxymesterone, flutamide, fulvestrant, gefitinib, gemcitabine, gemtuzumab, genistein, goserelin, hydroxyurea, ibrutanib, idarubicin, idelalisib, ifosfamide, imatinib, imiquimod, interferon, irinotecan, ironotecan, ixabepilone, lapatinib, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate,methotrexate, mithram, mitomycin, mitosmycin, mitotane, mitoxane, mitoxantrone, nelarabine, neratinib, nilotinib, nilutamide, nocodazole, octreotide, olaparib, oxaliplatin, paclitaxel, pamidronate, pazopanib, pegaspargase, pemetrexed, pemostatin, perifosine, plicamycin, pomalidomide, ponatinib, porfimer, procarbazine, raloxifene, raltitrexed, regorafinib, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, vinorelbine, volasertib, vorinostat, and zoledronic acid Where a subject is suffering from or at risk of suffering from an inflammatory condition, a sigma-2 receptor binding compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) non-steroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

Compound Synthesis

Compounds of the present teachings can be prepared using methods illustrated in general synthetic schemes and experimental procedures detailed below. General synthetic schemes and experimental procedures are presented for purposes of illustration and are not intended to be limiting. Starting materials used to prepare compounds of the present teachings are commercially available or can be prepared using routine methods known in the art.

List of Abbreviations aq.=aqueous; $CDCl_3$=deuterated chloroform; DMSO-$d_6$=deuterated dimethyl sulfoxide; DMSO=dimethyl sulfoxide; h=hour; THF=tetrahydrofuran.

Some embodiments of the present teachings include methods of synthesis of compounds of Formula IV:

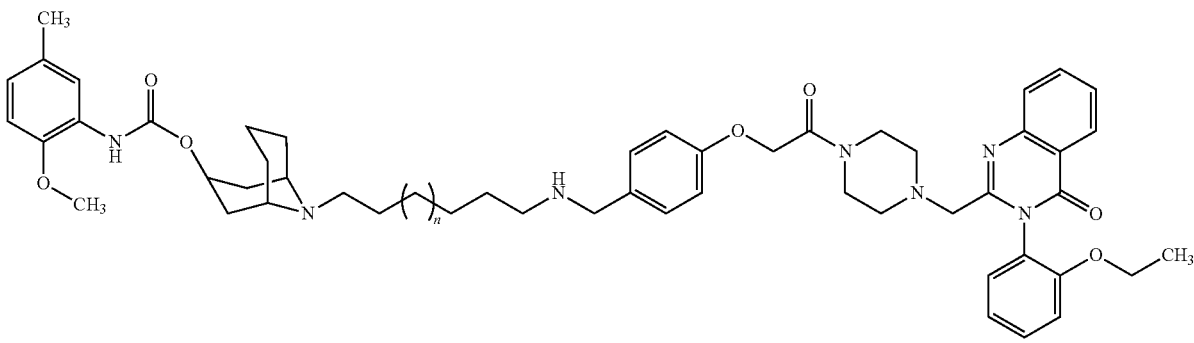

(IV). In various configurations, these methods comprise reacting a compound of structural Formula V:

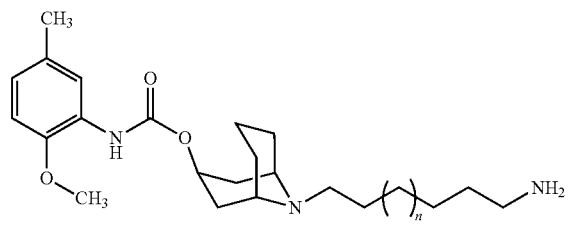

with a compound of structural formula VI:

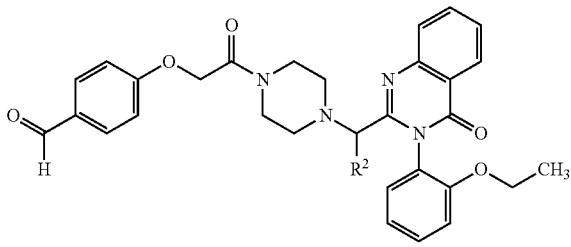

wherein n is an integer from 1 to 5, and $R^2$ is hydrogen or methyl.

In some configurations, n can be 1; and $R^2$ can be hydrogen.

In some configurations, n can be 5; and $R^2$ can be hydrogen.

In some configurations, the reaction can take place in the presence of a reducing agent, such as, without limitation, aluminum hydride, borane-tetrahydrofuran, catecholborane, diisobutylaluminum hydride, disiamylborane, hydrazine, lithium aluminum hydride, lithium borohydride, lithium tri-t-butoxyaluminum hydride, lithium triethylborohydride, potassium tri-s-butylborohydride, sodium borohydride, sodium cyanoborohydride, sodium triacetoxyborohydride, or mixtures thereof.

General Methods for Preparing Compounds

The following schemes can be used to practice synthetic methods of the present teachings. Additional structural groups, including but not limited to those defined elsewhere in the specification and not shown in the compounds described in the schemes can be incorporated to give various compounds disclosed herein, or intermediate compounds which can, after further manipulations using techniques known to those skilled in the art, be converted to compounds of the present teachings.

EXAMPLE 1

3-(o-Ethoxyphenyl)-2-{[4-(2-{p-[(6-{3-(2-methoxy-toluidinocarbonyloxy)-9-azabicyclo[3.3,1]non-9-yl}hexylamino)methyl]phenoxy}acetyl)-1-piperazinyl]methyl}-3H-quinazolin-4-one) (SW V-49s)

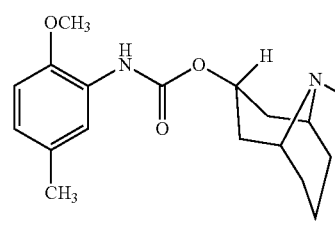
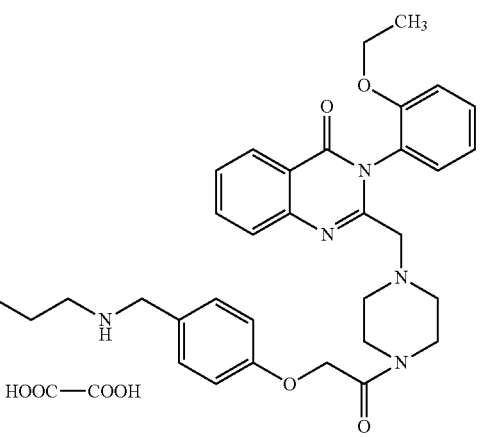

Intermediate 1A

N-9-Benzyl-9-azabicyclo[3.3.1]nonan-3α-ol (2)

A mixture of LiAlH(o-tert-Bu)$_3$ (20.0 g, 78.5 mmol) in anhydrous THF (30 mL) was cooled in an ice-bath. A solution of compound 9-azabicyclo[3.3.1]nonan-3-one (1) (5.0 g, 21.8 mmol) in anhydrous THF (45 mL) was added drop wise. The mixture was stirred at room temperature overnight. The reaction was quenched with saturated aqueous NH$_4$Cl. The solid was filtered off and washed with THF. The combined organic layers were dried over Na$_2$SO$_4$, filtered and evaporated to dryness to give N-9-Benzyl-9-azabicyclo[3.3.1]nonan-3α-ol as a light yellow oil (4.8 g, 95% yield). $^1$H NMR (CDCl$_3$) δ 7.20-7.35 (m, 5H), 4.22-4.32 (m, 1H), 3.79 (s, 2H), 3.02-3.06 (m, 2H), 2.33-2.43 (m, 2H), 2.12-2.26 (m, 1H), 1.85-1.99 (m, 3H), 1.30-1.54 (m, 3H), 1.08-1.13 (m, 2H).

Intermediate 1B

N-(9-Benzyl-9-azabicyclo[3.3.1]nonan-3α-yl)-N'-(2-methoxy-5-methyl-phenyl)carbamate (3)

A mixture of Intermediate 1A (4.8 g, 20.6 mmol), 2-methoxy-5-methylphenyl isocyanate (3.8 g, 23.5 mmol), dibutyltin diacetate (a few drops) in CH$_2$Cl$_2$ (45 mL) was stirred at room temperature overnight. The reaction mixture was washed with water, saturated aqueous NaHCO$_3$ and brine, and then dried over Na$_2$SO$_4$. The solvent was removed under reduced pressure and the residue was purified by silica gel column chromatography (hexane/ethyl acetate/triethylamine, 80:20:1) to obtain N-(9-Benzyl-9-azabicyclo[3.3.1]-nonan-3α-yl)-N'-(2-methoxy-5-methyl-phenyl)carbamate as a white solid (6.8 g, 83% yield). $^1$H NMR (CDCl$_3$) δ 7.97 (s, 1H), 7.16-7.37 (m, 6H), 6.73-6.80 (m, 2H), 5.22-5.30 (m, 1H), 3.84 (s, 3H), 3.81 (s, 2H), 3.04-3.07 (m, 2H), 2.42-2.52 (m, 2H), 2.30 (s, 3H), 1.91-2.20 (m, 3H), 1.48-1.56 (m, 3H), 1.15-1.18 (m, 2H).

Intermediate 1C

O-(9-Azabicyclo[3.3.1]nonan-3α-yl)-N-(2-methoxy-5-methylphenyl)-car-bamate (4)

To a solution of Intermediate 1B (6.8 g, 17.3 mmol) in methanol/ethyl acetate (1:1, 160 mL) was added 20% w/w Palladium hydroxide/carbon (1.35 g) and ammonium formate (5.4 g, 86.5 mmol). The mixture was refluxed for 6 h, cooled, filtered through a pad of celite and evaporated. The resulting residue was dissolved in ethyl acetate, washed with saturated aqueous NaHCO$_3$, water and brine, and then dries over Na$_2$SO$_4$. The solvent was removed to give the deprotected bicyclic amine O-(9-Azabicyclo[3.3.1]nonan-3α-yl)-N-(2-methoxy-5-methylphenyl)-carbamate 4 as a light brown oil (quantitative). $^1$H NMR (CDCl$_3$) δ 7.94 (s, 1H), 7.16 (s, 1H), 6.73-6.80 (m, 2H), 4.96-5.04 (m, 1H), 3.84 (s, 3H), 3.33-3.36 (m, 2H), 2.33-2.41 (m, 2H), 2.30 (s, 3H), 2.06-2.14 (m, 1H), 1.45-1.75 (m, 8H).

Intermediate 1D

N-(9-(6-aminohexyl)-9-azabicyclo[3.3.1]nonan-3α-yl)-N'-(2-methoxy-5-methyl-phenyl)carbamate (6a)

A mixture of secondary amine from Intermediate 1C (3.3 g. 11.0 mmol), N-(6-bromohexyl)phthalimide (3.5 g, 11.3 mmol), KI (2.0 g, 12.4 mmol) and K$_2$CO$_3$ (7.8 g, 56.5 mmol) in acetonitrile (90 mL) was stirred at reflux overnight. After filtration, volatile components were evaporated in vacuo. The resulting residue was purified by silica gel column chromatography (5% methanol in dichloromethane) to give the desired intermediate phthalimido-protected amine 5a (5.8 g, 96% yield) as a light brown oil.

Compound 5a (2.8 g, 5.3 mmol) was refluxed with hydrazine hydrate (540 mg, 10.7 mmol) in ethanol (100 mL) for 5 h. The solvent was evaporated and 10% aqueous solution of NaOH (20 mL) was added. The mixture was extracted with CH$_2$Cl$_2$, dried over Na$_2$SO$_4$, and evaporated to give the desired primary amine N-(9-(6-aminohexyl)-9-azabicyclo[3.3.1]nonan-3α-yl)-N'-(2-methoxy-5-methylphenyl) carbamate 6a (1.9 g, 88% yield) as a light yellow oil. $^1$H NMR (CDCl$_3$) δ 7.96 (s, 1H), 7.14 (s, 1H), 6.72-6.80 (m, 2H), 5.10-5.18 (m, 1H), 3.84 (s, 3H), 3.05-3.07 (m, 2H), 2.66-2.71 (m, 2H), 2.55-2.59 (m, 2H), 2.39-2.49 (m, 2H), 2.29 (s, 3H), 2.10-2.20 (m, 1H), 1.81-1.94 (m, 2H), 1.18-1.54 (m, 15H).

Intermediate 1E

Ethyl 2-(4-formylphenoxy)acetate (7)

Ethyl 2-bromoacetate (3.7 g, 22.0 mmol)) and potassium carbonate (8.3 g, 60.0 mmol) were added into the solution of 4-hydroxybenzaldehyde (2.4 g, 20.0 mmol) in acetonitrile (60 mL). The reaction mixture was refluxed for 24 h. After cooling, the reaction mixture was filtered, and evaporated to give ethyl 2-(4-formylphenoxy)acetate as a light yellow liquid (quantitative). $^1$H NMR (CDCl$_3$) δ 9.90 (s, 1H), 7.85 (d, J=8.4 Hz, 2H), 7.01 (d, J=8.4 Hz, 2H), 4.71 (s, 2H), 4.28 (q, J=7.1 Hz, 2H), 1.31 (t, J=7.1 Hz, 3H).

Intermediate 1F

2-(4-Formylphenoxy)acetic acid (8)

Hydrolysis of Intermediate 1E with sodium hydroxide (2.2 eq) in methanol/water (2:1, 90 mL) for 24 h, followed by acidifying with 10% HCl solution gave 2-(4-Formylphenoxy)acetic acid as an off-white solid (3.1 g, 87% yield). $^1$H NMR (DMSO-d$_6$) δ 13.18 (br s, 1H), 9.91 (s, 1H), 7.89 (d, 8.6 Hz, 2H), 7.13 (d, J=8.6 Hz, 2H), 4.86 (s, 2H).

Intermediate 1G

2-(2-Chloroacetamido)benzoic acid (9)

Triethylamine (4.06 g, 40.1 mmol) was added in the solution of 2-aminobenzoic acid (5.0 g, 36.5 mmol) in dichloromethane (90 mL) and the mixture was cooled in an ice-water bath, A solution of chloroacetyl chloride (4.5 g, 40.1 mmol) in dichloromethane (40 mL) was added drop wise and the mixture was allowed to stir at ambient temperature overnight. The solids were filtered and washed with cold water followed by 5% diethyl ether in hexane and were air dried to afford 2-(2-chloroacetamido)benzoic acid as a white solid (7.4 g, 95% yield). $^1$H NMR (DMSO-d$_6$) δ 11.82 (s, 1H), 8.52 (d, J=7.5 Hz, 1H), 8.01 (d, J=7.5 Hz, 1H), 7.63 (t, J=7.5 Hz, 1H), 7.21 (t, J=7.5 Hz, 1H), 4.45 (s, 2H).

Intermediate 1H

2-(Chloromethyl)-3-(2-ethoxyphenyl)quinazolin-4(3H)-one (10)

Phosphoryl chloride (6.5 g, 42.4 mmol) was added drop wise to a mixture of Intermediate 1G (3.1 g, 14.5 mmol) and 2-ethoxyaniline (2.0 g, 14.5 mmol) in acetonitrile (50 mL), The mixture was heated at reflux overnight. The reaction mixture was cooled to room temperature, poured into a slurry of ice/saturated solution of Na$_2$CO$_3$. The resulting solid was filtered, washed with water and air dried to give 2-(chloromethyl)-3-(2-ethoxyphenyl)quinazolin-4(3H)-one (10) as a brown solid (2.5 g, 53% yield). $^1$H NMR (CDCl$_3$) δ 8.31 (d, J=7.8 Hz, 1H), 7.78-7.82 (m, 2H), 7.47-7.55 (m, 2H), 7.35 (d, J=7.4 Hz, 1H), 7.06-7.14 (m, 2H), 4.35 (d, J=11.9 Hz, 1H), 4.17 (d, J=11.9 Hz, 1H), 4.06 (q, J=6.9 Hz, 2H), 1.23 (t, J=6.9 Hz, 3H).

Intermediate 11

3-(2-Ethoxyphenyl)-2-(piperdzin-1-yl-methyl)quinazolin-4(3H)-one (11)

Piperazine (2.7 g, 32.0 mmol) was added to a mixture of Intermediate 1H (2.5 g, 8.0 mmol), K$_2$CO$_3$ (4.4 g, 32.0 mmol) and KI (1.7 g, 10.4 mmol) in acetonitrile (75 mL). The reaction mixture was heated at 85-90° C. overnight. After cooling, it was filtered and the solid was washed with acetonitrile. The combined organic layers were evaporated. The resulting residue was dispersed in water and extracted with ethyl acetate. The organic layers were washed with brine, dried over Na$_2$SO$_4$, filtered and evaporated. The crude residue was purified by column chromatography (10% methanol, 0.5% NH$_4$OH in dichloromethane) to give 3-(2-ethoxyphenyl)-2-(piperazin-1-yl-methyl)quinazolin-4(3H)-one as a yellow oil (2.3 g, 79% yield). $^1$H NMR (CDCl$_3$) δ 8.30 (d, J=7.8 Hz, 1H), 7.75-7.77 (m, 2H), 7.39-7.50(m, 2H), 7.28 (d, J=7.0 Hz, 1H), 7.01-7.08 (m, 2H), 4.05 (q, J=6.8 Hz,2H), 3.18-3.28 (m, 2H), 2.73 (s, 4H), 2.33-2.37 (m, 2H), 2.17-2.20 (m, 2H), 1.22 (t, J=6.8 Hz, 3H).

Intermediate 1J 4-(2-(4-((3-(2-Ethoxyphenyl)-4-oxo-3,4-dihydroquinazolin-2-yl)methyl)-pip-erazin-1 -yl)-2-oxoethoxy) benzaldehyde (12)

A cooled mixture of acid 8 (360 mg, 2.0 mmol), N-hydroxysuccinimide (280 mg, 2.4 mmol) in acetonitrile (12 mL) was added a solution of DCC (500 mg, 2.4 mmol) in acetonitrile (4 mL). After stirring at room temperature for 45 min, a solution of Intermediate 11 (800 mg, 2.2 mmol) in acetonitrile (10 mL) was added, then continued stirring overnight. The solid was filtered off and the filtrate was evaporated. The resulting residue was purified by column chromatography (8% methanol in dichloromethane) to give 4-(2-(4-((3-(2-Ethoxyphenyl)-4-oxo-3,4-dihydroquinazolin-2-yl)methyl)-pip-erazin-1-yl)-2-oxo-ethoxy)benzaldehyde as an off-white solid (847 mg, 80% yield). $^1$H NMR (CDCl$_3$) δ 9.89 (s, 1H), 8.27-8.31 (m, 1H), 7.72-7.84 (m, 4H), 7.42-7.52 (m, 2H), 7.25 (d, J=6.3 Hz, 1H), 7.02-7.09 (m, 4H) 4.74 (s, 2H), 4.05 (q, J=7.0 Hz, 2H), 3.42-3.49 (m, 4H), 3.22-3.31 (m, 2H), 2.18-2.46 (m, 4H), 1.22 (t, J=7.0 Hz, 3H).

9-(6-(((4-(2-(4-((3-(2-Ethoxyphenyl-4-oxo-3,4-dihydroquinazolin-2-yl)methyl)-pip-erazin-1-yl)-2-oxoethoxy)benzyl)amino)hexyl)-N-(9-azabicyclo [3.3.1]nonan-3α-yl)-N-(2-methoxy-5-methylphenyl) carbamate oxalate salt (SW V-49s)

A solution of amine Intermediate 1D (6a) (386 mg, 0.95 mmol) in dichloromethane (4 mL) was added into a solution of Intermediate 1J (12) (480 mg, 0.91 mmol) in dichloromethane (4 mL). The mixture was stirred for 4 h then the solvent was evaporated. The residue was dissolved in ethanol (5 mL), then NaBH$_4$ (100 mg, 2.6 mmol) was added. The mixture was stirred few 6 h, then quenched with 10% HCl solution. After the solvent was evaporated, it was basified with 10% NaOH solution, extracted with dichloromethane and evaporated. The resulting residue was purified by column chromatography (10% methanol, 0.5% NH$_4$OH in dichloromethane) to give the product as free amine (460 mg, 55% yield). $^1$H NMR (CDCl$_3$) δ 8.30 (d, J=7.8 Hz, 1H), 7.94 (s, 1H), 7.74-7.78 (m, 2H), 7.41-7.51 (m, 2H), 7.23-7.26 (m, 3H), 7.14 (s, 1H), 7.03-7.09 (m, 2H), 6.86 (d, J=8.6 Hz, 2H), 6.73-6.79 (m, 2H), 5.10-5.16 (m, 1H), 4.62 (s, 2H), 4.04 (q, J=6.9 Hz, 2H), 3.85 (s, 3H), 3.74 (s, 2H), 3.43-3.48 (m, 4H), 3.22-3.30 (m, 2H), 3.12 (br s; 2H), 2.60-2.64 (m, 4H), 2.37-2.50 (m, 4H), 2.29 (s, 3H), 2.19-2.25 (m, 3H), 1.90-1.96 (m, 2H), 1.48-1.58 (m, 7H), 1.28-1.34 (m, 6H), 1.22 (t, J=6.9 Hz, 3H). The oxalate salt was prepared using 1 equivalent of oxalic acid in ethanol to give SW V-49s as an off-white solid (470 mg, 93% yield), mp 164-165° C. Anal. (C$_{55}$H$_{69}$N$_7$O$_{11}$·2H$_2$O): Calculated, %: C, 63.51: H, 7.07; N, 9.43, Found, %: C, 63.54, H, 7.06, N, 9.76.

EXAMPLE 2

3-(o-Ethoxyphenyl)-2-{[4-(2-{p-[(10-{3-(2-methoxytoluidinocarbonyloxy)-9-azabicyclo[3.3.1] non-9-yl}decylamino)methyl]phenoxy}acetyl)-1-piperazinyl]methyl}-3H-quinazolin-4-one) oxalate salt. (SW V-50s)

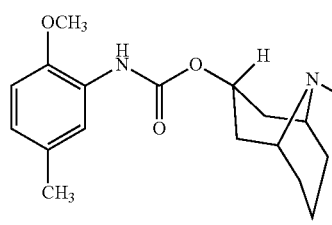
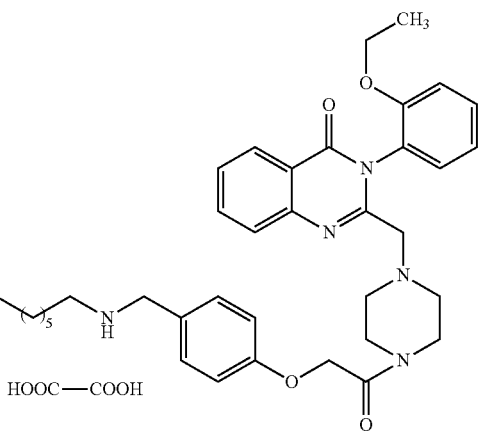

Intermediate 2A

N-(9-(10-aminodecyl)-9-azabicyclo[3.3.1]nonan-3α-yl-(2-methoxy-5-methylhenyl) carbamate (6b)

A mixture of secondary amine from Intermediate 1C (3.6 g, 11.8 mmol), N-(10-bromodecyl)phthalimide (4.4 g, 12.0 mmol), KI (2.0 g, 12.4 mmol) and $K_2CO_3$ (8.2 g, 59.4 mmol) in acetonitrile (90 mL) was stirred at reflux overnight. After filtration, volatile components were evaporated in vacuo. The resulting residue was purified by silica gel column chromatography (5% methanol in dichloromethane) to give the desired phthalimido-protected intermediate 5b (6.0 g, 86% yield) as a light brown oil.

Compound 5b (2.9 g, 4.9 mmol) was refluxed with hydrazine hydrate (700 mg, 13.9 mmol) in ethanol (100 mL) for 5 h. The solvent was evaporated and 10% aqueous solution of NaOH (20 mL) was added. The mixture was extracted with $CH_2Cl_2$, dried over $Na_2SO_4$, and evaporated to give the primary amine N-(9-(10-aminodecyl)-9-azabicyclo[3.3.1]nonan-3α-yl)-N'-(2-methoxy-5-methylphenyl) carbamate 6b (2.2 g, 95% yield) as a light yellow oil. $^1$H NMR (CDCl$_3$) δ 7.96 (s, 1H), 7.14 (s, 1H), 6.72-6.80 (m, 2H), 5.10-5.18 (m, 1H), 3.84 (s, 3H), 3.04-3.07 (m, 2H), 2.65-2.70 (m, 2H), 2.53-2.58 (m, 2H), 2.39-2.49 (m, 2H), 2.29 (s, 3H), 2.08-2.20 (m, 1H), 1.83-1.94 (m, 2H), 1.18-1.54 (m, 23H).

A solution of amine Intermediate 2 A (343 mg, 0.74 mmol) in dichloromethane (4 mL) was added into a solution of 12 (380 mg, 0.72 mmol) in dichloromethane (4 mL). The mixture was stirred for 4 h then the solvent was evaporated. The residue was dissolved in ethanol (5 mL), then $NaBH_4$ (100 mg, 2.6 mmol) was added. The mixture was stirred for 6 h, then quenched with 10% HCl solution. After the solvent was evaporated, it was basified with 10% NaOH solution, extracted with dichloromethane and evaporated. The resulting residue was purified by column chromatography (10% methanol, 0.5% $NH_4OH$ in dichloromethane) to give the product as free amine (295 mg, 42% yield). $^1$H NMR (CDCl$_3$) δ 8.29 (d, J=7.8 Hz, 1H), 7.95 (s, 1H), 7.73-7.78 (m, 2H), 7.41-7.51 (m, 2H), 7.21-7.24 (m, 3H), 7.14 (s, 1H), 7.02-7.08 (m, 2H), 6.86 (d, J=8.2 Hz, 2H), 6.73-6.79 On, 2H), 5.10-5.16 (m, 1H), 4.61 (s, 2H), 4.04 (q, J=6.9 Hz, 2H), 3.84 (s, 3H), 3.72 (s, 2H), 3.44-3.48 (m, 4H), 3.21-3.31 (m, 2H), 3.09 (br s, 2H), 2.59-2.62 (m, 4H), 2.36-2.50 (m, 4H), 2.29 (s, 3H), 2.17-2.24 (m, 3H), 1.88-1.94 (m, 2H), 1.40-1.57 (m, 7H), 1.24-1.30 (m, 6H), 1.21 (t, J=6.9 Hz, 3H). The oxalate salt was prepared using 1 equivalent of oxalic acid in ethanol to give SW V-50s as a light brown solid (308 mg, 95% yield), mp 183-184° C. Anal. ($C_{59}H_{77}N_7O_{11}\cdot 2H_2O$): Calculated, %: C, 64.64; H, 7.45; N, 8.94, Found, %: C, 64.84, H, 7.41, N, 8.62.

TABLE 1

Additional Examples of dual-domain sigma-2 receptor ligand drug conjugate compounds, including sigma-2 receptor ligand erastin conjugate compounds and sigma-2 receptor ligand erastin-analog conjugate compounds.

| Ex. No. | Structure |
|---|---|
| 3 | 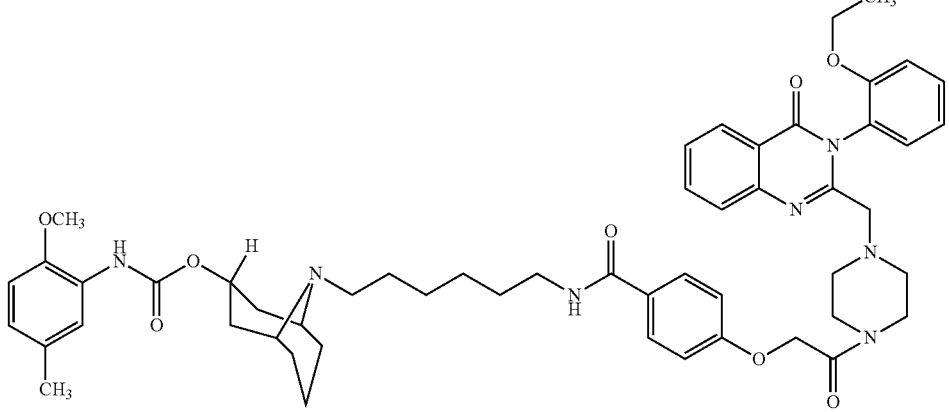 |
| 4 | 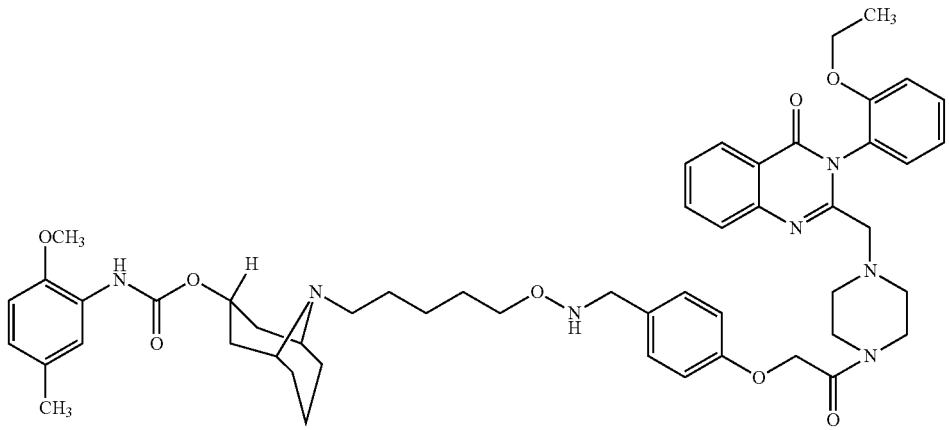 [SMILES: CCOc1ccccc1-n1c(CN2CCN(C(=O)COc3ccc(CNOCCCCCN4C5CCCC4CC(OC(=O)Nc4cc(C)ccc4OC)C5)cc3)CC2)nc2ccccc2c1=O] |

US 10,087,175 B2
31                                                                 32
TABLE 1-continued
Additional Examples of dual-domain sigma-2 receptor ligand drug conjugate
compounds, including sigma-2 receptor ligand erastin conjugate compounds and sigma-2
receptor ligand erastin-analog conjugate compounds.
Ex. No. Structure
5
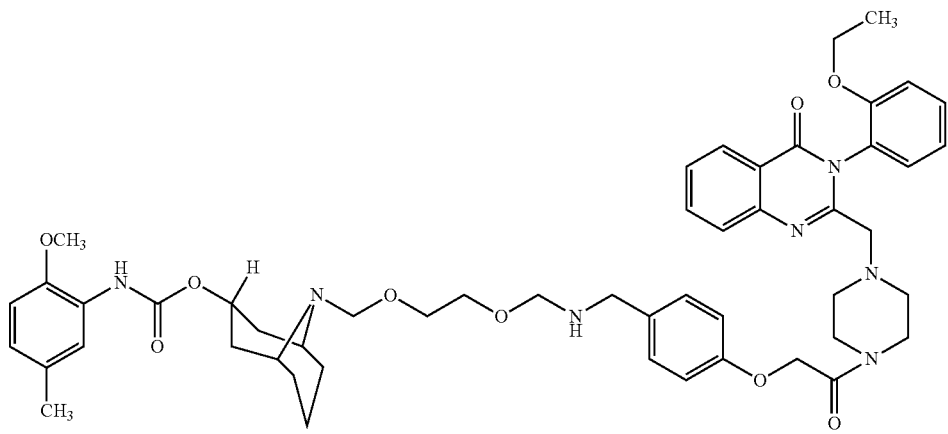
6
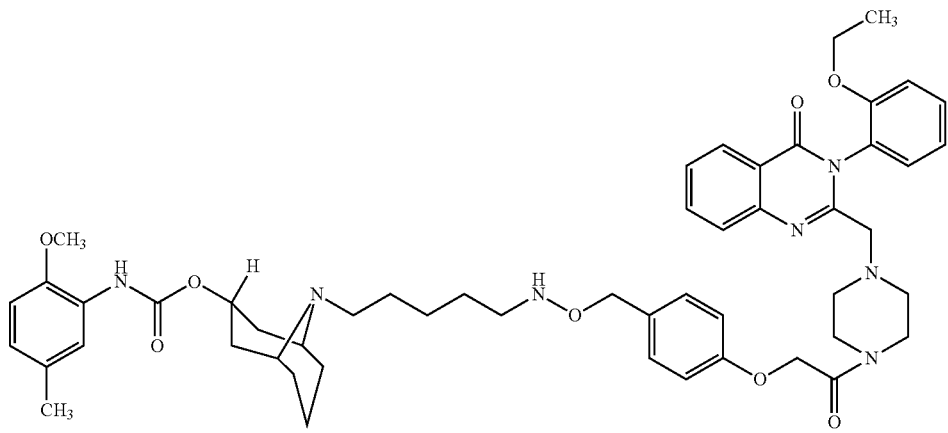 [SMILES: CCOc1ccccc1-n1c(CN2CCN(C(=O)COc3ccc(CONCCCCCN4C5CCCC4CC(OC(=O)Nc4cc(C)ccc4OC)C5)cc3)CC2)nc2ccccc2c1=O]
7
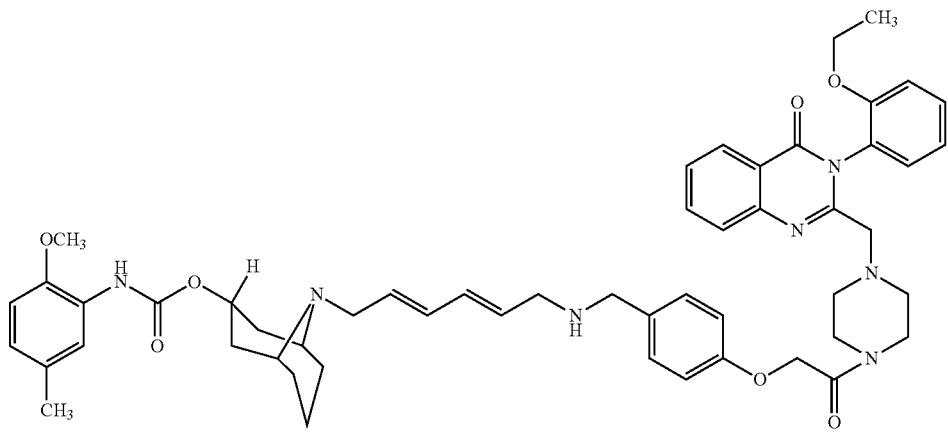 [SMILES: CCOc1ccccc1-n1c(CN2CCN(C(=O)COc3ccc(CNC/C=C/C=C/CN4C5CCCC4CC(OC(=O)Nc4cc(C)ccc4OC)C5)cc3)CC2)nc2ccccc2c1=O]

TABLE 1-continued
Additional Examples of dual-domain sigma-2 receptor ligand drug conjugate compounds, including sigma-2 receptor ligand erastin conjugate compounds and sigma-2 receptor ligand erastin-analog conjugate compounds.
| Ex. No. | Structure |
|---|---|
| 8 | 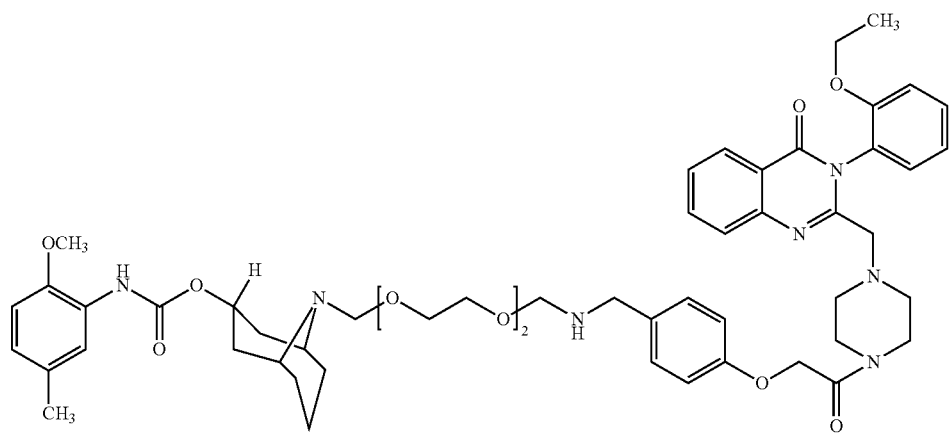 |
| 9 | 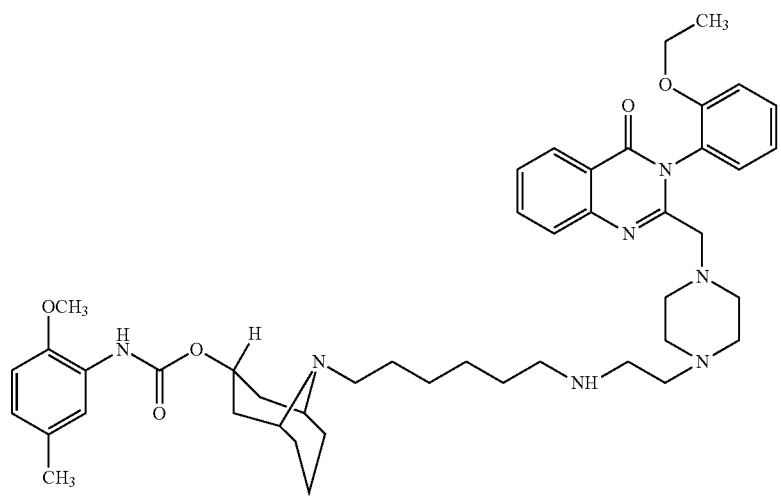 [SMILES: CCOc1ccccc1-n1c(CN2CCN(CCNCCCCCCN3C4CCCC3CC(OC(=O)Nc3cc(C)ccc3OC)C4)CC2)nc2ccccc2c1=O] |
| 10 | 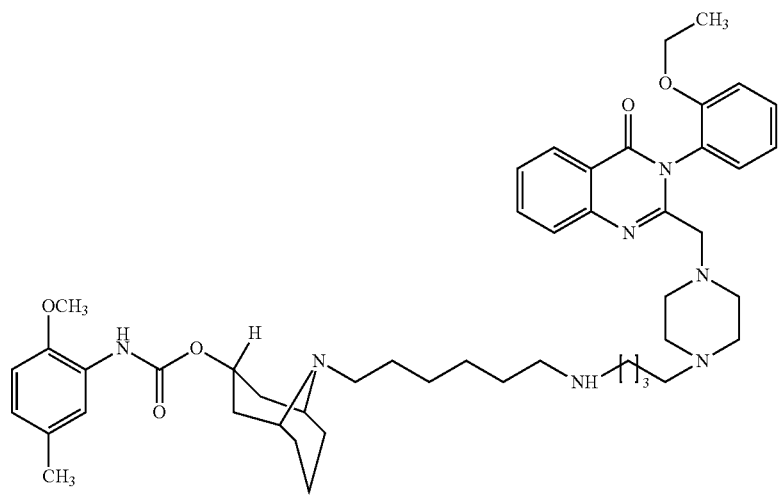 |

TABLE 1-continued
Additional Examples of dual-domain sigma-2 receptor ligand drug conjugate compounds, including sigma-2 receptor ligand erastin conjugate compounds and sigma-2 receptor ligand erastin-analog conjugate compounds.
| Ex. No. | Structure |
|---|---|
| 11 | 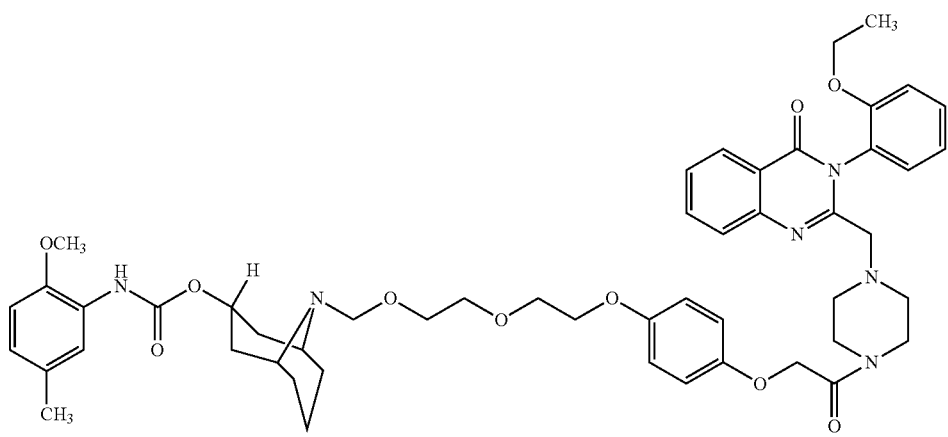 [SMILES: CCOc1ccccc1-n1c(CN2CCN(C(=O)COc3ccc(OCCOCCOCN4C5CCCC4CC(OC(=O)Nc4cc(C)ccc4OC)C5)cc3)CC2)nc2ccccc2c1=O] |
| 12 | 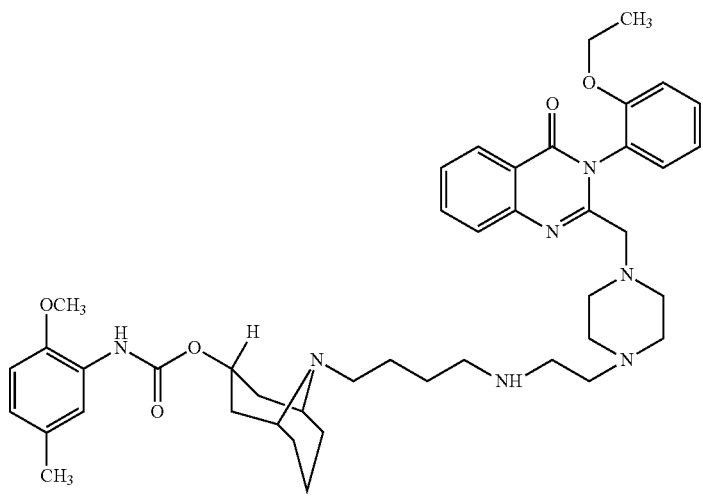 [SMILES: CCOc1ccccc1-n1c(CN2CCN(CCNCCCCN3C4CCCC3CC(OC(=O)Nc3cc(C)ccc3OC)C4)CC2)nc2ccccc2c1=O] |
| 13 | 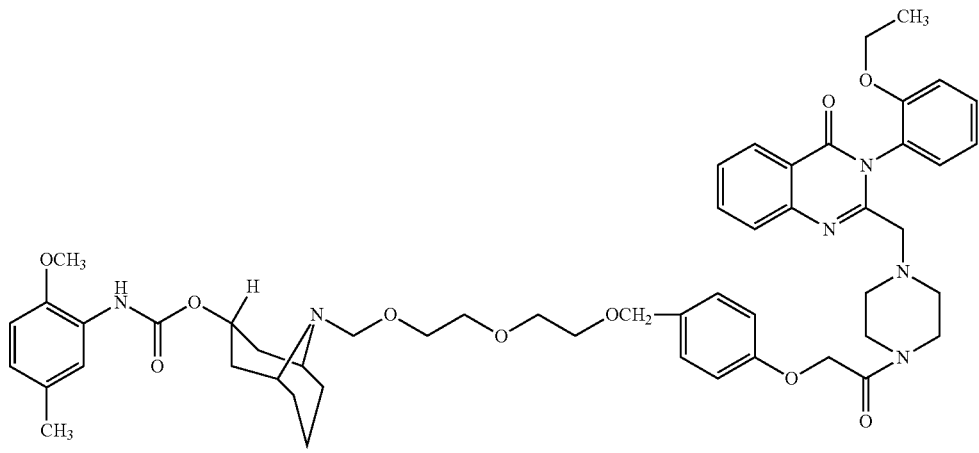 |

TABLE 1-continued
Additional Examples of dual-domain sigma-2 receptor ligand drug conjugate compounds, including sigma-2 receptor ligand erastin conjugate compounds and sigma-2 receptor ligand erastin-analog conjugate compounds.
| Ex. No. | Structure |
|---|---|
| 14 | 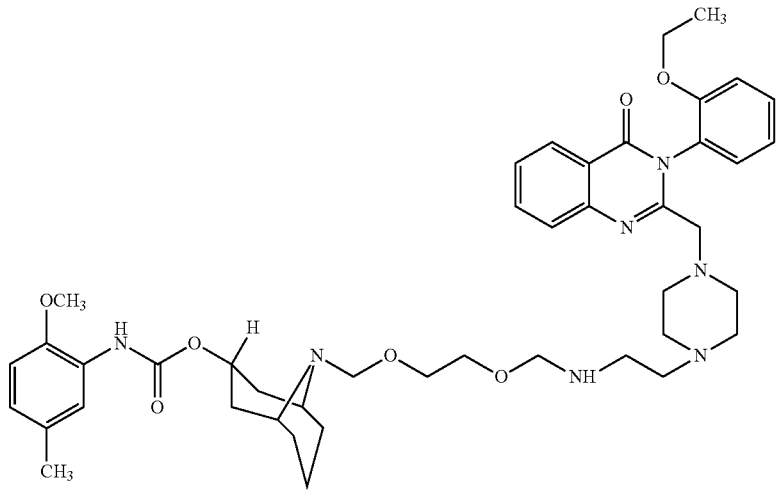 [SMILES: CCOc1ccccc1-n1c(CN2CCN(CCNCOCCOCN3C4CCCC3CC(OC(=O)Nc3cc(C)ccc3OC)C4)CC2)nc2ccccc2c1=O] |
| 15 | 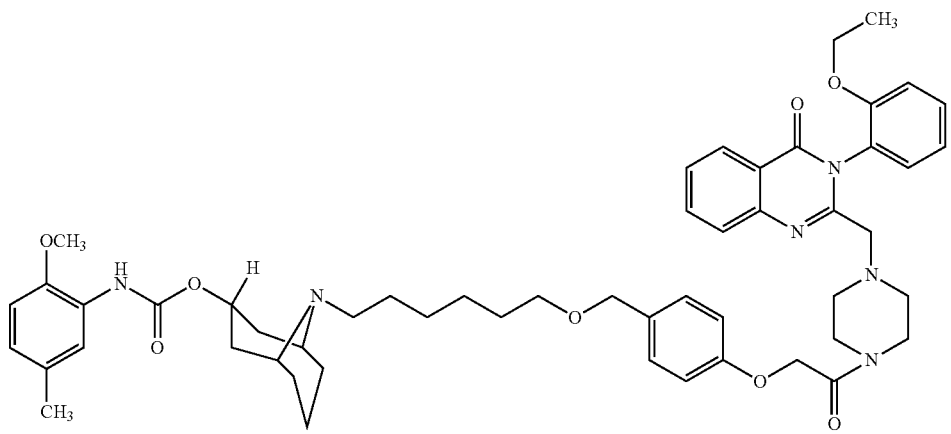 [SMILES: CCOc1ccccc1-n1c(CN2CCN(C(=O)COc3ccc(COCCCCCCN4C5CCCC4CC(OC(=O)Nc4cc(C)ccc4OC)C5)cc3)CC2)nc2ccccc2c1=O] |
| 16 | 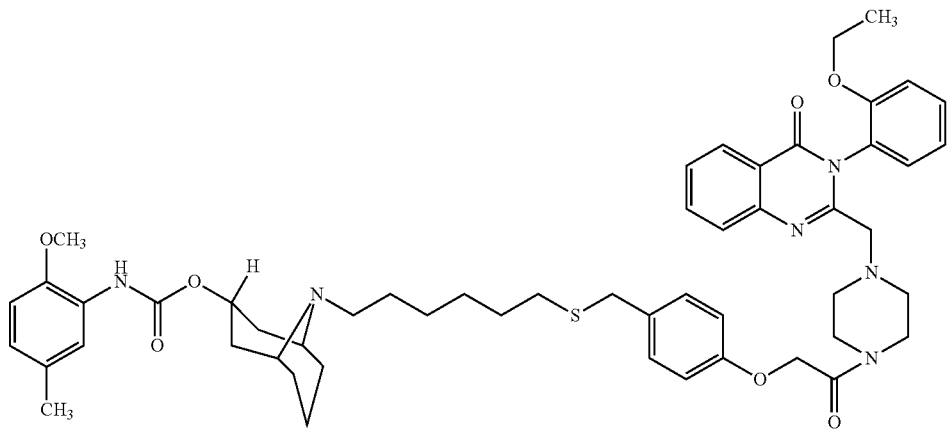 |

TABLE 1-continued
Additional Examples of dual-domain sigma-2 receptor ligand drug conjugate compounds, including sigma-2 receptor ligand erastin conjugate compounds and sigma-2 receptor ligand erastin-analog conjugate compounds.
| Ex. No. | Structure |
|---|---|
| 17 | 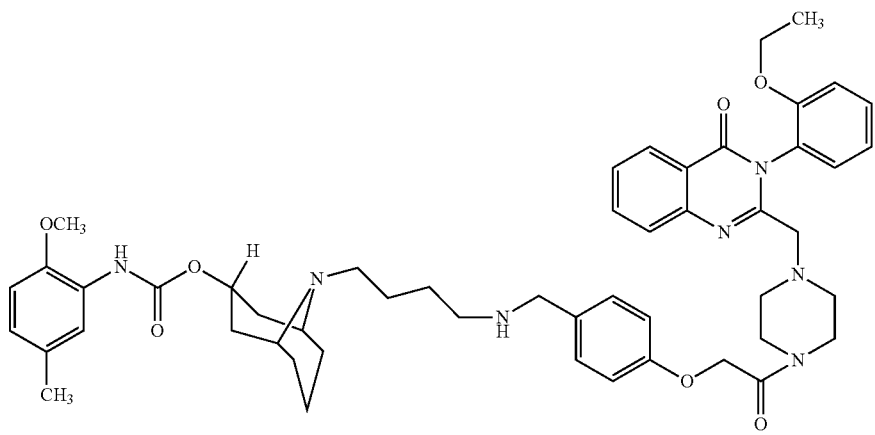 [SMILES: CCOc1ccccc1-n1c(CN2CCN(C(=O)COc3ccc(CNCCCCN4C5CCCC4CC(OC(=O)Nc4cc(C)ccc4OC)C5)cc3)CC2)nc2ccccc2c1=O] |
| 18 | 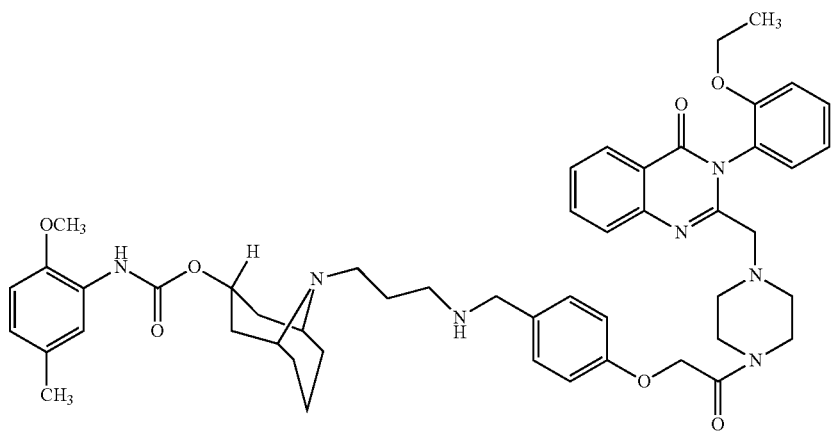 [SMILES: CCOc1ccccc1-n1c(CN2CCN(C(=O)COc3ccc(CNCCCN4C5CCCC4CC(OC(=O)Nc4cc(C)ccc4OC)C5)cc3)CC2)nc2ccccc2c1=O] |
| 18 | 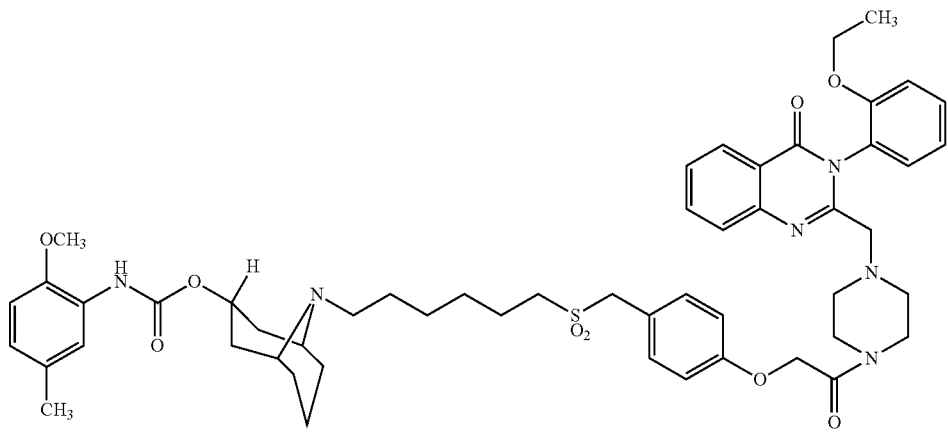 [SMILES: CCOc1ccccc1-n1c(CN2CCN(C(=O)COc3ccc(CS(=O)(=O)CCCCCCN4C5CCCC4CC(OC(=O)Nc4cc(C)ccc4OC)C5)cc3)CC2)nc2ccccc2c1=O] |

TABLE 1-continued
Additional Examples of dual-domain sigma-2 receptor ligand drug conjugate compounds, including sigma-2 receptor ligand erastin conjugate compounds and sigma-2 receptor ligand erastin-analog conjugate compounds.
| Ex. No. | Structure |
|---|---|
| 20 | 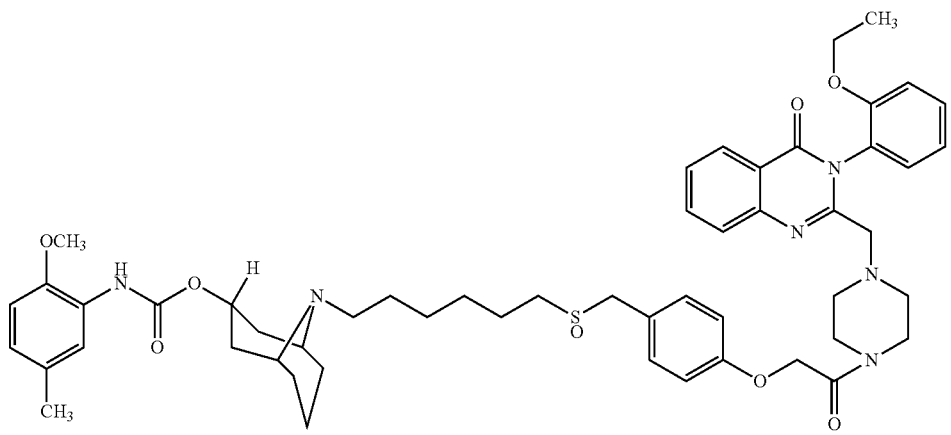 |
| 21 | 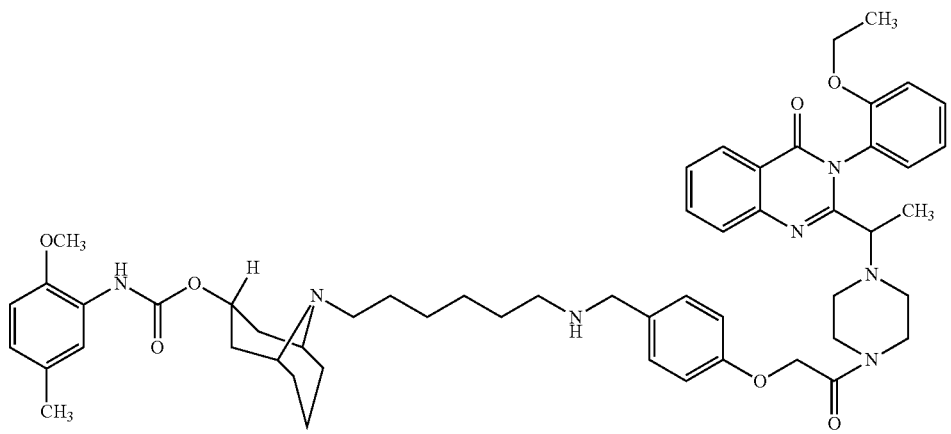 [SMILES: CCOc1ccccc1-n1c(C(C)N2CCN(C(=O)COc3ccc(CNCCCCCCN4C5CCCC4CC(OC(=O)Nc4cc(C)ccc4OC)C5)cc3)CC2)nc2ccccc2c1=O] |
| 22 | 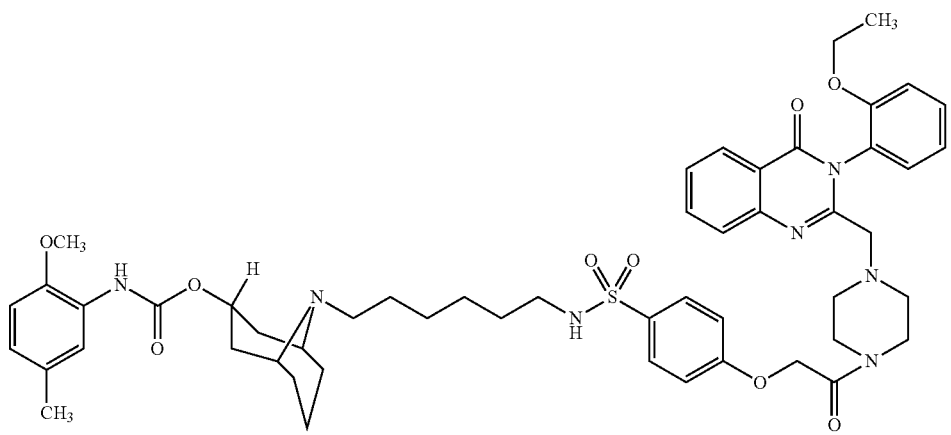 [SMILES: CCOc1ccccc1-n1c(CN2CCN(C(=O)COc3ccc(S(=O)(=O)NCCCCCCN4C5CCCC4CC(OC(=O)Nc4cc(C)ccc4OC)C5)cc3)CC2)nc2ccccc2c1=O] |

TABLE 1-continued

Additional Examples of dual-domain sigma-2 receptor ligand drug conjugate compounds, including sigma-2 receptor ligand erastin conjugate compounds and sigma-2 receptor ligand erastin-analog conjugate compounds.

| Ex. No. | Structure |
|---------|-----------|
| 23 | *(chemical structure)* |
| 24 | *(chemical structure)* |

Biological Activity Assays

The following are assays that can be used to evaluate the biological efficacy of compounds of Formula (I).

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press. Cold Spring Harbor, N.Y., 2001; Spector, D. L. et al., Cells: A Laboratory Manual, Cold Spring Harbor Laboratory Press. Cold Spring Harbor, N.Y., 1998; Nagy, A., Manipulating the Mouse Embryo: A laboratory Manual (Third Edition). Cold Spring Harbor, N.Y., 2003; Harlow, E., Using Antibodies: A laboratory Manual, Cold Spring Harbor Laboratory Press. Cold Spring Harbor, N.Y., 1999; and Carruthers, W., and Coldham, I., Modern Methods of Organic Synthesis (4th Edition), Cambridge University Press, Cambridge, U.K., 2004. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et at., Handbook of Pharmaceutical Excipients, Fourth Edition, Pharmaceutical Press, 2003. As used in the present description and the appended claims, the singular forms "a", "an" and "the" are intended to include the plural forms as well, unless the context indicates otherwise.

Toxicity Study Methods

Six adult female mice were submitted to necropsy. The strain designation of the mice was C57BL/6. Previous procedures included daily intraperitoneal administration of a ferroptosis-inducing drug or vehicle control over the course of 2 weeks. Mice were also previously transplanted subcutaneously with a KCKO xenograft (Besmer, D. M., et al., Cancer Res. 17: 4432-4442, 2011).

Cell Lines

CFPAC-1, BxPC-3, AsPC-1, PANC-1 and Mia PaCa-2 cell lines were obtained from American Type Culture Collection (ATCC, Manassas, Va.). SYO-1 cell line, a synovial sarcoma cell line (Kawai, A., et al., Cancer Lett. 204: 105-113.2004), was provided by Dr. Brian Van Tine (Washington University School of Medicine. St. Louis, Mo.). KCKO cell line was isolated from a human MUC1 expressing pancreatic tumor of transgenic mouse (Besmer et al. Cancer Research 2011; 71: 4432-4442, Tinder et al J Immunol 2008; 181: 3116-3125). The KCKO cell line was provided by Dr. Pinku Mukherjee (University of North Carolina, Charlotte, N.C.). PANC-1 cells were cultured in Dulbecco's Modified Eagle's Medium with 4 mM L-glutamine, 1.5 g/L Sodium bicarbonate, and 10% fetal bovine serum (FBS). Mia PaCa-2 cell line was cultured in Dulbecco's Modified Eagle's Medium with 10% FBS and 2.5% horse serum. BxPC-3, AsPC-1 and KCKO cell lines were cultured in RPM1-1640 medium with 10% FBS. SYO-1 synovial sarcoma cells wore cultured in Dulbecco's Modified Eagle's Medium with 10% FBS. Antibiotics, penicillin (100 mg/ml) and streptomycin (100 mg/ml) were added to the media and cells were maintained in humidified incubator at 37° C. with 5% $CO_2$.

Statistics

Statistical analyses and data plotting were performed using GraphPad Prism software version 6 (San Diego, Calif.). Results were expressed as mean±SEM of at least 3 biological replicates. ) $IC_{50}$ values were calculated by curve fitting normalized viability versus drug concentration. One-way ANOVA was used to analyze the differences in $IC_{50}$ values and SW V-49s inhibition with NAC and ZVAD tests. Unpaired two tailed t-test was used to evaluate the difference in CBC and biochemistry analyses, and to confirm the difference in the subgroups of cystine uptake, caspases, and ROS detection assays. Two-way ANOVA was used to analyze the difference in tumor volume. Kaplan-Meier survival analysis was used and the difference between the groups was compared with a log-rank test. A p-value <0.05 was considered significant for all analyses.

Pre-necropsy Examination.

Mouse A (ID: 732) was a vehicle control. The hair coat was shaved over the right flank, with partial regrowth. A very small, subcutaneous thickening was palpable in the right flank. There was no nasal or ocular discharge or diarrhea. Hydration and body fat were normal. Body weight was 21 grams.

Mouse B (ID: 727) was treated with test drug. The hair coat was shaved over the right flank, with partial regrowth. A subcutaneous mass that measured 1.5×0.6 cm was noted over the lumbar spine, with tight adherence into the underlying musculature. A 4-5 mm diameter ulcer was noted in the skin overlying this mass. There was no nasal or ocular discharge or diarrhea. Hydration and body fat were normal Body weight was 21 grams.

Mouse C (ID: 735) was a vehicle control. Posterior paralysis was noted in this animal, with dragging of the rear limbs. Deep pain response could be elicited from the left rear leg, but not from the right rear leg. The hair coat was slightly thinned over the right flank. A firm, subcutaneous mass was noted over the lumbar spine. This was firmly attached to underlying tissues. A 0.2-0.3 cm diameter thickening of the skin within which was a 0.1 cm diameter ulcer was noted over the right flank. There was no nasal or ocular discharge or diarrhea. Hydration and body fat were normal. Body weight was 20 grams.

Mouse D (ID: 737) was treated with test drug. A subcutaneous mass was palpable over the spine. The hair coat was normal. There was no nasal or ocular discharge or diarrhea. Hydration and body fat were normal. Body weight was 19 grams.

Mouse E (ID: 746) was a vehicle control. The hair coat was shaved over the right flank, with partial regrowth. A 0.6 cm diameter firm subcutaneous nodule was noted in the right flank. There was no nasal or ocular discharge or diarrhea. Hydration and body fat were normal. Body weight was 23 grams.

Mouse F (ID: 738) was treated with test drug. The hair coat was normal. A firm subcutaneous mass was palpable overlying the lumbar spine. The spine was easily palpable, suggesting possible muscle wasting. There was no nasal or ocular discharge or diarrhea. Hydration and body fat were normal. Body weight was 22 grams.

Gross Necropsy Examination.

Regarding Mouse A, the subcutaneous thickening noted on pre-necropsy examination was a firm mass that measures 0.5×0.1 cm. A 0.4×0.1 cm thickened area was noted in the mesentery near the distal colon, and without being limited by theory, possibly the result of an enlarged lymph node. A 2 mm diameter reddened focus was noted in the left lung. The heart and liver were mildly pale. There were no gross lesions in the intestinal tract, musculoskeletal system, urinary system, genital system, brain, thymus, spleen, adrenal, thyroid, pituitary, middle ear, or eye.

Regarding Mouse B, the subcutaneous mass was multilobulated, and measured 1.8×0.6 cm, with an attached 1.0 cm diameter nodule. The subcutaneous mass was located subcutaneously over the lumbar spine and right lateral dorsum. There was no infiltration into the spine. The mass projected ventrally impinging upon the abdomen. The liver was slightly pale. The heart was mildly pale. There were no gross lesions in the respiratory system, intestinal tract, urinary system, genital system, brain, thymus, spleen, lymph nodes, adrenal, thyroid, pituitary, middle ear, or eye.

Regarding Mouse C, the subcutaneous mass measured 1.8×1.7×1.5 cm and appeared to encompass the mid-lumbar spine. The mass was pale-tan, firm and slightly nodular. The heart and liver were mildly pale. There were no gross lesions in the respiratory system, intestinal tract, urinary system, genital system, brain, thymus, spleen, lymph nodes, adrenal, thyroid, pituitary, middle ear, or eye.

Regarding Mouse O, the subcutaneous mass measured 1.2×0.8 cm and lay over the lumbar spine. Without being limited by theory, the dorsal spinous processes of the vertebrae can have been eroded by the tumor. The liver was mildly pale. There were no gross lesions in the respiratory system, intestinal tract, urinary system, genital system, heart, brain, thymus, spleen, lymph nodes, adrenal, thyroid, pituitary, middle ear, or eye.

Regarding Mouse E, the lungs were mottled red in color. The liver was slightly pale. There were no gross lesions in the intestinal tract, musculoskeletal system, urinary system, genital system, heart, brain, thymus, spleen, lymph nodes, adrenal, thyroid, pituitary, middle ear, or eye.

Regarding Mouse F, there were two masses noted in the skin and subcutaneous tissues. One measured 0.5×0.5×0.3 cm and was located in the skin, and the other measured 0.5×0.5×0.2 cm and was in the subcutaneous tissues overlying the lumbar spine. There were no gross lesions in the respiratory system, intestinal tract, urinary system, genital system, heart, brain, thymus, spleen, lymph nodes, adrenal, thyroid, pituitary, middle ear, or eye.

Histopathologic Examination.

Regarding Mouse A, mild, multifocal inflammatory infiltrates were noted in the mesenteric fat that included macrophages, neutrophils, lymphocytes, and plasma cells. A reactive mesenteric lymph node was noted, with lymphoid hyperplasia, histiocytosis and dilatation of the medullary sinuses. In the lung there was moderate focal hemorrhage noted in one lobe, without limited by theory, likely related to $CO_2$ euthanasia. There were no significant lesions in the brain, heart, liver, kidney, spleen, pancreas, or gastrointestinal tract.

Regarding Mouse B, mild to moderate chronic peritonitis was noted in the mesentery and along the serosal surfaces of the small and large intestinal tract and stomach, as well as around the pancreas. This was characterized by infiltrates of macrophages, neutrophils, lymphocytes, and plasma cells, along with areas of fibrosis. Mild mucosal hyperplasia was noted in the ileum. A mesenteric lymph node located near the pancreas was reactive, as described previously. No lesions were noted within in the pancreatic parenchyma. Mild peritonitis was noted around the gall bladder and along the capsular surface of the right kidney. No other lesions were noted in the liver or kidneys. Mild capsular thickening and mesothelial hyperplasia were noted along the spleen. There was a moderate increase in extramedullary erythropoiesis in the red pulp of the spleen. There were no significant lesions in the brain, heart, or lungs.

Regarding Mouse C, examination of the lungs revealed a few small foci of metastasis of the primary tumor. Without being limited by theory, the primary tumor appeared to have invaded bone, as small bone fragments were noted within the mass. There were no significant lesions in the brain, heart, liver, kidney, spleen, pancreas, or gastrointestinal tract.

Regarding Mouse D, minimal to mild chronic peritonitis was noted along the serosal surface of the stomach, intestinal tract, and around the pancreas, with inflammatory cells and areas of fibrosis, as described previously. Foci of peritonitis were also noted along the capsular surfaces of the liver and kidneys. No other lesions were noted in the gastrointestinal tract, pancreas, liver, and kidneys. In the spleen there was a moderate increase in extramedullary erythropoiesis. In the lung there were 2 small foci of pyogranuloma noted in one lung lobe. This was of unknown etiology; no foreign material was noted in association. Tumor invasion into the lumbar musculature was evident. Tumor cells also closely approached the vertebral body and surrounded a small bone fragment, without being limited by theory, presumed to represent a dorsal spinous process of the vertebral body. There were no significant lesions in the brain or heart.

Regarding Mouse E, in the mesenteric fat there were minimal to mild infiltrates of macrophages, lymphocytes, neutrophils, and plasma cells. A mildly reactive lymph node was noted near the pancreas, as described previously. There were no significant lesions noted in the brain, heart, lung, liver, kidneys, pancreas, spleen, or gastrointestinal tract.

Regarding Mouse F, mild chronic peritonitis was noted along the serosal surfaces of the intestinal tract and in the mesentery surrounding the pancreas, as described previously. In one pancreatic lobule there was loss of acinar cells and replacement by macrophages and fibroblasts, presumably representing an extension of the reaction noted in the mesentery. Mild peritonitis was also noted on the capsule and in the mesentery surrounding the kidneys. No other lesions were noted in the intestinal tract, liver, or kidneys. In the spleen there was a moderate increase in extramedullary erythropoiesis and granulopoiesis. There were no gross lesions in the brain, heart, lungs, or stomach.

Hematological Testing.

A difference noted between the drug-treated and control animals was the presence of minimal to moderate chronic peritonitis along the serosal surfaces of the intestinal tract and abdominal organs and in the mesentery surrounding the pancreas, noted in the drug-treated animals. Whereas the control animals showed minimal to mild multifocal inflammatory infiltrates in the mesentery, without fibroplasia. Other findings included elevation of ALT and AST noted in mouse C. Without being limited by theory, the etiology of this finding was not clear. There was not histologic evidence of hepatocellular injury, as might be expected. Without being limited by theory, other potential causes included hemolysis of the blood sample, or bone injury from tumor invasion.

In mouse C there was tumor invasion into lumbar musculature, with fragmentation of bone, without being limited by theory, likely that of a vertebral process, as well as pulmonary metastasis. In mouse D there was invasion of tumor into the lumbar musculature, and fragmentation of the dorsal spinous process.

TABLE 2

Complete Blood Count Results

| ID | WBC ($10^3/\mu L$) | RBC ($10^6/\mu L$) | HGB (g/dl) | PCV (%) | MCV (u) | MCH (pg) | MCHC (%) | Platelets ($10^3/\mu L$) |
| --- | --- | --- | --- | --- | --- | --- | --- | --- |
| A-732 | 7.72 | 9.15 | 12.4 | 49.2 | 53.8 | 13.6 | 25.2 | 651 |
| B-735 | 8.10 | 8.89 | 11.2 | 45.6 | 51.3 | 12.6 | 24.6 | 745 |
| C-746 | 5.54 | 8.89 | 11.5 | 44.7 | 50.3 | 12.9 | 25.7 | 788 |
| D-727 | 4.16 | 7.66 | 9.8 | 37.7 | 49.2 | 12.8 | 26.0 | 611 |
| E-737 | 5.68 | 8.67 | 10.7 | 39.3 | 45.3 | 12.3 | 27.2 | 749* |
| F-738 | 3.34 | 8.40 | 10.5 | 42.4 | 50.5 | 12.5 | 24.8 | 885 |

*Mild platelet clumping was noted.

TABLE 3

Differential Results

| ID | Neutrophils (%) | Lymphocytes (%) | Monocytes (%) | Eosinophils (%) | Basophils (%) | Bands (%) | nRBC (%) |
| --- | --- | --- | --- | --- | --- | --- | --- |
| A-732 | 14 | 83 | 3 | 0 | 0 | 0 | 0 |
| B-735 | 46 | 49 | 5 | 0 | 0 | 0 | 0 |

TABLE 3-continued

Differential Results

| ID | Neutrophils (%) | Lymphocytes (%) | Monocytes (%) | Eosinophils (%) | Basophils (%) | Bands (%) | nRBC (%) |
|---|---|---|---|---|---|---|---|
| C-746 | 13 | 81 | 6 | 0 | 0 | 0 | 0 |
| D-727 | 13 | 87 | 0 | 0 | 0 | 0 | 0 |
| E-737 | 2 | 96 | 2 | 0 | 0 | 0 | 0 |
| F-738 | 18 | 78 | 4 | 0 | 0 | 0 | 0 |

TABLE 4

Clinical Chemistry Results

| ID | BUN (mg/dL) | Creatinine (mg/dL) | ALT (u/L) | AST (u/L) | Glucose (mg/dL) | Total Protein (g/dL) |
|---|---|---|---|---|---|---|
| A-732 | 23 | 0.33 | 95 | 87 | 179 | 6.1 |
| B-735 | 17 | 0.26 | 65 | 73 | 180 | 5.4 |
| C-746 | 28 | 0.28 | 506 | 715 | 187 | 5.5 |
| D-727 | 19 | 0.22 | 138 | 167 | 178 | 5.1 |
| E-737 | 22 | 0.21 | 64 | 147 | 310 | 5.7 |
| F-738 | 17 | 0.24 | 63 | 55 | 180 | 5.1 |

Sigma-2 Receptor Binding Properties of Compound SW V-49s

In these experiments, competitive binding assays of SW V-49s with the fluorescently labeled sigma-2 ligand SW120 of structure

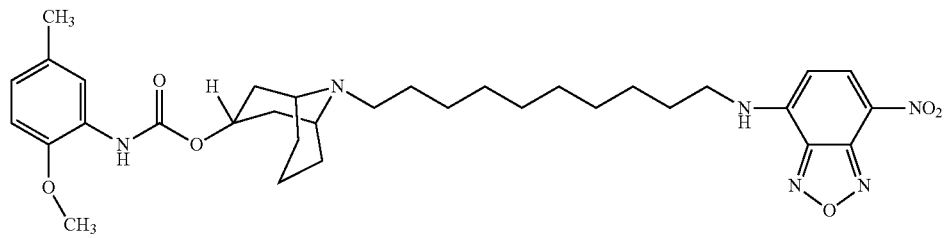 [SMILES: COc1ccc(C)cc1NC(=O)OC1CC2CCCC(C1)N2CCCCCCCCCCNc1ccc([N+](=O)[O-])c2nonc12]

were conducted.

AsPC-1 cells (5×10$^5$/well) were seeded into a 6 well plate for 24 hours before treatment. The cells were then incubated with 0, 10, 30 and 50 µM of SW V-49s for 30 minutes at 37° C. Subsequently, 10 nM of fluorescently labeled sigma-2 ligand SW120 was added to the cell culture medium containing SW V-49s. After 30 minute of incubation at 37° C., cells were washed twice with phosphate buffered saline (PBS) and harvested with 0.05% trypsin EDTA (Life Technologies. Grand Island, N.Y.). Thereafter, the cells were centrifuged at 1000×g for 5 minutes and the pellets were washed twice with PBS. Internalization of SW120 was determined by flow cytometer (FACSCalibur™, BD Biosciences, San Jose, Calif.).

FIG. 3 shows competitive inhibition of internalization of 10 µM of fluorescently labeled SW 120 (Spitzer. D., et al. Cancer Res. 72:201-209,2012) vs. SW V-49s in human Pane-1 cells. These data indicate efficient blocking of SW 120 internalization with increasing concentrations of SW V-49s. These results indicate that SW V-49s efficiently binds sigma-2 receptors.

SW V-49s Exhibits Lethality Towards Cancer Cell Lines In Vitro.

Figure 4A:
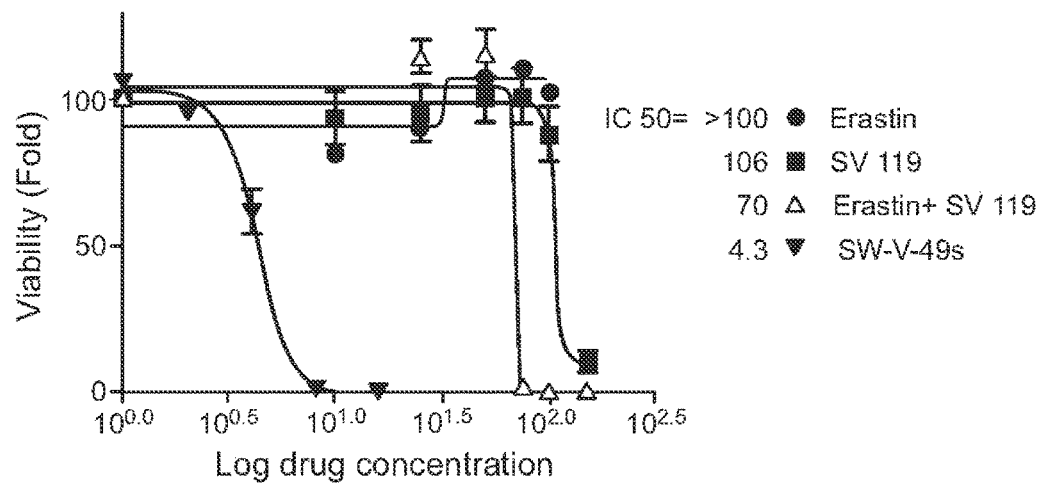
Figure 4B:
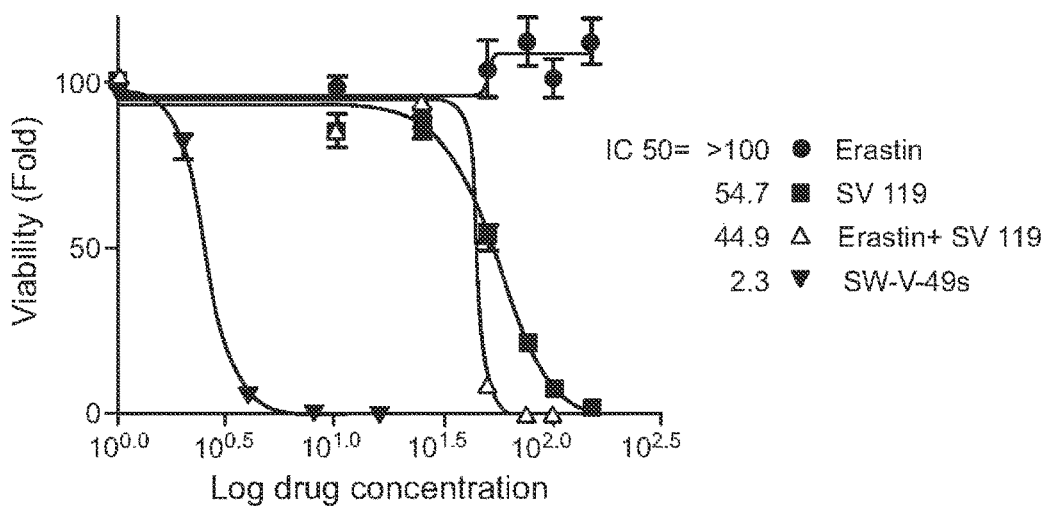
Figure 4C:
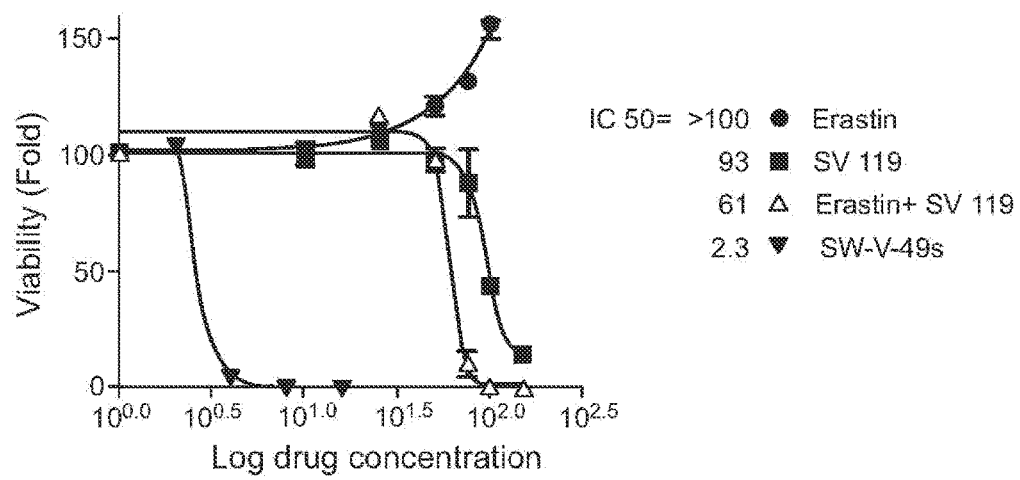
Figure 4D:
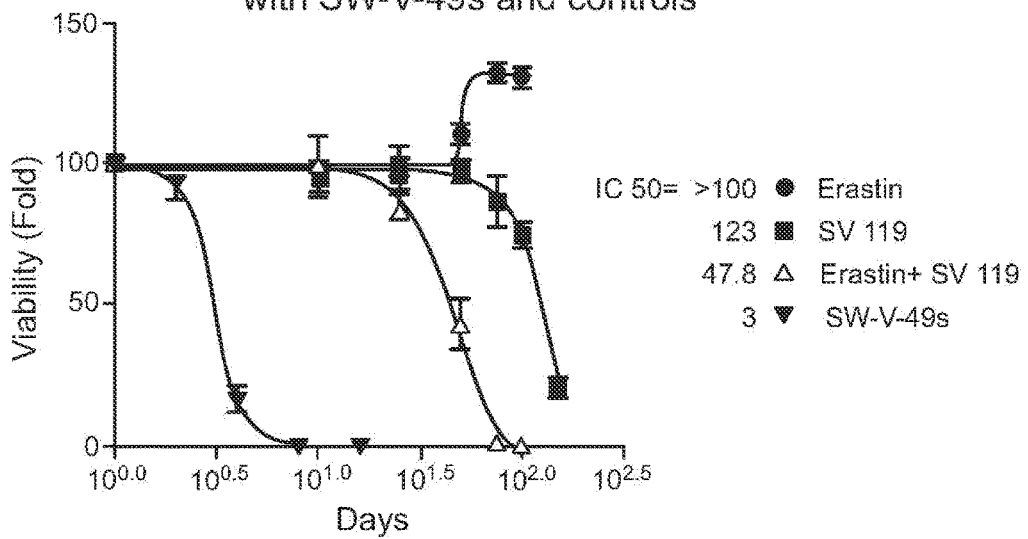
Figure 4E:
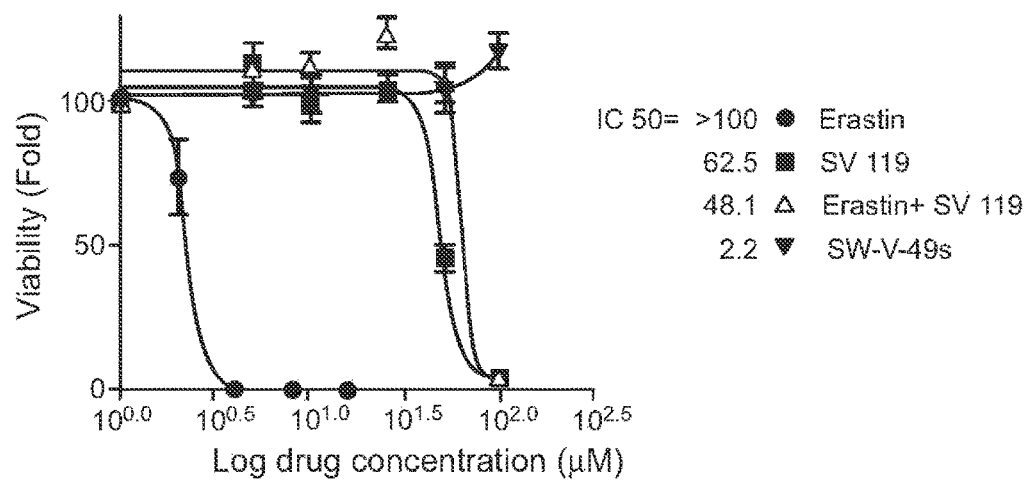
Figure 4F:
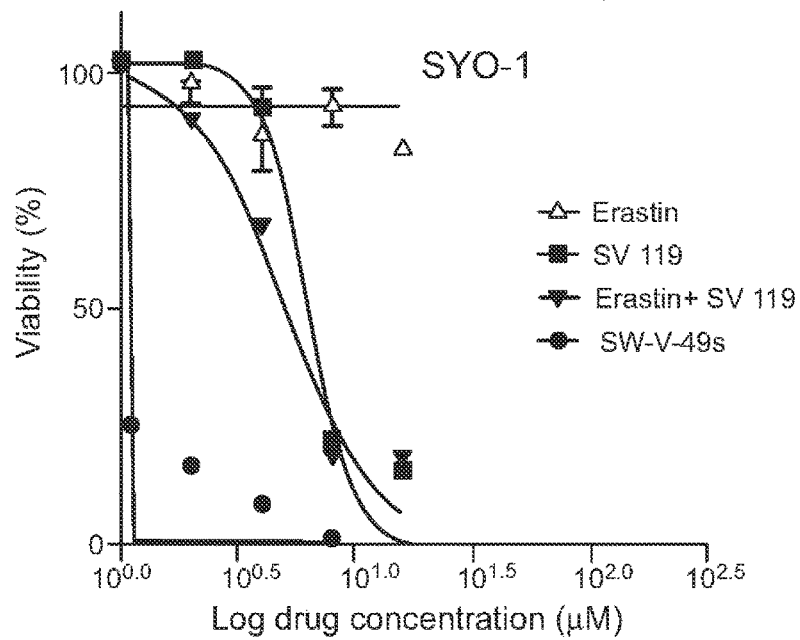

In these experiments, viability assays after 24 hours treatment of human and murine pancreatic cancer cell lines and synovial sarcoma cell lines with SW V-49s or its parent compounds SV 119 and Erastin, both singly and in combination, were performed. The data demonstrate an IC$_{50}$ concentration of 4.3 µM for SW V-49s against human pancreatic-cancer cell line Pane-1 (ATCC® CRL-1469™) (FIG. 4A): an IC$_{50}$ concentration of 2.3 µM for SW V-49s against for human pancreatic cancer cell line BxPC-3 (ATCC® CRL-1687™)(FIG. 4B); an IC$_{50}$ concentration of 2.3 µM for SW V-49s against human pancreatic cancer cell line MIA PaCa-2 (ATCC® CRL-1420™)(FIG. 4C); an IC$_{50}$ concentration of 3 µM for SW V-49s against human pancreatic cancer cell line AsPC-1 (ATCC® CRL-1682™) (FIG. 4D); and an IC$_{50}$ concentration of 2.2 µM for SW V-49s against a murine pancreatic cancer cell line (KCKO cells) (FIG. 4E). In comparison, Erastin alone exhibited an IC$_{50}$>100 µM against all human and murine pancreatic cancer cell lines tested; SV 119 alone exhibited an IC$_{50}$>54 µM against all human and murine pancreatic cancer cell lines tested: and equimolar mixture of Erastin and SV 119 exhibited an IC$_{50}$>44 µM against all human and murine pancreatic cancer cell lines tested.

Synovial sarcoma cell lines (FIG. 4F, SYO-1, ME1 deficient) are so sensitive to SW V-49s that it was difficult to measure the minimal drug concentration required to kill 50% of the cancer cells, but the measured IC$_{50}$ was approx. 1.0 µM. In comparison, IC$_{50}$'s for other compounds tested against synovial sarcoma cells were as follows: Erastin, >16 µM; SV119, 6.2 µM; Erastin +SV119, 4.9 µM.

These data indicate that SW V-49s is far more lethal against cancer cells, including human and murine pancreatic cancer cells and Synovial sarcoma cells, compared to its component parent compounds, either individually or in combination.

Dual Functionality of SW V-49s.

In these experiments, the inventors investigated whether compounds of the present teachings were lethal towards pancreatic cancer cells by triggering an apoptosis cell death pathway, a ferroptosis cell death pathway, or a combination thereof. The inventors thus performed assays for caspase 3/7 as an indicator of apoptotic cell death, and assays for the generation of reactive oxygen species (ROS) as an indicator of ferropoptotic cell death. As shown in FIG. 5A, 24 hr. treatment of AsPC-1 cells with 50 μM Erastin, SV 119 or an equimolar mixture of Erastin plus SV 119 led to far less caspase activity compared to 4 μM SW V-49s. In FIG. 5B, results ate shown for Caspase-Glo® (Promega) assays of Aspc-1 cells treated with 8 μM SW V-49s, 8 μM Erastin, 8 μM SV 119, or 8 μM of an equimolar mixture of Erastin and SV 119, for 7 hrs. Cells treated with SW V-49s had a significant increase (approximately 3 fold) in caspase 3/7 activity compared to all controls *$p<0.0001$.

In FIG. 6. results are shown for reactive oxygen species (ROS) assays of Aspc-1 treated with 8 μM 8 μM SW V-49s, 8 μM Erastin, 8 μM SV 119, or 8 μM of an equimolar mixture of Erastin and SV 119, or a positive control for 30 min. Cells treated with SW V-49s had a significant (50%) increase in ROS caspase *$p<0.0001$ compared to Erastin, SV 119 or a combination thereof, consistent with ferropoptotic cell death. Parent compounds SV 119 and Erastin, applied to cells either singly or in combination, had no effect at the same concentration.

son, Wis.). Pancreatic cell lines were plated at a density of $2\times10^4$/well in white 96 well, clear bottom plates for 24 hours prior to treatment. Drugs were dissolved in DMSO and serially diluted in culture medium to achieve the final concentration of DMSO less than 1%. Cells were then treated for 24 hours and 100 μl of the CELLTITER-GLO® reagent was added to each well. The contents of the plates were mixed using an orbital shaker and subsequently incubated for 10 minutes at room temperature. Luminescence signal was measured using a multi-mode microplate reader (BioTek instruments, Winooski, Vt.). Different drug concentrations were assayed in triplicate. To evaluate the efficacy of the drugs, $IC_{50}$ of the compounds was calculated on a panel of human and mouse derived pancreatic cancer cell lines in vitro. Cells were treated for 24 hours with SW V-49s, SV 119, Erastin, and an equimolar mixture of SV119 and Erastin, then CELLTITER-GLO® viability assay was performed. Erastin was the least active compound, with $IC_{50}>150$ μM. SV 119 demonstrated a modest efficacy, that was augmented by adding Erastin. However, SW V-49s showed robust cytotoxicity with 17-20 fold reduction of $IC_{50}$ as compared to treatment with the equimolar mixture of SV119 and Erastin (Table 4 and FIG. 9). These results indicate that SW V49s is selectively delivered to pancreatic cancer cells.

TABLE 5

$IC_{50}$ (μM) of pancreatic cell lines treated with different compounds for 24 hours.

| Drugs | Cell Line | | | | |
|---|---|---|---|---|---|
| | PANC-1 $IC_{50} \pm$ SEM | BxPC-3 $IC_{50} \pm$ SEM | AsPC-1 $IC_{50} \pm$ SEM | MiaPaCa-2 $IC_{50} \pm$ SEM | KCKO $IC_{50} \pm$ SEM |
| SW V-49s | 4.1 ± 0.2 | 2.5 ± 0.1 | 3.2 ± 0.3 | 3.0 ± 0.3 | 2.4 ± 0.2 |
| SW119 + Erastin | 70 ± 0.3 | 40.6 ± 2.5 | 46.5 ± 2.9 | 50.6 ± 2.5 | 48.4 ± 0.8 |
| SV119 | 111.3 ± 5.3 | 54.2 ± 2.6 | 111.3 ± 8.3 | 94.5 ± 1.9 | 68.7 ± 10.1 |
| Erastin | >150 | >150 | >150 | >150 | >150 |

(Mean ± SEM), n ≥ 3.
P < 0.05

Without being limited by theory, these data indicate that SW V-49s induces both apoptotic and ferropoptotic cell death pathways in pancreatic cancer cells.

Administration of SW V-49s can Decrease Pancreatic Tumor Size In Vivo.

FIG. 7 illustrates changes in mean tumor volume (in mm$^3$) following administration to interval of C57BL/6 mice with established, syngeneic, subcutaneous KCKO mouse pancreatic tumors over a period of 10 days for SW V-49s, Erastin, SV119, a mixture of Erastin and SV119, and a vehicle control. SW V-49s treatment, but no other treatment, led to a significant decrease in tumor volume ($p<0.05$). These treatments resulted in minimal off-target effects. Note in FIG. 7 the decrease in tumor volume from approx. 40 mm$^3$ to approx. 20 mm$^3$ in SW V 49s-treated mice, compared to an increase from approx. 40 mm$^3$ to approx. 140 mm$^3$ for other treatments.

Administration of SW V-49s can Increase Survival of Pancreatic Cancer in a Murine Model System.

In these experiments, in a survival study of the mice reported in Example 9, the group which received SW V-49s survived at 100% (FIG. 8), In all other groups, the mean survival clustered at around 18 days.

SW V-49s Induces Cell Death in Pancreatic Cancer.

Cytotoxicity of the drugs was evaluated by CELLTITER-GLO®. Luminescent cell viability assay (Promega, Madi- Since Erastin demonstrated no effects in all pancreatic cell lines, the inventors performed a quality control experiment using SYO-1 cells. AsPC-1 and SYO-1 cells were plated in 96 well plate overnight then treated with similar concentrations of Erastin for 24 hours. Viability assay was performed after 24 hours. Treatment with 40 μM Erastin resulted in the death of 84% of SYO-1 cells, as compared to 2% of AsPC-1 cells, ($p<0.0001$), (FIG. 10). This experiment demonstrates that the Erastin used is bioactive and the pancreatic cell lines are resistant to Erastin.

SW V-49s Inhibits Cystine Uptake and Generates Reactive Oxygen Species.

In these experiments, cystine uptake assay was performed as previously described (Dixon, S. J. et al Cell 2012; 149: 1060-1072). Briefly, $5\times10^5$ AsPC-1 cells/well were seeded overnight in 6 well plate. The next day, cells were washed twice in pre-warmed Na$^+$-free uptake buffer (137 mM choline chloride, 3 mM KCl, 1 mM CaCl$_2$, 1 mM MgCl$_2$, 5 mM D-glucose, 0.7 mM K$_2$HPO$_4$, and 10 mM HEPES [pH 7.4]). Subsequently, cells were incubated for 10 minutes at 37° C. in 1 ml of the uptake buffer to deplete cellular amino acids. The buffer was then replaced with 600 μl uptake buffer containing 200 μM of SW V-49s and 0.12 μCi (80-110 mCi/mmol) of L-[3,3'-$^{14}$C]-cystine (American Radiolabeled Chemicals, St Louis, Mo.) and incubated for 3 minutes at 37° C. After that, cells were washed three times with ice-cold uptake buffer and lysed in 500 µl of 0.1 M NaOH. To this lysate, 1 ml of scintillation fluid was added, and radioactive counts per minute were obtained by using a scintillation counter.

Erastin has been shown to block cystine uptake by inhibiting cystine/glutamate antiporter (system $X_c^-$) resulting in ROS dependent cell death (Dixon et al Cell 2012: 149: 1060-1072). To evaluate this mechanism. AsPC-1 cells were plated in 6 well plate for 24 hours. Cells were then treated with the same concentration of SV119, Erastin, combination of SV 119 and Erastin, SW V-49s, and DMSO as a control. After that, a cystine uptake assay was performed. Cells treated with SW V-49s demonstrated a reduction in cystine uptake by 85% (3.7 fold less cysteine uptake) as compared to 25%, 41%, and 44% in the cells treated with SV 119. Erastin, and combination of SV 119 and Erastin, respectively (p=0.004, FIG. 11A).

ROS measurement was performed using Total ROS/Superoxide Detection Kit (Enzo life sciences, Farmingdale, NY) according to the manufacturer's instructions. Briefly, As PC-1 cells were seeded at a density of $2 \times 10^4$ cells/well in a black wall clear bottom 96-well plate for 24 hours. Compounds were dissolved in DMSO and diluted in culture medium to achieve a final concentration of DMSO less than 1%. AsPC-1 cells were treated with 8 µM of SV119, Erastin, and equimolar mixture of SV119 and Erastin. ROS assay was performed one hour after treatment. Cells were treated for one hour, then media was removed and 100 µL/well of ROS/Superoxide Detection Mix was added. Fluorescence signal was measured using a multi-mode microplate reader (Bio-Tek, Winooski, Vt.). The assay was performed in 6 replicates.

The ROS level of the cells treated with SW V-49s was 1.5 fold higher compared to others. There was no increase in the ROS level in cells treated with SV 119, Erastin, and equimolar mixture of SV119 and Erastin at that concentration (FIG. 11B, $p<0.0001$).

Compound SW V-49s can Induce Intrinsic Apoptotic Pathway.

In these experiments, caspase-3/7.8 and 9 activities were measured In AsPC-1 cells using the corresponding CASPASE-GLO® Assay according to the manufacturer's instructions (Promega, Madison, Wis.). This assay is based on a caspase-specific substrate, which is cleaved to release aminoluciferin, a substrate of luciferase that results in caspase-specific luminescence signals. Cells were seeded at a density of $2 \times 10^4$ in white 96-well, clear bottom plates for 24 hours before treatment with 4 µM of compounds. The contents were then mixed using a plate shaker for 30 seconds, thereafter incubated at room temperature for 90 minutes. Luminescence signal was measured using a multi-mode microplate reader (BioTek). Assay was performed in triplicates, and the caspase activity of DMSO was considered as a base line.

The present inventors have shown that SV119 induces caspase-3 dependent apoptosis (Kashiwagi, H., et al. Mol Cancer 2007; 6:48). In these experiments, AsPC-1 cells were treated with 4 µM of SW V-49s, SV119, Erastin, and equimolar mixture of SV119 and Erastin for 24 hours. Using CASPASE-GLO® Assays, Caspase-3 level was measured to assess the activity of SW119 domain of the SW V-49s compound and Caspase-8 and 9 levels were measured to identify which apoptotic pathway was involved. Cells treated with SW V-49s had a significant increase in caspase-3 and 9 (3.4 and 3.2 fold above baseline respectively, ***$p<0.001$, FIG. 12A and FIG. 12B, respectively). In contrast, there was no significant increase in caspase 8, ns>0.5 (FIG. 12C). Other compounds tested did not activate any of the caspases at a similar concentration (FIG. 12A-C). These results suggest that SW V-49s can be selectively delivered to the cancer cells and its two domains can work synergistically to activate the intrinsic apoptotic pathway.

SW V-49s can Induce ROS and Apoptotic Dependent Cell Death.

The present inventors demonstrated that SW V-49s can induce apoptosis and ROS generation. To assess the roles of these two mechanisms on the induction of cell death, the effects of pan-caspase inhibitor and antioxidant on the efficacy of SW V-49s were tested. In these experiments, AsPC-1 cells were pre-treated with 10 mM of the antioxidant N acetyl cysteine (NAC), 20 µM of pan-caspase inhibitor ZVAD, and DMSO as a control for 1 hour. Then, the 3 groups were treated with 10 µM of SW V-49s for 5 hours, after which a CELLTITER-GLO® viability assay was performed. The results indicated that viability of cells treated with SW V-49s alone was reduced to 39% compared to 63% and 91% in cells pretreated with NAC and ZVAD respectively (FIG. 13, $p<0.0001$). NAC was found to be more effective in inhibiting SW V-49s activity (FIG. 13. $p<0.002$). These data demonstrate the dual functionality of SW V-49s and indicate that it can induce both apoptotic and ROS dependent cell death.

SW V-49s Reduces Tumor Growth and Enhances Survival in Mouse and Patient Derived Xenograft Models of Pancreatic Cancer.

Animal studies were performed according to the animal studies protocol approved by Washington University Institutional Animal Care Facility. In vivo studies with mice were performed to compare the effects of SW V-49s, SV119, Erastin, a combination of SV119 with Erastin. and vehicle. The vehicle used in the in vivo studies is a mixture of 25% cremophor and 75% $H_2O$. C57BL/6 mice (6 weeks old. National Cancer Institute Laboratories) were injected in the right flank with 200 µL single cell suspension of KCKO cells in RPMI medium ($25 \times 10^4/10^5$ cells per mouse). Mice were randomized into four groups (n=15). Treatment was started when the mean tumor diameter was ~5 mm. Mice received daily intra peritoneal injections with 375 nmoles in 100 µL/dose of SW V-49s and vehicle for 10 days SV119. Erastin, equimolar mix of SV 119 and Erastin. Tumors were measured every other day with a digital caliper. Several mice from different treatment groups were sent to the Division of Comparative Medicine in our institution for pathologic evaluation. Blood was collected for complete blood count (CBC) and biochemical analysis (AST, ALT, BUN, total bilirubin, and Cr). Organs were examined grossly and histologically.

Figure 14A:
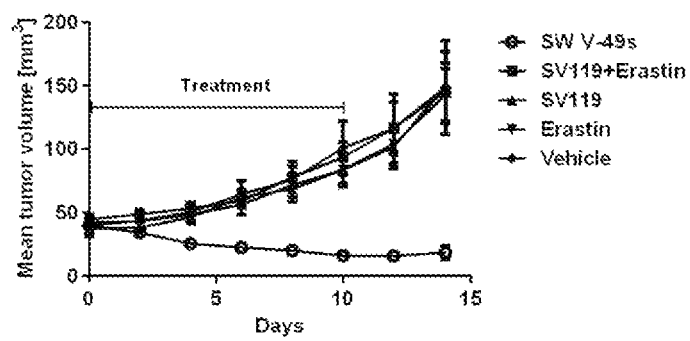
Figure 14B:
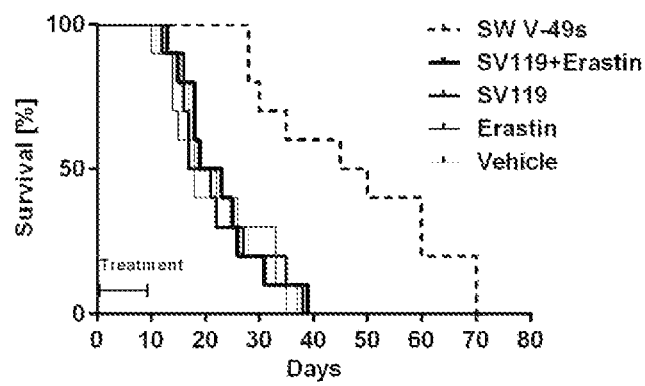

In the syngeneic cancer model (KCKO in C57BL/6), only the SW V-49s was capable of reducing the mean tumor volume (FIG. 14A, p=0.0003). None of the other reagents alone or in combination resulted in a reduction in tumor growth, and they all had similar growth rates to the vehicle (control), (FIG. 14A, p=0.9). The median survival for the group treated with SW V49s was 48 days compared to (18-21) days for the other groups (FIG. 14B, Kaplan-Meier survival curve, $p<0.001$). Of note, no gross abnormalities in the mice behavior (grooming) or any drug-related deaths were recorded. This was supported by the unchanged serum labs (CBC, AST, ALT, BUN, total bilirubin, and Cr), (tables 5 and 6). In addition, organs analyses (brain, heart, lungs, alimentary tract, kidneys, liver and pancreas), did not reveal any obvious signs of adverse drug effects, except a mild peritonitis.

TABLE 6

SW V-49s Does Not Induce Changes In Blood Cytology (CBC) Following Treatment Of C57BL/6 Mice.

| ID | WBC (10³/μL) | RBC (10⁶/μL) | HGB (g/dl) | PCV (%) | MCV (u) | MCH (pg) | MCHC (%) | Platelets (10³/μL) |
|---|---|---|---|---|---|---|---|---|
| Control 1 | 7.72 | 9.15 | 12.4 | 49.2 | 53.8 | 13.6 | 25.2 | 651 |
| Control 2 | 8.10 | 8.89 | 11.2 | 45.6 | 51.3 | 12.6 | 24.6 | 745 |
| Control 3 | 5.54 | 8.89 | 11.5 | 44.7 | 50.3 | 12.9 | 25.7 | 788 |
| Drug 1 | 4.16 | 7.66 | 9.8 | 37.7 | 49.2 | 12.8 | 26.0 | 611 |
| Drug 2 | 5.68 | 8.67 | 10.7 | 39.3 | 45.3 | 12.3 | 27.2 | 749 |
| Drug 3 | 3.34 | 8.40 | 10.5 | 42.4 | 50.5 | 12.5 | 24.8 | 885 |

Table 6 contains data from CBC of C57BL/6 mice treated with SW V-49s and vehicle (control) for 10 days. The differences in cell counts between the 2 groups are not statistically significant.

TABLE 7

SW V-49s Does Not Induce Changes In Serum Chemistry Following Treatment Of Tumor Bearing C57BL/6 Mice.

| ID | BUN (mg/dL) | Creatinine (mg/dL) | ALT (μ/L) | AST (μ/L) | Glucose (mg/dL) | Total Protein (g/dL) |
|---|---|---|---|---|---|---|
| Control 1 | 23 | 0.33 | 95 | 87 | 179 | 6.1 |
| Control 2 | 17 | 0.26 | 65 | 73 | 180 | 5.4 |
| Control 3 | 28 | 0.28 | 506 | 715 | 187 | 5.5 |
| Drug 1 | 19 | 0.22 | 138 | 167 | 178 | 5.1 |
| Drug 2 | 22 | 0.21 | 64 | 147 | 310 | 5.7 |
| Drug 3 | 17 | 0.24 | 63 | 55 | 180 | 5.1 |

Table 7 shows biochemical analysis of C57BL/6 mice treated with SW IV-134 and vehicle (control) for 10 days. The differences in laboratory values between the 2 groups are not statistically significant.

SW V-49s was also tested on a PDAC patient-derived mouse xenograft model, which is more clinically relevant. Surgical PDAC specimens (2×2 mm pieces) were obtained and implanted subcutaneously into the flanks of anesthetized NOD SCID mice. Then, tumors were harvested and implanted in the right flank of Athymic female nude mice (6 weeks old, National Cancer Institute Laboratories). These mice were treated with daily i.p. injections of SW IV-134 and vehicle for 14 days. Mice were randomized into 2 groups (n=15). Drug treatment was started when the mean tumors diameter was ~6 mm. Mice received daily intra peritoneal injections with 375 nmoles in 100 μL/mouse of SW V-49s and vehicle for 2 weeks. Tumors were measured every other day. Mice were euthanized when tumors reached a diameter of 2 cm or ulcerated.

Figure 14C:
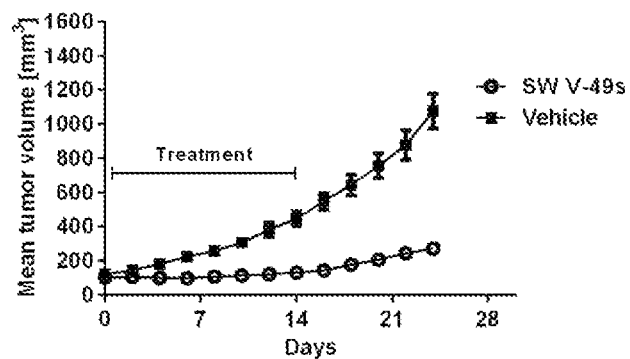
Figure 14D:
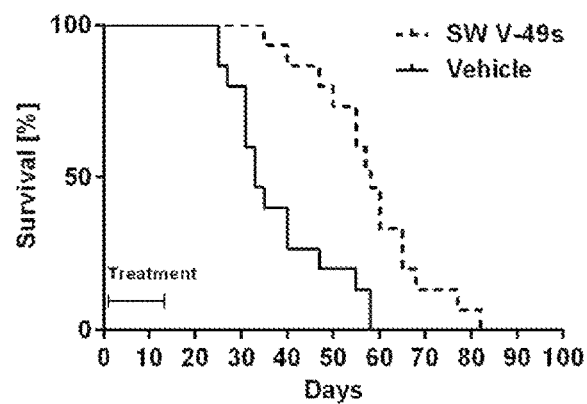

In this model, SW V-49s markedly slowed the growth rate of the established tumors (FIG. 14C. p<0.0001). The median survival for the group treated with SW V-49s was 58 days compared to 33 days for the vehicle group (FIG. 14D, Kaplan-Meier survival curve, p=0.0002). Mice tolerated the treatment well without obvious off-target effects.

Figure 14E:
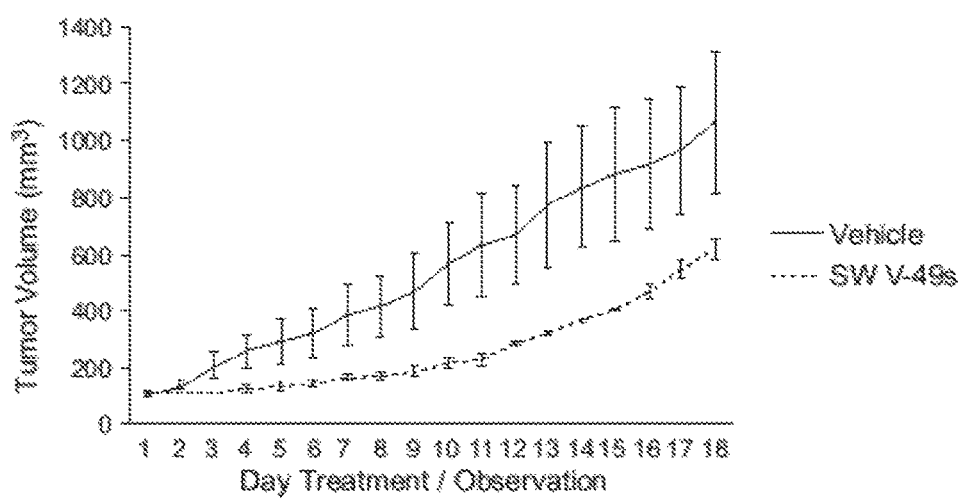

SYO-1 Synovial sarcoma (SS) xenografts were also treated with 300 nmoles SW V-49. Growth inhibition in a rapidly growing model of SS was observed. FIG. 14E depicts athymic nude mice xenograft of SS cell line SYO-1 treated with SW V-49 (300 nmoles) for 14 days and then followed, p<0.0001. SYO xenografts required a smaller dose of SW V-49 to achieve results similar to those achieved against PDAC. These results demonstrate the high efficacy of SW V-49s in both pancreatic cancer and synovial sarcoma and indicate its selective delivery.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited are hereby incorporated by reference, each in its entirety. Applicant reserves the right to challenge any conclusions presented by the authors of any reference.

What is claimed is:

1. A compound of structural Formula IV

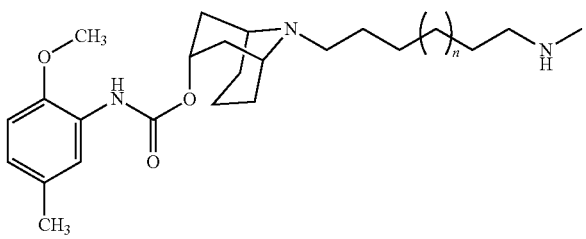

(IV)

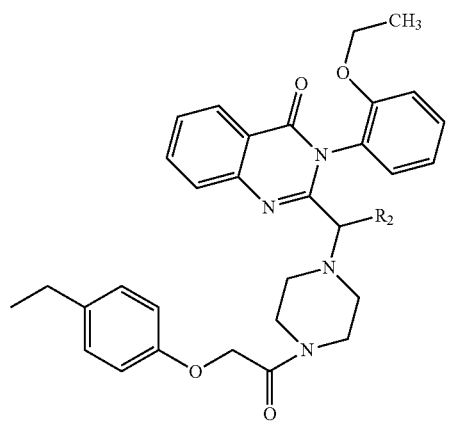

or salt thereof, wherein n is an integer chosen from 1, 2, 3, 4, and 5, and $R_2$ is H or methyl.

2. A compound or a salt thereof in accordance with claim 1, wherein n=1 and $R_2$ is H.

3. A compound or a salt thereof in accordance with claim 1, wherein n=5 and $R_2$ is H.

4. A compound or a salt thereof in accordance with claim 1, wherein the salt is an oxalate or a hydrochloride salt.

5. A compound chosen from:
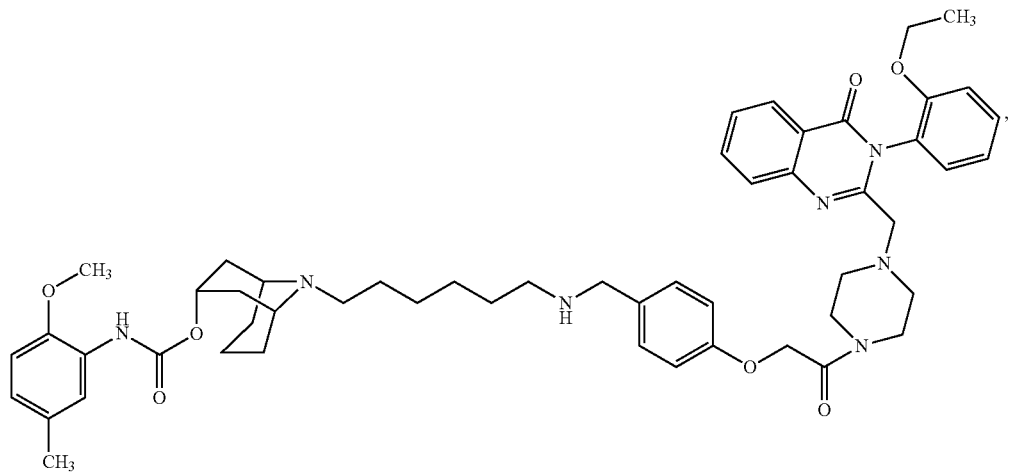
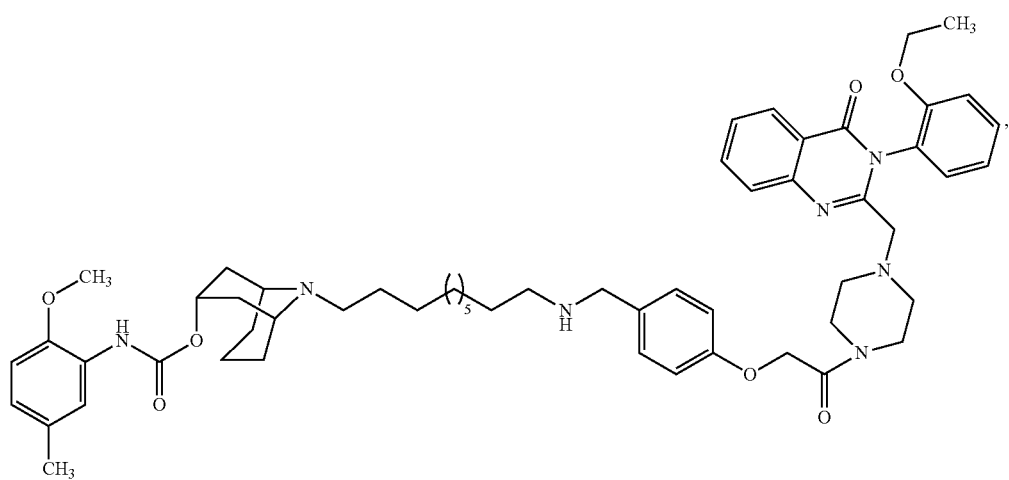
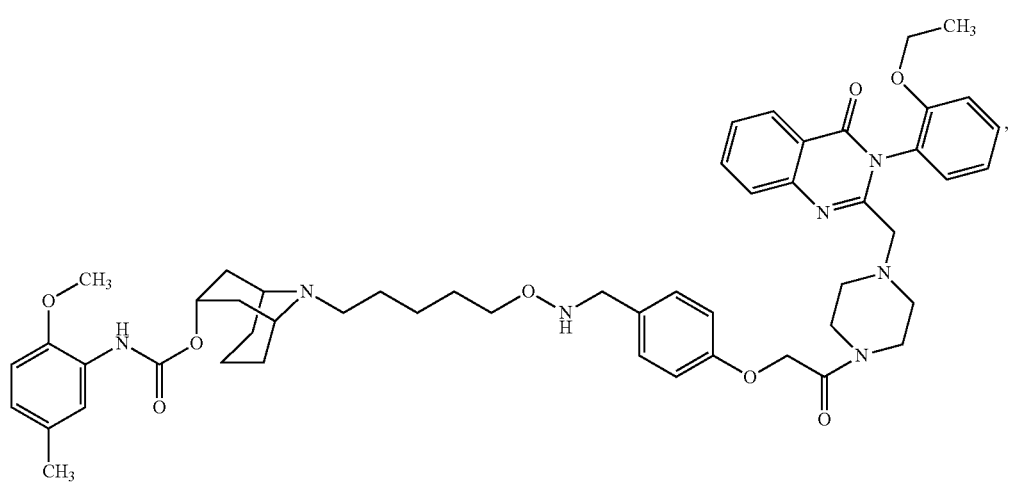

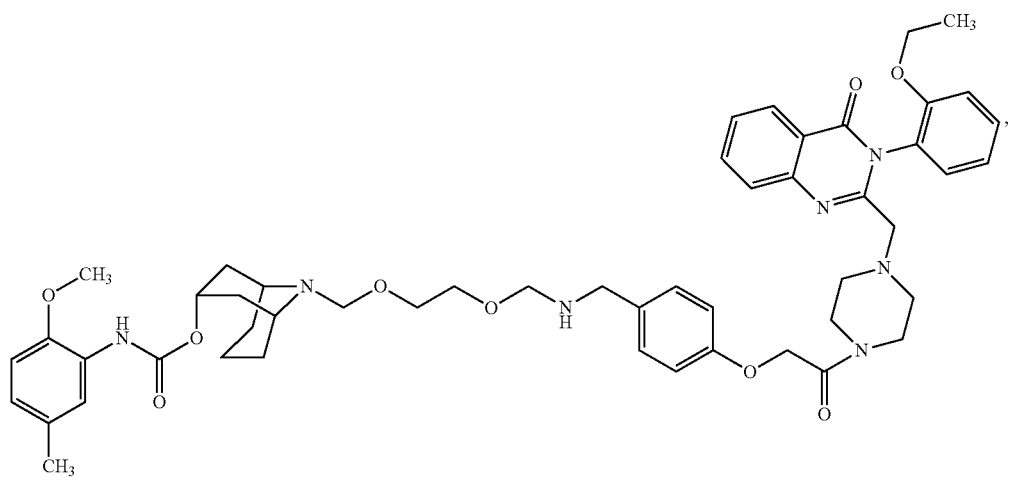
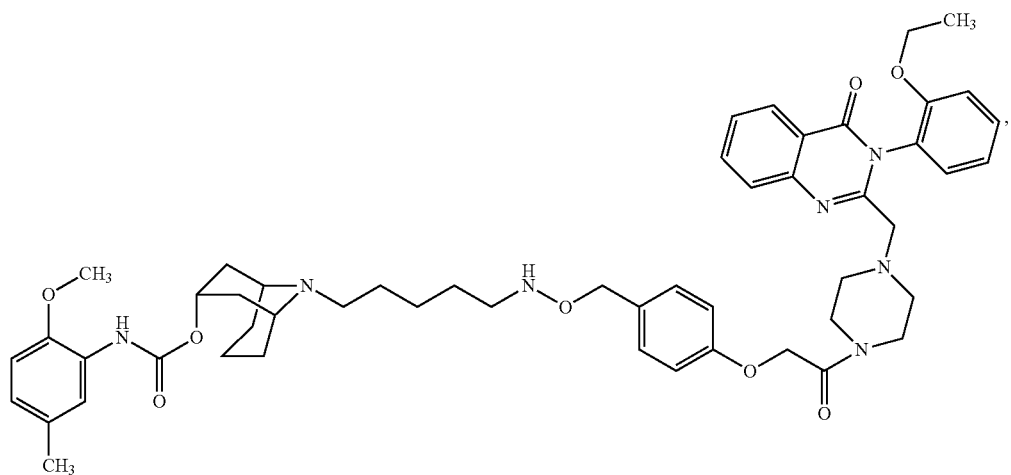
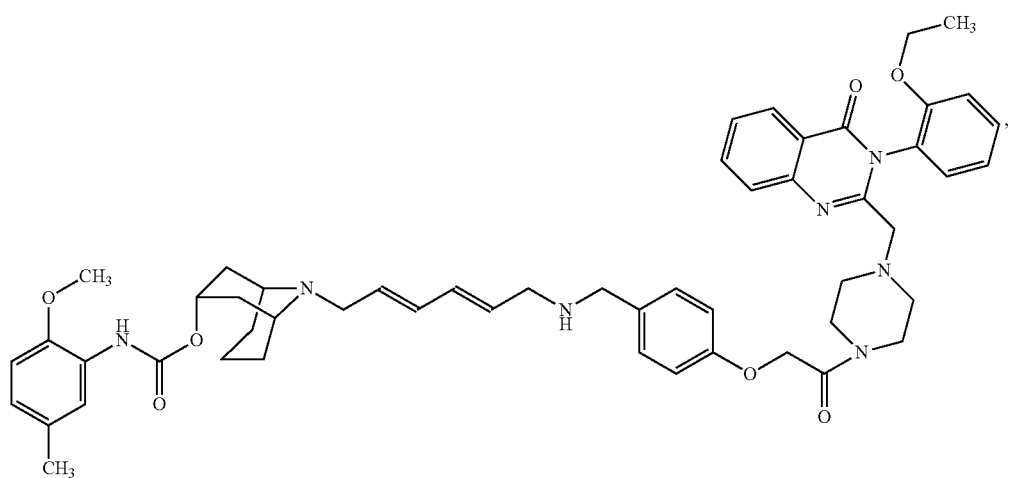

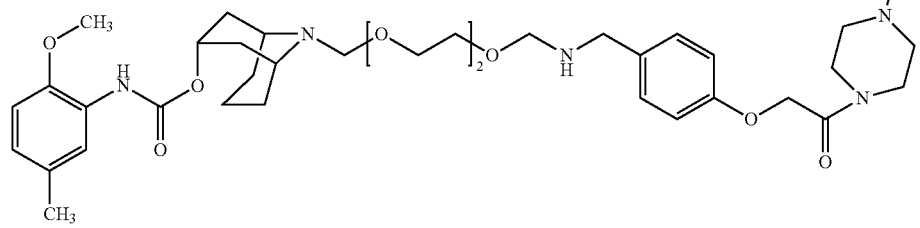
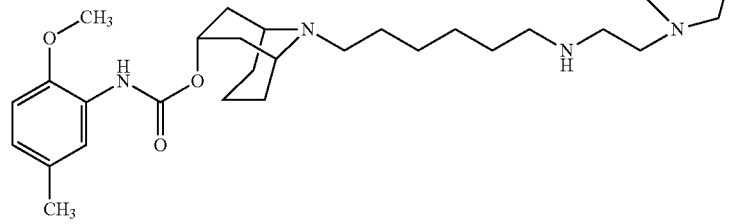
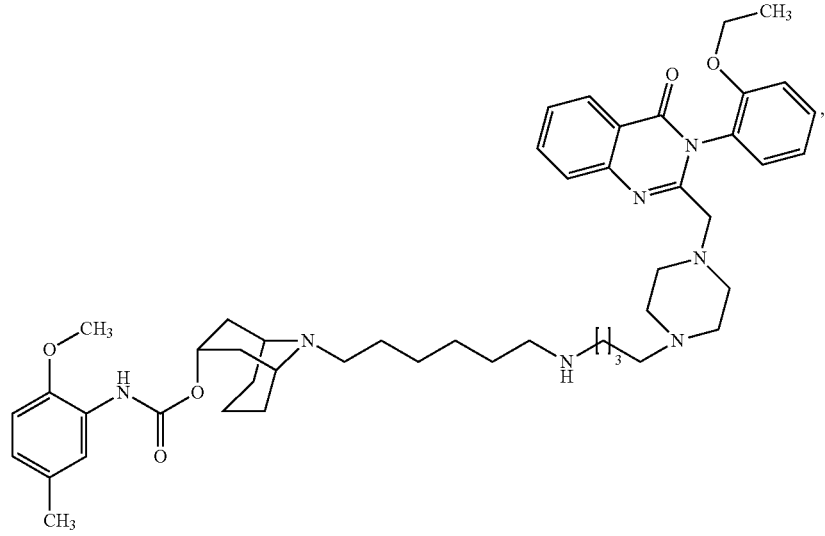

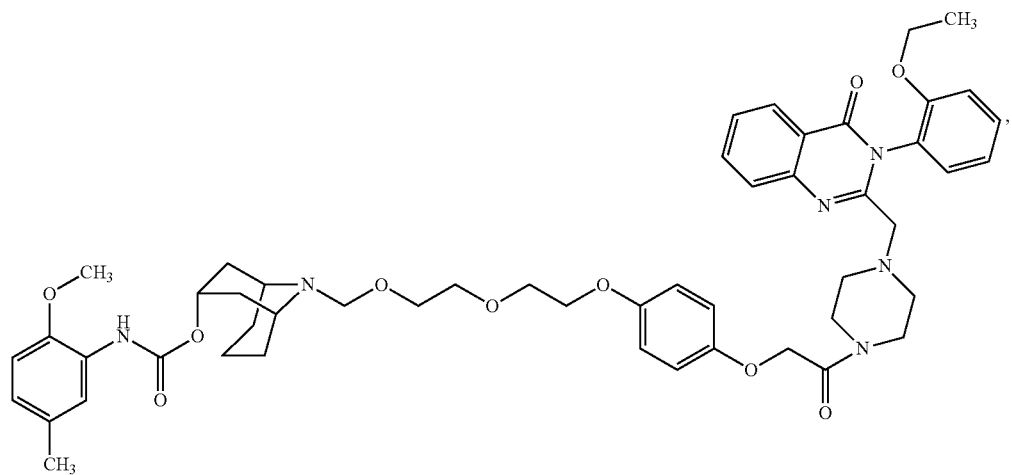
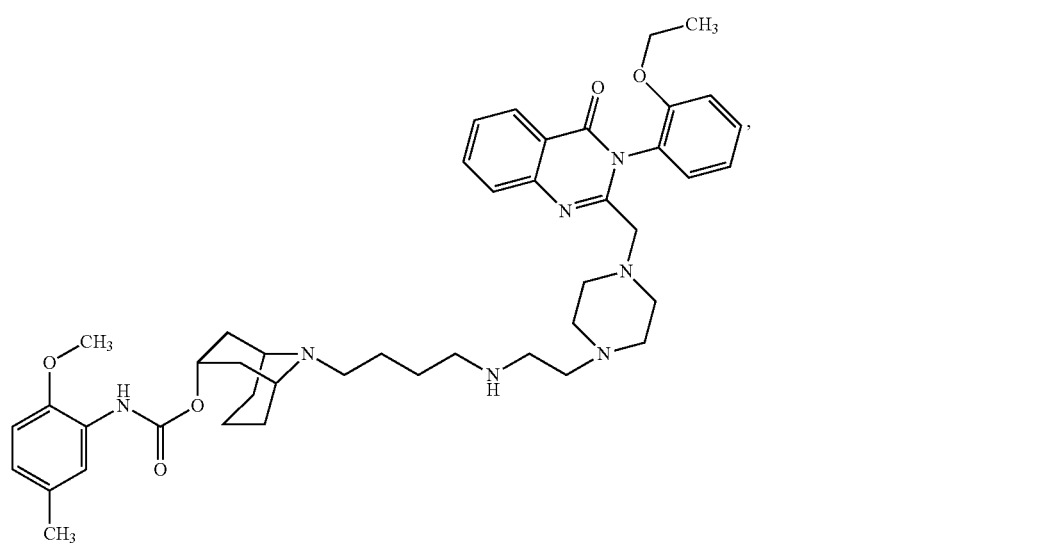
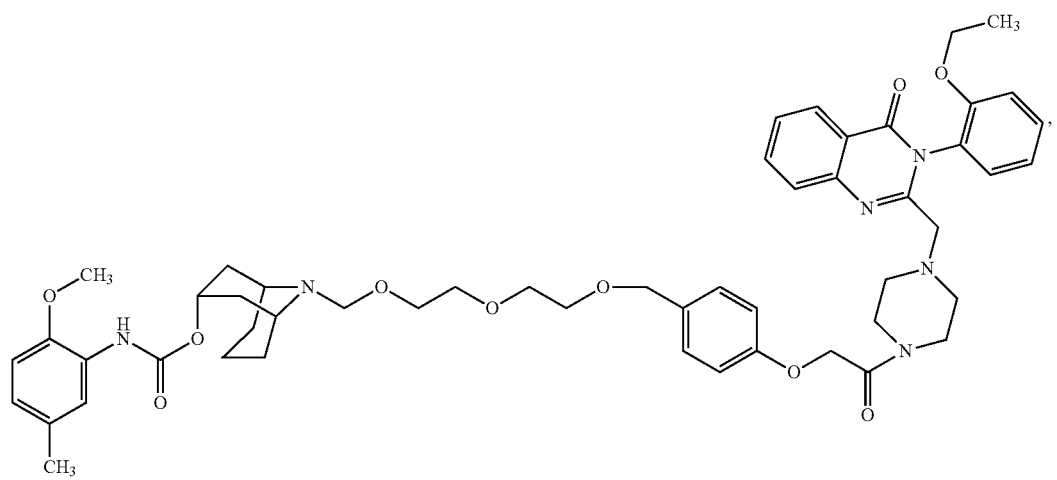

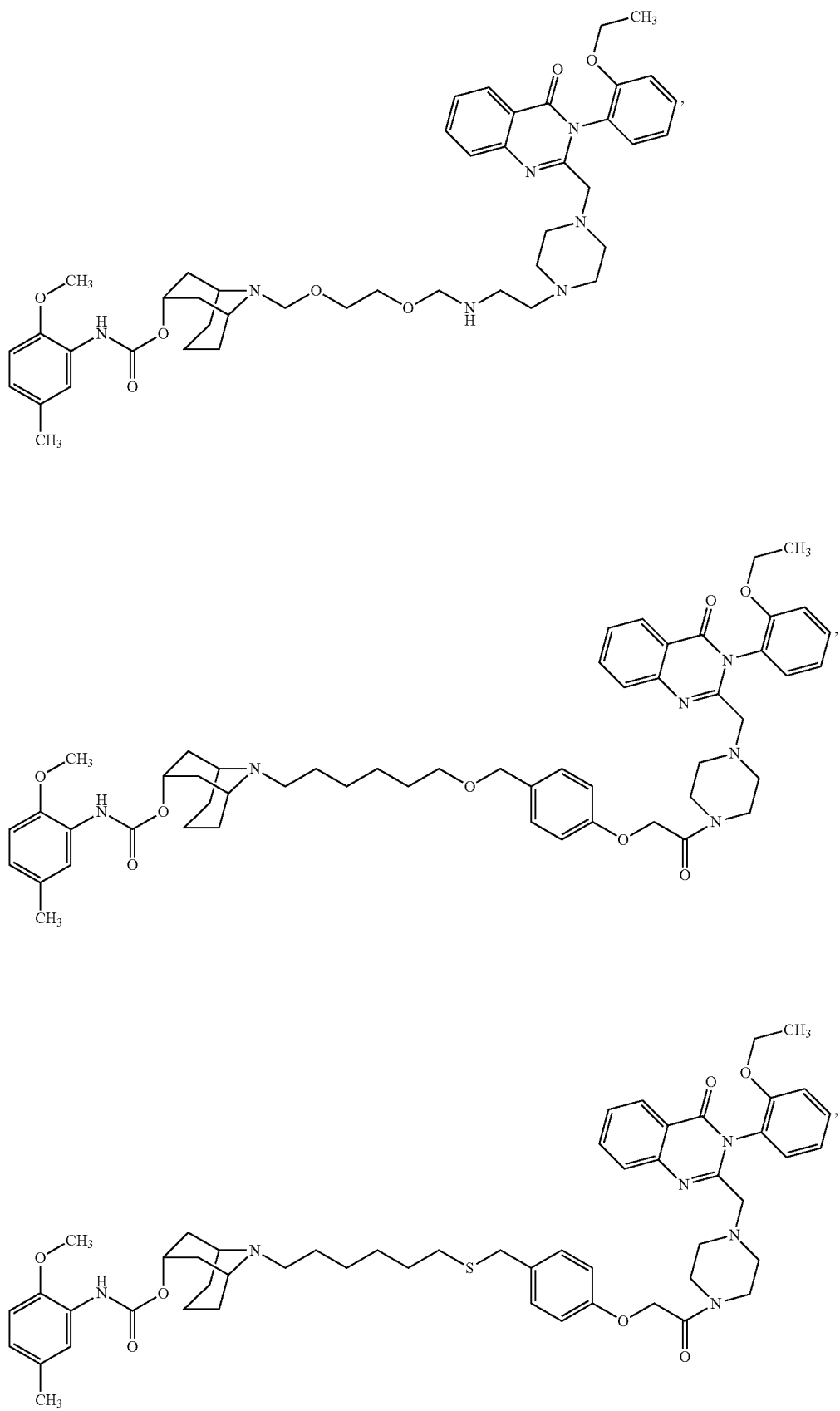

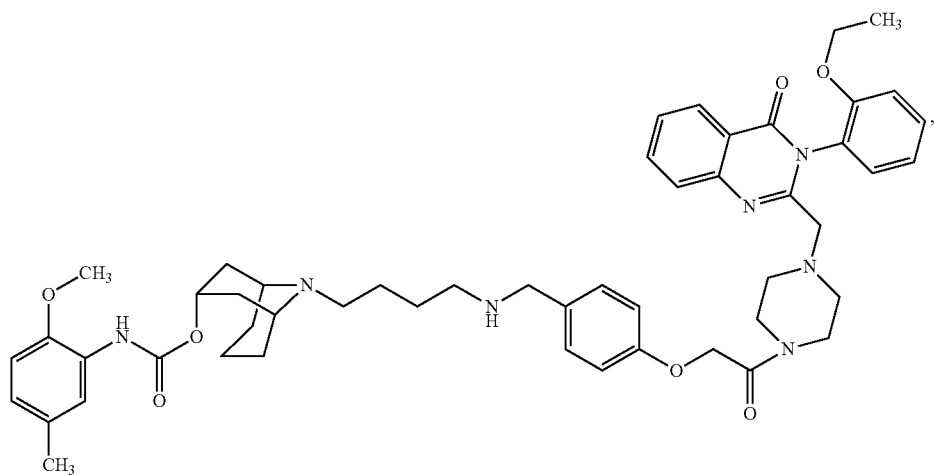
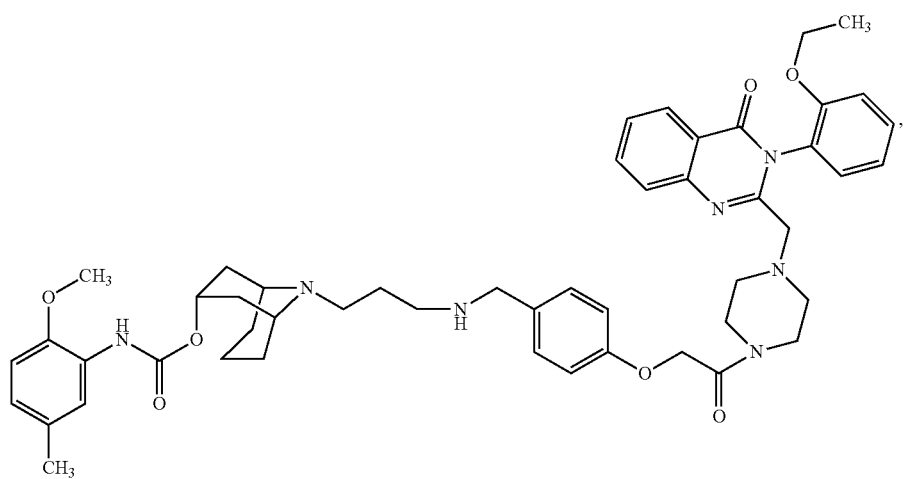
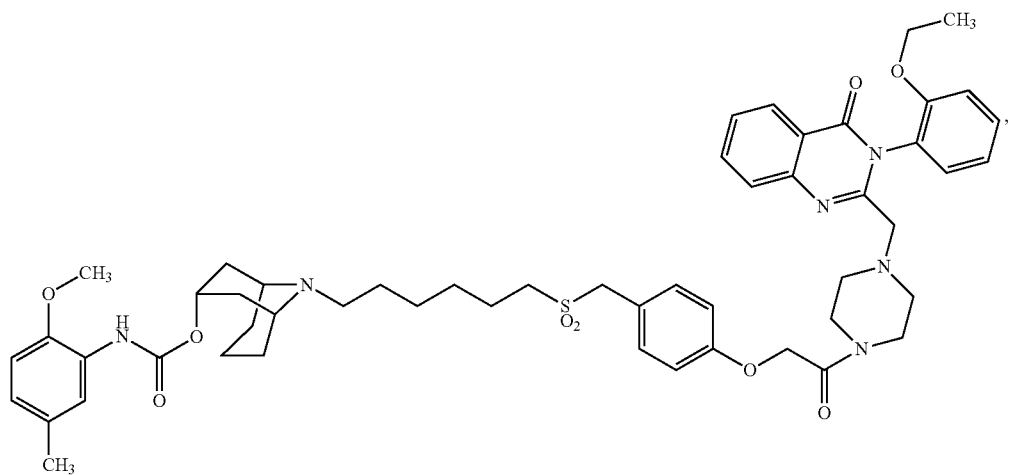

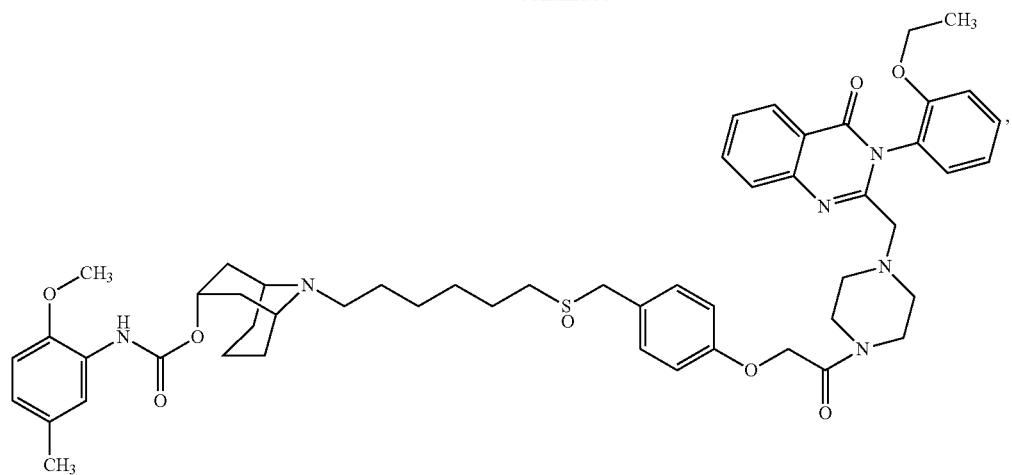
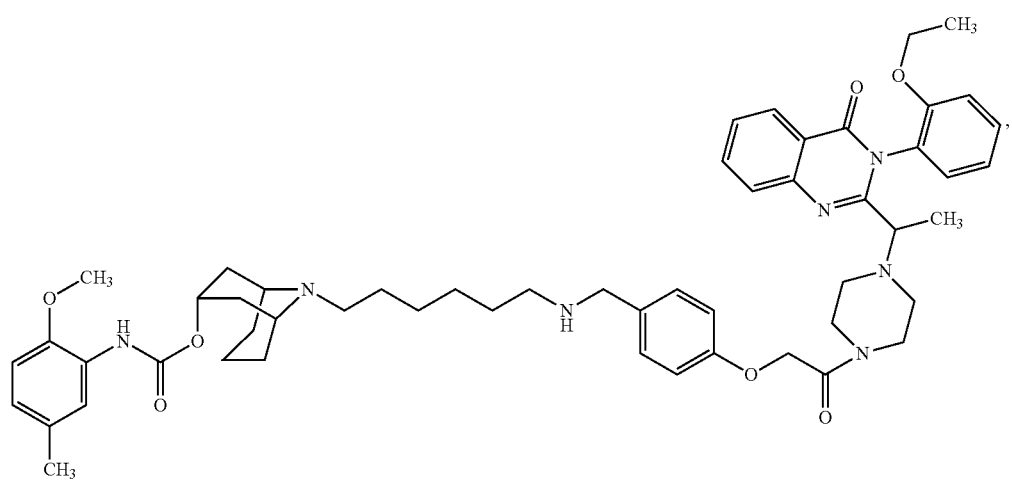
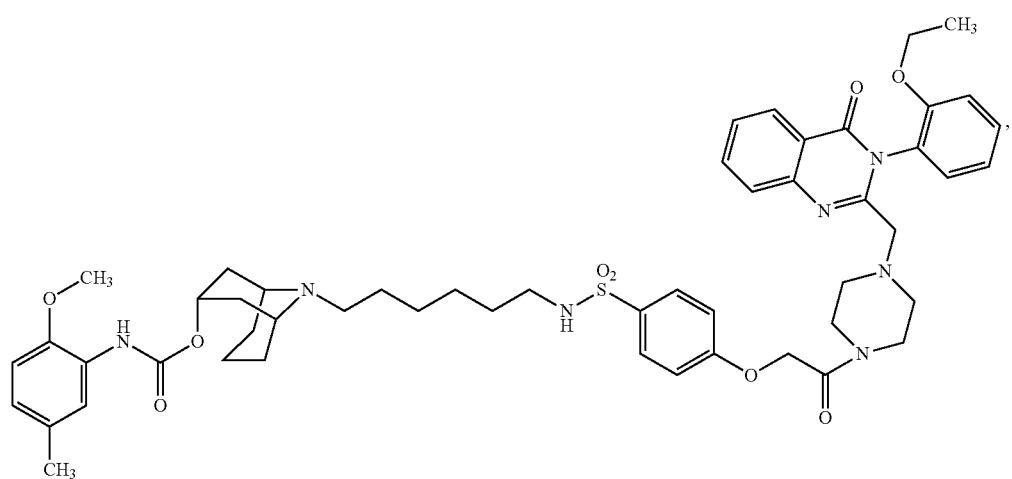

-continued

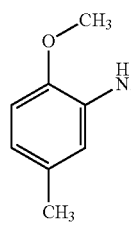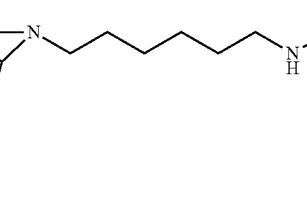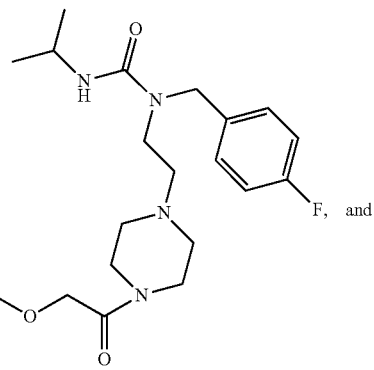

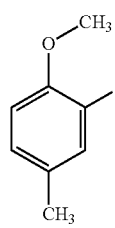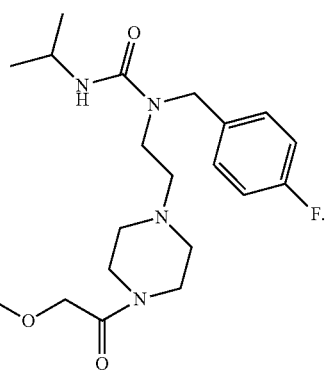

6. A composition comprising a compound of claim 1 and a pharmaceutically acceptable carrier, adjuvant, or vehicle.

7. A method of treating a pancreatic cancer or a synovial sarcoma in a subject in need thereof, comprising the step of administering to the subject a therapeutically effective amount of a compound of claim 1, or a salt thereof.

8. The method according to claim 7, wherein the subject is a human.

9. A method of treating a pancreatic cancer or a synovial sarcoma in a subject in need thereof, comprising administering the compound or salt thereof is the compound or salt thereof of claim 2.

10. A method of treating a pancreatic cancer or a synovial sarcoma in a subject in need thereof, comprising administering the compound or salt thereof is the compound or salt thereof of claim 3.

11. A method of treating a pancreatic cancer or a synovial sarcoma in a subject in need thereof, comprising the sequential or co-administration of a compound of claim 1 or a pharmaceutically acceptable salt thereof, and an additional anticancer drug.

12. The method according to claim 11, wherein the anticancer drug is chosen from an alkylating agent, anthracycline, antimetabolite agent, crosslinking agent, DNA replication inhibitor, intercalator, microtubule disruptor, PARP inhibitor, radiomimetic agent, radiosensitizer, strand break agent, and topoisomerase II inhibitor.

13. The method according to claim 11, wherein the anticancer drug is chosen from aminoglutethimide, amsacrine, anastrozole, asparaginase, barasertib, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, olaparib, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

14. The method of claim 11, wherein the method further comprises administering radiation therapy.

15. The method of claim 11, wherein the method further comprises administering surgery, thermoablation, focused ultrasound therapy, cryotherapy, or any combination thereof.

16. A compound or a salt thereof in accordance with claim 2, wherein the salt is an oxalate or a hydrochloride salt.

17. A compound or a salt thereof in accordance with claim 3, wherein the salt is an oxalate or a hydrochloride salt.

18. A pharmaceutical composition comprising the compound of claim 2 and one or more pharmaceutically acceptable excipients, adjuvants, or vehicles.

19. A pharmaceutical composition comprising the compound of claim 3 and one or more pharmaceutically acceptable excipients, adjuvants, or vehicles.

20. A pharmaceutical composition comprising the compound of claim 4 and one or more pharmaceutically acceptable excipients, adjuvants, or vehicles.

21. A pharmaceutical composition comprising the compound of claim 16 and one or more pharmaceutically acceptable excipients, adjuvants, or vehicles.

22. A pharmaceutical composition comprising the compound of claim 17 and one or more pharmaceutically acceptable excipients, adjuvants, or vehicles.

23. A method for treating pancreatic cancer or synovial sarcoma, comprising administering a therapeutically effective amount of the pharmaceutical composition of claim 6 to a patient in need thereof.

24. A method for treating pancreatic cancer or synovial sarcoma, comprising administering a therapeutically effective amount of the pharmaceutical composition of claim 18 to a patient in need thereof.

25. A method for treating pancreatic cancer or synovial sarcoma, comprising administering a therapeutically effective amount of the pharmaceutical composition of claim 19 to a patient in need thereof.

26. A method for treating pancreatic cancer or synovial sarcoma, comprising administering a therapeutically effective amount of the pharmaceutical composition of claim 20 to a patient in need thereof.

27. A method for treating pancreatic cancer or synovial sarcoma, comprising administering a therapeutically effective amount of the pharmaceutical composition of claim 21 to a patient in need thereof.

28. A method for treating pancreatic cancer or synovial sarcoma, comprising administering a therapeutically effective amount of the pharmaceutical composition of claim 22 to a patient in need thereof.

* * * * *